US012043873B2

(12) United States Patent
Ye et al.

(10) Patent No.: US 12,043,873 B2
(45) Date of Patent: Jul. 23, 2024

(54) MOLECULE COUNTING OF METHYLATED CELL-FREE DNA FOR TREATMENT MONITORING

(71) Applicant: BillionToOne, Inc., Menlo Park, CA (US)

(72) Inventors: Patrick Ye, Palo Alto, CA (US); David Tsao, San Carlos, CA (US); Oguzhan Atay, Menlo Park, CA (US)

(73) Assignee: BillionToOne, Inc., Menlo Park, CA (US)

( * ) Notice: Subject to any disclaimer, the term of this patent is extended or adjusted under 35 U.S.C. 154(b) by 0 days.

(21) Appl. No.: 18/187,578

(22) Filed: Mar. 21, 2023

(65) Prior Publication Data

US 2023/0295741 A1 Sep. 21, 2023

Related U.S. Application Data

(60) Provisional application No. 63/322,014, filed on Mar. 21, 2022, provisional application No. 63/439,492, filed on Jan. 17, 2023.

(51) Int. Cl.
*C12Q 1/6886* (2018.01)
*C12Q 1/6806* (2018.01)
*C12Q 1/6869* (2018.01)

(52) U.S. Cl.
CPC ......... *C12Q 1/6886* (2013.01); *C12Q 1/6869* (2013.01); *C12Q 1/6806* (2013.01); *C12Q 2600/112* (2013.01); *C12Q 2600/154* (2013.01)

(58) Field of Classification Search
CPC ................ C12Q 1/6886; C12Q 1/6869; C12Q 2600/154
See application file for complete search history.

(56) References Cited

U.S. PATENT DOCUMENTS 5,846,719 A 12/1998 Brenner et al.
6,013,445 A 1/2000 Albrecht et al.
8,105,422 B2 1/2012 Betting et al.
8,195,415 B2 6/2012 Fan et al.
8,467,976 B2 6/2013 Lo et al.
8,688,388 B2 4/2014 Dzakula et al.
8,706,422 B2 4/2014 Lo et al.
8,877,442 B2 11/2014 Quake et al.
9,512,480 B2 12/2016 Lo et al.
9,944,973 B2 4/2018 Willey et al.
2007/0009884 A1 1/2007 Stoughton et al.
2007/0092869 A1 4/2007 Fulmer-Smentek et al.
2008/0124712 A1 5/2008 Hantash et al.
2008/0274458 A1 11/2008 Latham et al.
2010/0323352 A1 12/2010 Lo et al.
2011/0033861 A1 2/2011 Wu et al.
2011/0201507 A1 8/2011 Rava et al.
2012/0021919 A1 1/2012 Scholl et al.
2012/0270739 A1 10/2012 Rava et al.
2013/0022973 A1 1/2013 Hansen et al.
2013/0103320 A1 4/2013 Dzakula et al.
2013/0110407 A1 5/2013 Baccash et al.
2013/0130923 A1 5/2013 Ehrich et al.
2014/0195164 A1 7/2014 Lo et al.
2015/0099266 A1 4/2015 Samuels et al.
2015/0133391 A1 5/2015 De Vlaminick et al.
2015/0152474 A1 6/2015 Pawlowski et al.
2015/0284783 A1 10/2015 Canton
2016/0040229 A1 2/2016 Talasaz et al.
2016/0130649 A1 5/2016 Xie et al.
2016/0168564 A1 6/2016 Jacobson et al.
2016/0222391 A1 8/2016 Krieg et al.
2016/0251719 A1 9/2016 Umbarger
2016/0319345 A1 11/2016 Gnerre et al.
2017/0175187 A1 6/2017 Rabinowitz et al.
2017/0275691 A1 9/2017 Karius et al.
2017/0327869 A1 11/2017 Schutz et al.
2018/0010176 A1 1/2018 Patel
2018/0023125 A1 1/2018 Talasaz et al.
2018/0127804 A1 5/2018 Dean et al.
2018/0216195 A1 8/2018 Elnitski et al.
2018/0265917 A1 9/2018 Barany et al.
2019/0211395 A1* 7/2019 Tsao .................... C12Q 1/6876

FOREIGN PATENT DOCUMENTS

EP 3336197 A1 * 6/2018 ........... C12Q 1/6886
JP 2013-530727 A 8/2013
JP 2014-520509 A 8/2014

(Continued)

OTHER PUBLICATIONS

Applied Biosystems, "Application Note: Detection and Quantification of Sequence Variants from Sanger Sequencing Traces, Determination of minor alleles by analyzing peak height data," 2013, pp. 1-13.

Carr, I. M., et al., "Inferring relative proportions of DNA variants from sequencing electropherograms", Bioinformatics, vol. 25, Issue 24, Oct. 2009, pp. 3244-3250.

China National Intellectual Property Administration, Office Action, CN Patent Application No. 201980065828.6, dated Sep. 17, 2021, 11 pages.

China National Intellectual Property Administration, Second Office Action, Chinese Patent Application No. 201980065828.6, dated Apr. 13, 2022, 13 pages.

(Continued)

*Primary Examiner* — Joseph G. Dauner
(74) *Attorney, Agent, or Firm* — Fenwick & West LLP

(57) ABSTRACT

Methods to quantify methylation in a DNA sample include treating the sample to encode the presence or absence of DNA methylation, adding to the sample a set of synthetic molecules (e.g., quality control template (QCT) molecules), generating a co-amplification mixture, sequencing the co-amplification mixture, and determining a number of methylated molecules in the sample based on the number of methylated reads from the sample and a number of reads from the set of synthetic molecules.

30 Claims, 42 Drawing Sheets

Specification includes a Sequence Listing.

(56) References Cited

FOREIGN PATENT DOCUMENTS

| | | | |
|---|---|---|---|
| JP | 2015-521482 | A | 7/2015 |
| WO | WO 2011/091046 | A1 | 7/2011 |
| WO | WO 2011/156795 | A2 | 12/2011 |
| WO | WO 2012/058316 | A1 | 5/2012 |
| WO | WO 2012/129363 | A1 | 9/2012 |
| WO | WO 2014/039556 | A1 | 3/2014 |
| WO | WO 2014/082032 | A1 | 5/2014 |
| WO | WO 2014/127484 | A1 | 8/2014 |
| WO | WO 2017/165864 | A1 | 9/2017 |
| WO | WO 2017/210372 | A1 | 12/2017 |
| WO | WO 2018/031486 | A1 | 2/2018 |
| WO | WO 2019028462 | A1 | 2/2019 |
| WO | WO 2019/200341 | A1 | 10/2019 |

OTHER PUBLICATIONS

Curci, P.L. et al., "How a Small Double-Stranded Trick Can Mislead Sanger Sequencing", J Biomol Tech. vol. 26, Issue 3, Sep. 2015, pp. 80-82.

European Patent Office, Extended European Search Report, European Patent Application No. 19846980.1, dated Mar. 25, 2022, six pages.

European Patent Office, Extended European Search Report, European Patent Application No. 18898428.0, dated Sep. 27, 2021, eight pages.

IP Australia, Examination Report No. 1, AU Patent Application No. 2018399524, dated Nov. 8, 2021, four pages.

Japan Patent Office, Office Action, JP Patent Application No. 2020-537213, dated Aug. 17, 2021, ten pages.

Kaboev, O.K., et al., "PCR hot start using primers with the structure of molecular beacons (hairpin-like structure)," Nucleic Acids Research, vol. 28, No. 21, Sep. 12, 2000, pp. 1-2.

Lun, F.M.F., et al., "Noninvasive prenatal diagnosis of monogenic diseases by digital size selection and relative mutation dosage on DNA in maternal plasma.", PNAS vol. 105, Dec. 16, 2008, pp. 19920-19925.

PCT International Preliminary Report on Patentability, PCT Application No. PCT/US18/45434, dated Jul. 7, 2020, eight pages.

PCT International Preliminary Report on Patentability, PCT Application No. PCT/US2018/045394, dated Feb. 4, 2020, six pages.

PCT International Preliminary Report on Patentability, PCT Application No. PCT/US2018/045419, dated Feb. 4, 2020, 11 pages.

PCT International Search Report and the Written Opinion, PCT Application No. PCT/US2019/014340, dated Mar. 29, 2019, 22 pages.

PCT International Search Report and Written Opinion, PCT Application No. PCT/US2019/045331, dated Oct. 25, 2019, seven pages.

PCT International Search Report and Written Opinion, PCT Application No. PCT/US2018/045419, dated Dec. 21, 2018, 15 pages.

PCT International Search Report and Written Opinion, PCT Application No. PCT/US2018/045394, dated Oct. 10, 2018, eight pages.

PCT International Search Report and Written Opinion, PCT Application No. PCT/US2018/045434, dated Nov. 29, 2018, pp. 1-11.

Quail, M.A., et al., "SAS I-Seq: sample assurance Spike-Ins, and highly differentiating 384 barcoding for Illumina sequencing.", BMC Genomics, 2014, pp. 1-12.

Silas, S., et al., "Direct CRISPR spacer acquisition from RNA by a natural reverse transcriptase-Cas1 fusion protein,", Science 351(6276), Feb. 26, 2016, pp. 1-31.

Sinha, R. et al., "Index Switching Causes "Spreading-Of-Signal" Among Multiplexed Samples in Illumina HiSeq 4000 DNA Sequencing," Apr. 9, 2017, pp. 1-29.

Tourlousse, D.M. et al., "Synthetic spike-in standards for high-throughput 16S rRNA gene amplicon 4 sequencing," Nucleic Acids Research, vol. 45, No. 4, Dec. 15, 2016, pp. 1-14 and supplementary data.

Tsao, et al. "A novel high-throughput molecular counting method with single base-pair resolution enables accurate single-gene NIPT," bioRxiv, Apr. 3, 2019, pp. 1-20.

Yan, T-Z. et al., "Reliable Detection of Paternal SNPs within Deletion Breakpoints for Non-Invasive Prenatal Exclusion of Homozygous a-Thalassemia in Maternal Plasma", PLoS One, vol. 6, No. 9, e24779, Sep. 2011, pp. 1-9.

PCT Invitation to Pay Additional Fees, PCT Application No. PCT/US2023/64776, dated Jul. 5, 2023, 3 pages.

Kass, S.U. et al. "DNA Methylation Directs a Time-Dependent Repression of Transcription Initiation," *Current Biology*, vol. 7, No. 3, Mar. 1, 1997, pp. 157-165.

PCT International Search Report and Written Opinion, PCT Application No. PCT/US2023/64776, Oct. 19, 2023, 20 pages.

* cited by examiner

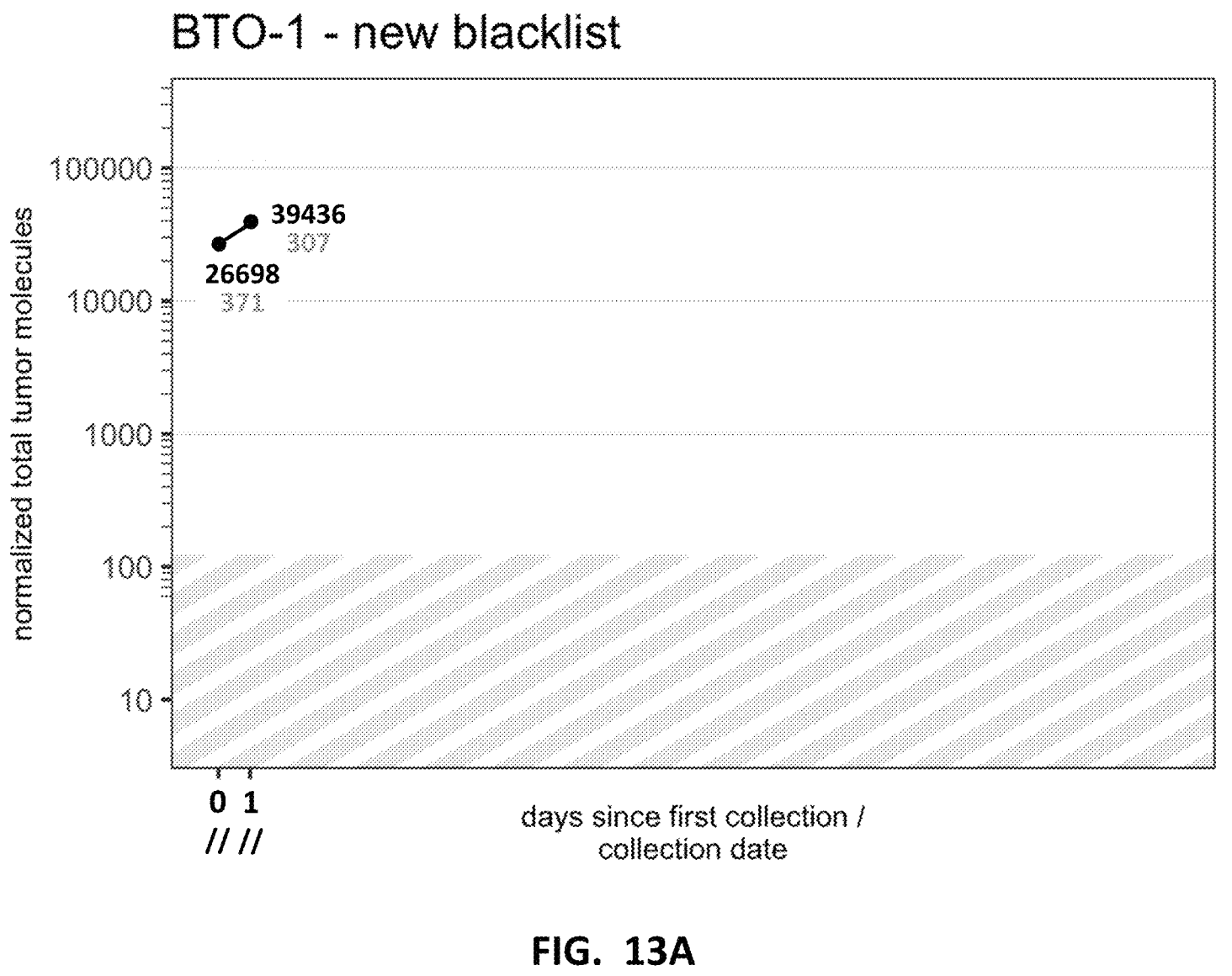

BTO-1 - new blacklist normalized total tumor molecules 100000
10000
1000
100
10

39436
307
26698
371

0 1 days since first collection / collection date

FIG. 13A

MOLECULE COUNTING OF METHYLATED CELL-FREE DNA FOR TREATMENT MONITORING

1. CROSS-REFERENCE TO RELATED APPLICATIONS

This application claims the benefit of and priority to U.S. Provisional Application No. 63/322,014, filed on Mar. 21, 2022, and U.S. Provisional Application No. 63/439,492, filed on Jan. 17, 2023, each of which is hereby incorporated by reference in its entirety.

2. SEQUENCE LISTING

The instant application contains a Sequence Listing with 2 sequences, which has been submitted via Patent Center and is hereby incorporated by reference in its entirety. Said XML copy, created on Mar. 18, 2023, is named 38227-55032-SequenceListing-US.xml, and is 2,905 bytes in size.

3. BACKGROUND

While novel cancer treatments continue to be developed at an unprecedented pace, assessing whether cancer treatment is effective for a particular patient remains relatively cumbersome and qualitative. Imaging is the gold standard for measuring the state of a cancer; however, PET/CT and CT scans impart harmful radioactive dose to the patient, and these imaging facilities may be located far from where the patient lives. Imaging sessions are scheduled several months apart, which limits how quickly oncologists can get a sense of how the cancer is responding to a treatment. Qualitative metrics such as physical exam and patient reported symptoms are often confounded by treatment side effects and therefore are not sufficiently accurate for assessing treatment efficacy. Nevertheless, oncologists want to assess the extent to which a patient's cancer is responding to treatment to inform the treatment plan, such as whether the patient should continue with existing therapy or switch to a new therapy plan.

Non-invasive liquid biopsies that assay the cell-free DNA (cfDNA) have been developed to quantify the levels of circulating tumor DNA (ctDNA) from a blood sample. Several studies have found levels of ctDNA to be useful and quantifiable information for longitudinal ctDNA measurements that accurately track tumor progression. Many assays specifically quantify the abundance of somatic mutations (e.g. single nucleotide variants, copy number alterations, insertions, deletions) using the variant allele fraction (VAF) and track these VAFs over time. However, assays that rely on quantifying somatic mutations have limitations. Because the VAF can be quite small (~0.1-0.5%), there can be significant and unavoidable molecular sampling limitations. False negatives can occur for variants present at low VAF; a sample with 2 variant molecules on average may actually have 0 variant molecules 13.5% of the time simply due to Poisson sampling. Even if a variant is detected, the noise of that measurement is high due to the small number of variant molecules. For example, 9 variant molecules in a sample will have a standard deviation of 3 variant molecules due to sampling noise, resulting in a coefficient of variance (CV) of 33%. Low numbers of molecules can make time serial measurements based on VAFs noisy and difficult to interpret. Yet understanding the extent of molecule sampling limitations requires an estimate of the number of variant molecules, but this is information that many assays do not provide.

Therefore, there is a need for absolute quantification to determine the number of variant molecules that are present. Digital droplet PCR has been shown to be a sensitive approach to detect ctDNA. However, only a few genomic locations at most can be probed simultaneously because of the limited amount of initial sample.

Given the molecule sampling challenges associated with assaying somatic mutations, methylation has been explored as an alternative biomarker for ctDNA. Methylation has long been shown to be a strong, consistent, and genomically widespread biomarker for cancer. However, while methylation signal is much more abundant compared to that from somatic mutations, quantifying the amount of methylation accurately and precisely is a challenge. Methylation-specific qPCR is a commonly used method; however, because of the exponential nature of the assay, qPCR Ct measurements have high CV (typically in the 10s of percent). Improving the accuracy with multiple replicates is challenging given the limited sample amount. In addition, non-tumor cfDNA can contribute background methylation signal, complicating the task of quantifying the signal that belongs to ctDNA. Furthermore, sampling multiple locations for methylation would help improve assay performance, but interrogating multiple loci using qPCR is difficult and time consuming.

4. SUMMARY

Provided herein is a methylation-based approach to more accurately and precisely assess treatment monitoring for, for example, cancer patients. The methylation-based approach is a pan-cancer assay that provides longitudinal determination of cancer burden via methylation assessment. The assessment can identify a multi cancer methylation signature based, in part, on nucleotides (DNA) being methylated in specific locations in cancer.

An accurate count of methylated DNA molecules in a blood sample can inform the status of a patient's cancer. Because some methylated molecules are sparse (i.e., low concentration in the sample), they must be amplified in order to be detected. However, amplification can confound the challenge of detecting methylated molecules because it can be noisy and methylated molecules amplify at different rates. Here, Applicants developed a methylation-based approach that adds quantitative counting templates (QCTs) prior to amplification, which provide a measurement tool that allows for quantification after this step to determine how many methylated molecules were initially in the sample.

The methylation-based approach is distinct from other assays that rely on single nucleotide variant (SNV)-based ctDNA monitoring because methylated ctDNA is a global and additive marker that allows for a more robust and cumulative measurement of ctDNA. Typical SNV-based ctDNA monitoring assays such as tumor-informed MRD assays look at an average of 9 SNVs, whereas the methods described herein may typically quantify an average of 90 methylated loci; a 10-fold increase in signal.

The methylation-based approached described is a next generation sequencing (NGS)-based test designed to measure the change in methylated tumor molecules in a cancer patient from a blood draw. In particular, the method quantifies the methylated ctDNA (circulating-tumor DNA) molecules isolated from cell-free DNA (cfDNA) at loci known to be hypermethylated in tumors compared to healthy tissue.

In one embodiment, plasma and buffy coat are isolated from whole blood collected form a patient. Cell-free DNA (cfDNA) is extracted from the plasma, and DNA (e.g., genomic DNA) is extracted from the buffy coat. The number of methylated molecules is quantified in both cfDNA and DNA (from the buffy coat) using QCT's (e.g., as described in U.S. Pat. Pub. Nos. 2020/0040380A1, 201910095577A1, 201910114389A1, and 201910211395A1, which are incorporated by reference) at >500 locations in the genome known to be hypermethylated in cancer compared to non-cancerous tissue and blood. Methylation measured in DNA (e.g., methylated DNA in buffy coat) is subtracted from cfDNA methylation (e.g., methylated molecules from plasma) in order to remove background from the ctDNA signal. The remaining cfDNA methylated molecules are summed across all hypermethylation locations to quantify the DNA methylation in the sample (e.g., to calculate the Tumor Methylation Score).

The quantified DNA methylation in the sample (e.g., the Tumor Methylation Score in the sample) from the current collection can be compared to a most recently reported quantified DNA methylation (e.g., Tumor Methylation Score) to determine an increase, decrease, or no change call. An increase or decrease may be reported if the change in quantified DNA methylation achieves a significance threshold. No interpretive calls (e.g., an increase or a decrease) for change in quantified DNA methylation are made for baseline tests without any prior collections. The limit of detection (LOD) enables detection of a 0.2 percentage point change in tumor fraction with 3 standard deviations of separation.

The present disclosure features a method for quantifying the number of methylated molecules present in a sample using quantitative counting templates (QCTs). For example, a sample containing DNA sequences (e.g., a mixture of methylated and unmethylated DNA sequences) is treated to convert unmethylated cytosines to uracils in the DNA sequences (i.e., treated to encode the presence or absence of DNA methylation in the DNA sequences). In some cases, a sample is sparsely populated with DNA sequences containing methylated cytosines, which then requires amplification in order for these DNA sequences to be detected and quantified. As noted above, amplification complicates the ability to quantify the methylated molecules. Addition and co-amplification of QCTs alleviates these complications. Therefore, QCTs are added to the sample and co-amplification with the treated DNA sequences to produce a co-amplification mixture. The co-amplification mixture is then sequenced. Sequencing and subsequent analysis determine the number of QCT molecules, the number of methylated cytosines, and the number unmethylated cytosines. Alternatively, sequencing and subsequent analysis determine the number of QCT molecules and the number of methylated sequencing reads (i.e., sequencing reads containing an uracil). The number of methylated molecules in the sample is quantified based on the number of methylated reads and the number of reads from the QCT molecules. The quantified methylated molecules can then be used to facilitate diagnosis, treatment, or further assessment of the subject.

This methylation-based approach can also be used to determine when a different assay performed on the same sample is reliable, or not. For example, when a sample is subjected to two assays: (1) an assay to determine abundance of a somatic mutation (e.g., a variant allele fraction (VAF) measurement) and (2) an assay to quantify DNA methylation using QCT molecules as described herein, the latter can be used to inform the reliability of the former. In particular, quantification of the number of methylated molecules (based on the QCT molecules) as one indicator of the presence of cancer in the sample can be used to determine if the variant allele fraction measurement (another indicator of the presence of cancer) from the sample is reliable. This is possible because the QCT molecules in the methylation assay provide an accurate and reliable way to determine the number of methylated molecules in the sample, which avoid false negatives or false positives. Practically, this means that when a VAF measurement and a methylation analysis are performed on material from the same sample, the accuracy and reliability of the methylation measurement can be imparted on the VAF measurement to give the VAF a reliability score (e.g., a "true call" (i.e., when the VAF should be trusted) or a "no-call" (i.e., when the VAF should not be trusted)). For example, when a VAF is small (~0.1-0.5%), this may be reported as a "negative" for the presence of cancer. If the corresponding quantification of methylated DNA (using the methods described herein) indicates the presence of cancer (e.g., the number of methylated DNA sequences are above a predetermined threshold), then the VAF is a "false negative" or a "no-call" and the VAF measurement should not be trusted. Importantly, these results can suggest the need for additional assessment of the subject, for example, a new treatment selection assay, genomic profiling, and/or a change to the treatment regimen.

This methylation-based approach can also be used to determine change in a methylation profile in a subject over time. A change in a methylation profile in a subject may indicate the presence of cancer or a change in a pre-existing cancer. The appearance of novel methylated loci at a subsequent time point, increased contribution of a methylated loci to the overall methylation signal at a subsequent time point, or a combination thereof are indications of change in methylation profile in subject. Notably, the methylation-based approached described herein enables precise determination of methylation profiles due to the use of QCT molecules, and the QCT molecule's ability to reliably and accurately quantify the number of methylated molecules at each time point. This is the functionality that allows comparison between time points, enabling determination of a methylation profile in a subject over time. Other ctDNA assays lack accuracy and reliability between measurements performed at different time points, and therefore, these assays cannot measure methylation profiles in a subject over time. As such, the ability to measure a change in methylation profile that then informs the subject's oncologists' strategy with respect to diagnosis, treatment, and additional assessment is unique to the methylation-based approached described herein.

Overall, the present disclosure features a method for quantifying the number of methylated molecules present in a sample using quantitative counting templates (QCTs) in a multiplex fashion. Background subtraction using the methylation signal from a sample's corresponding buffy coat reduces the noise in the assay as well as improve robustness against genomic DNA (gDNA) contamination. Background levels of methylation in healthy subjects varies from day-to-day, suggesting the importance of background subtraction for these time serial measurements. This approach can be adapted to measure methylation signal in multiple cancer types using a single assay chemistry.

In one aspect, this disclosure features a method to quantify DNA methylation in a sample comprising cell free DNA (cfDNA) sequences, the method comprising: treating the sample to encode presence or absence of DNA methylation in the cfDNA sequences, wherein the sample comprises at least ten target loci from the cfDNA sequences, wherein each locus of the at least ten target loci is chosen due to an expected increase in DNA methylation at each loci in cancerous tissue compared to non-cancerous tissue; adding to the sample a set of synthetic molecules, the set of molecules comprising: target-associated regions having a nucleotide sequence that matches a target sequence region of an endogenous target molecule comprising at least one of the target loci, and variation regions with a nucleotide sequence that does not match a sequence region of an endogenous target molecule; generating a co-amplification mixture comprising an amplified set of synthetic molecules and an amplified set of at least ten target loci from the cfDNA sequences; sequencing the co-amplification mixture at a read depth of at least one read sequence per molecule in the sample to generate sequence reads; determining a number of the sequence reads that are methylated sequence reads; determining a number of methylated molecules in the sample for each target loci based on the number of methylated reads from the sample for each target loci and a number of sequence reads from the set of synthetic molecules; and aggregating the number of methylated molecules across at least two of the at least ten target loci to quantify DNA methylation in the sample.

In some embodiments, the method further comprises processing the methylated sequence reads using one or more of the following: filtering out selected hypermethylated target loci; or subtracting background methylation.

In some embodiments, the sample is taken from a blood draw comprising plasma and buffy coat, wherein the plasma comprises cfDNA and the buffy coat comprises genomic DNA (gDNA) sequences.

In some embodiments, method further comprises extracting cfDNA from the plasma and gDNA sequences from the buffy coat from the sample prior to treating the sample to encode the presence or absence of DNA methylation.

In some embodiments, treating the sample to encode presence or absence of DNA methylation comprises bisulfite conversion or enzymatic conversion.

In some embodiments, the set of synthetic molecules is a set of quantitative counting templates (QCTs).

In some embodiments, the method further comprises quantifying DNA methylation in a sample containing DNA sequences from the buffy coat.

In some embodiments, the method further comprises: treating the sample comprising DNA sequences from buffy coat to encode the presence or absence of DNA methylation in the DNA sequences, wherein the sample comprises at least ten target loci from the DNA sequences, wherein each locus of the at least ten target loci is chosen due to an expected increase in DNA methylation at each loci in cancerous tissue compared to non-cancerous tissue; adding to the sample a set of synthetic molecules, the set of molecules comprising: target-associated regions having a nucleotide sequence that matches a target sequence region of an endogenous target molecule comprising at least one target loci, and variation regions with a nucleotide sequence that does not match a sequence region of an endogenous target molecule; generating a co-amplification mixture comprising an amplified set of synthetic molecules and an amplified set of at least ten target loci from the DNA sequences; sequencing the co-amplification mixture to generate sequence reads; determining a number of the sequence reads that are methylated sequence reads; determining a number of methylated molecules in the sample based on the number of methylated reads from the sample and a number of reads from the set of synthetic molecules; and aggregating the number of methylated molecules across at least two target loci to quantify DNA methylation in the sample containing DNA sequences from the buffy coat, thereby quantifying DNA methylation in gDNA sequences from buffy coat.

In some embodiments, treating the sample to encode presence or absence of DNA methylation comprises bisulfite conversion or enzymatic conversion.

In some embodiments, the set of synthetic molecules is a set of quantitative counting templates (QCTs).

In some embodiments, the method further comprises adding a spike-in of known sequence and quantity to the sample prior to the treating step.

In some embodiments, at least 100 target loci are amplified or at least 500 target loci are amplified.

In some embodiments, the co-amplification mixture is sequenced at a read depth of 10 or more reads per molecule, 100 or more reads per molecule, or 1000 or more reads per molecule.

In some embodiments, the sample further comprises at least one normalization locus that is expected to have high methylation in cfDNA across both cancerous and non-cancerous tissue.

In some embodiments, the co-amplification mixture comprises an amplified set of synthetic molecules, an amplified set of all or a subset of the at least 10 target loci, and an amplified at least one normalization locus.

In some embodiments, the aggregating step comprises aggregating target loci from the at least ten target loci that contain lower than a threshold amount of methylated molecules in the buffy coat sample.

In some embodiments, the method further comprises normalizing the aggregate number of methylated molecules from all or a subset of the at least 10 target loci by the methylated molecules for the at least one normalization locus.

In some embodiments, the subtracting background methylation comprises subtracting the number of methylated molecules as measured in the buffy coat from the number of methylated molecules in the cfDNA.

In some embodiments, the subtracting background methylation comprises subtracting the number of methylated molecules as measured in the buffy coat from the number of methylated molecules in the cfDNA on a per-locus basis.

In some embodiments, the filtering out selected hypermethylated target loci comprises filtering out target loci having a total number of methylated molecules in the buffy coat above a threshold.

In some embodiments, the threshold comprises a predetermined mean tumor methylated quantitative equivalent (QE), a predetermined max tumor methylated QE, or a combination thereof.

In some embodiments, the selected hypermethylated target loci comprise target loci having a hypermethylated cfDNA signal in non-cancer subjects.

In some embodiments, the filtering out selected hypermethylated target loci is performed prior to determining the number of methylated molecules in the sample.

In some embodiments, the subtracting background methylation is performed prior to determining the number of methylated molecules in the sample.

In some embodiments, the filtering out hypermethylated loci and the subtracting background methylation are performed prior to quantifying the number of methylated molecules in the sample.

In another aspect, this disclosure features a method of determining a DNA methylation profile in a subject over time, the method comprising: at a first time point: i) treating a sample isolated from the subject to encode the presence or absence of DNA methylation in DNA sequences, wherein the sample comprises at least ten target loci from the DNA sequences, wherein each locus of the at least ten target loci is chosen due to an expected increase in DNA methylation at each loci in cancerous tissue compared to non-cancerous tissue; ii) adding to the sample a set of synthetic molecules, the set of molecules comprising: target-associated regions having a nucleotide sequence that matches a target sequence region of an endogenous target molecule comprising at least one of the target loci, and variation regions with a nucleotide sequence that does not match a sequence region of an endogenous target molecule; iii) generating a co-amplification mixture comprising an amplified set of synthetic molecules and an amplified set of the at least ten target loci from the DNA sequences; iv) sequencing the co-amplification mixture at a read depth of at least one read sequence per molecule in the sample to generate sequence reads; v) determining a number of the sequence reads that are methylated sequence reads; vi) quantifying a number of methylated molecules in the sample based on the number of methylated sequence reads in the sample and a number of reads from the set of synthetic molecules; repeating steps one or more steps i) to vi) at a second time point; and determining the DNA methylation profile in the subject based on the number of methylated molecules in the sample at the first time point and the number of methylated molecules in the sample at the second time point.

In some embodiments, determining the DNA methylation profile identifies a change in the methylation profile from the first time point to the second time point.

In some embodiments, the change in methylation profile indicates change in a tumor in the subject.

In some embodiments, the change in the methylation profile is incorporated into a clinical recommendation for the subject.

In some embodiments, the method further comprises assigning the methylation profile a metric of: an increase, a decrease, or a no-change based on comparison to a significance threshold.

5. BRIEF DESCRIPTION OF THE SEVERAL VIEWS OF THE DRAWINGS

FIG. 2A shows total methylated molecules for technical replicates of lung cancer contrived samples at various tumor fractions (0% tumor, 0.5% tumor, 1% tumor, 2.5% tumor, and 5% tumor) using the lung cancer assay. 0.5% universal methylated and 5% universal methylated were controls.

Figure 2A:
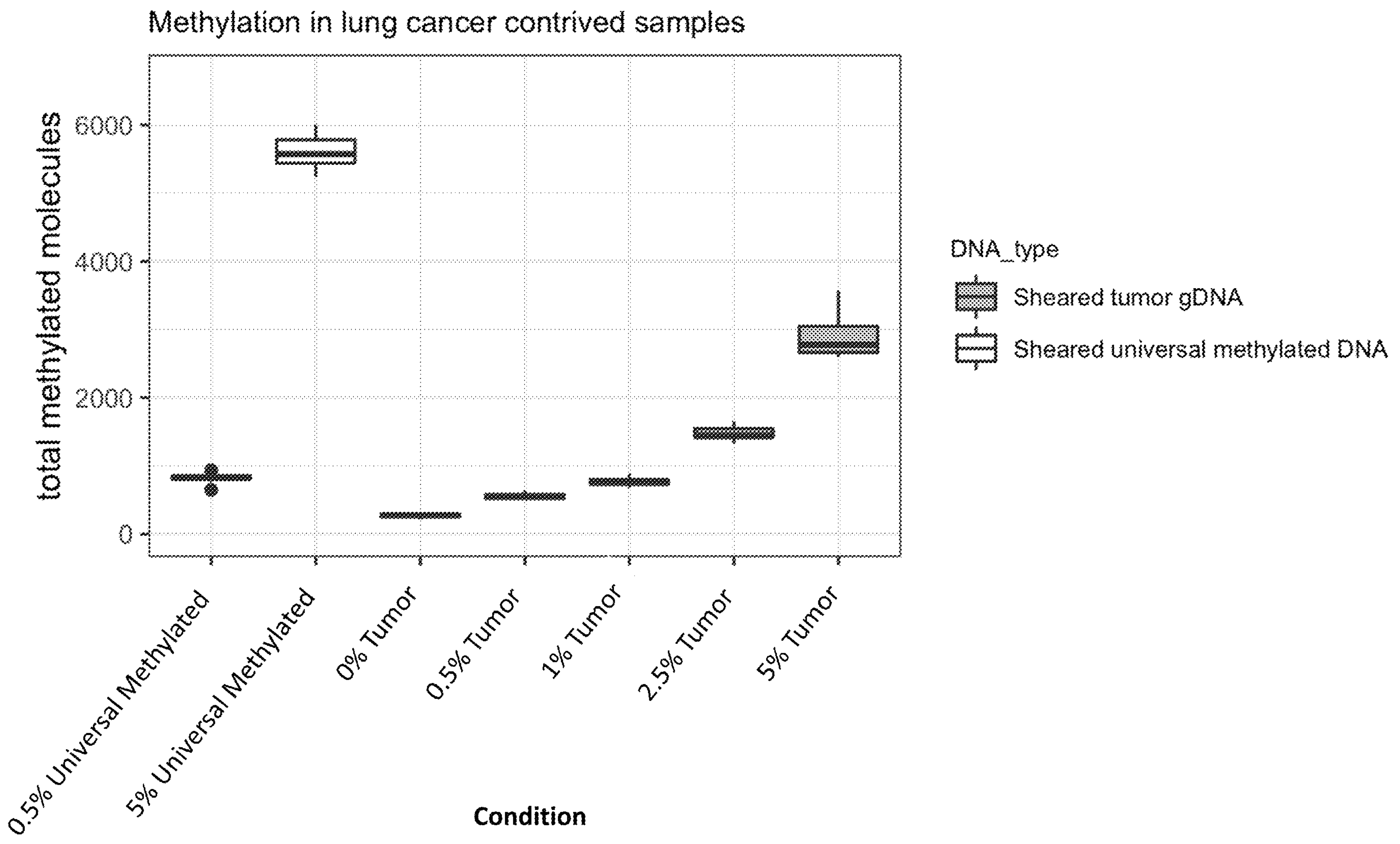
FIG. 2A shows data for the lung cancer detection assay.
Figure 2B:
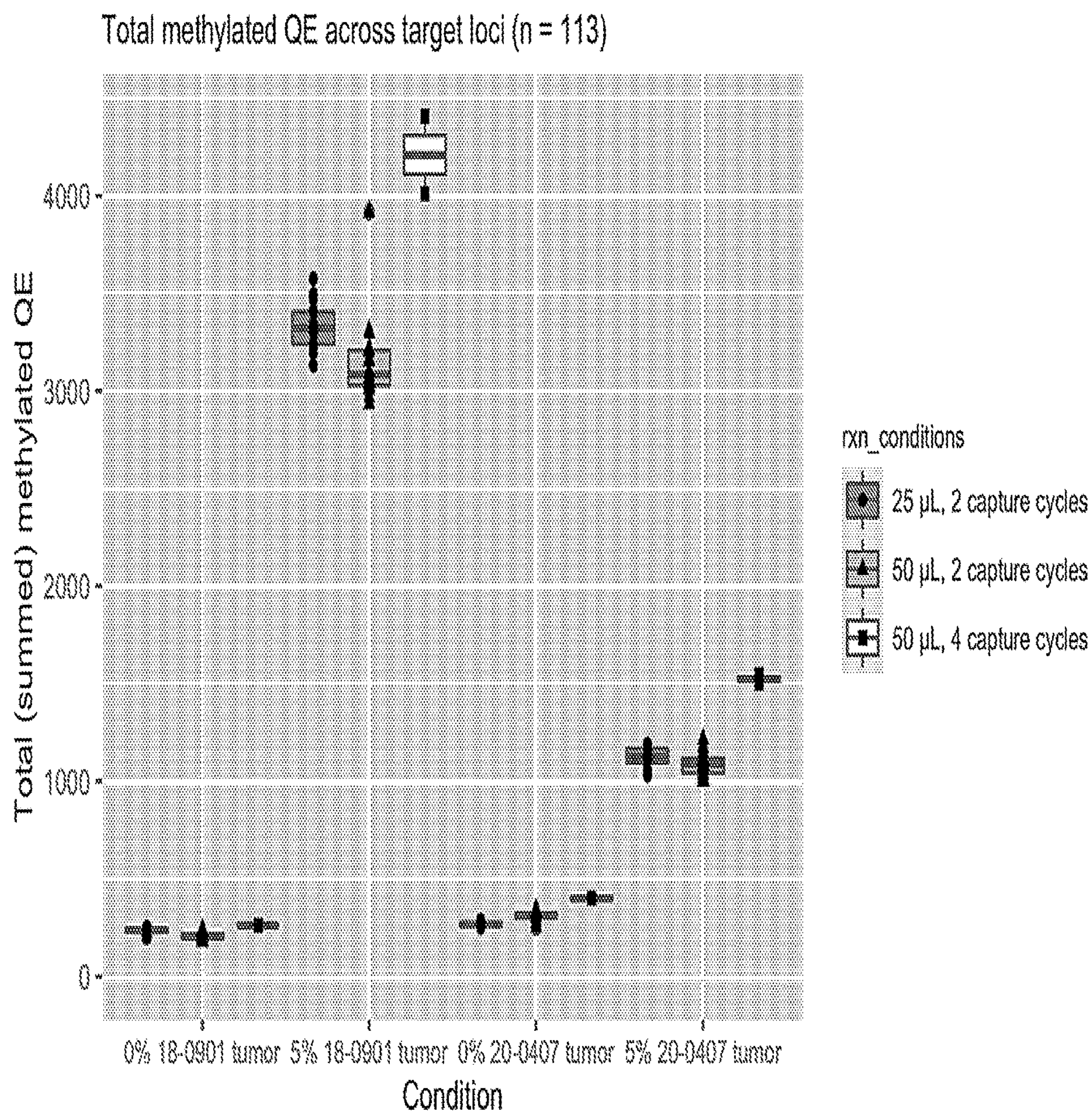

FIG. 2B shows data for the lung cancer detection assay in contrived samples from two different lung cancer subjects. FIG. 2B shows total (summed) methylated QE across target loci (n=113). Contrived samples were taken from subjects 18-0901 and 20-0407. Contrived samples were assayed at a 0% tumor fraction and a 5% tumor fraction using the PCR volumes and thermal cycler protocols indicated in FIG. 2B.

Figure 3:
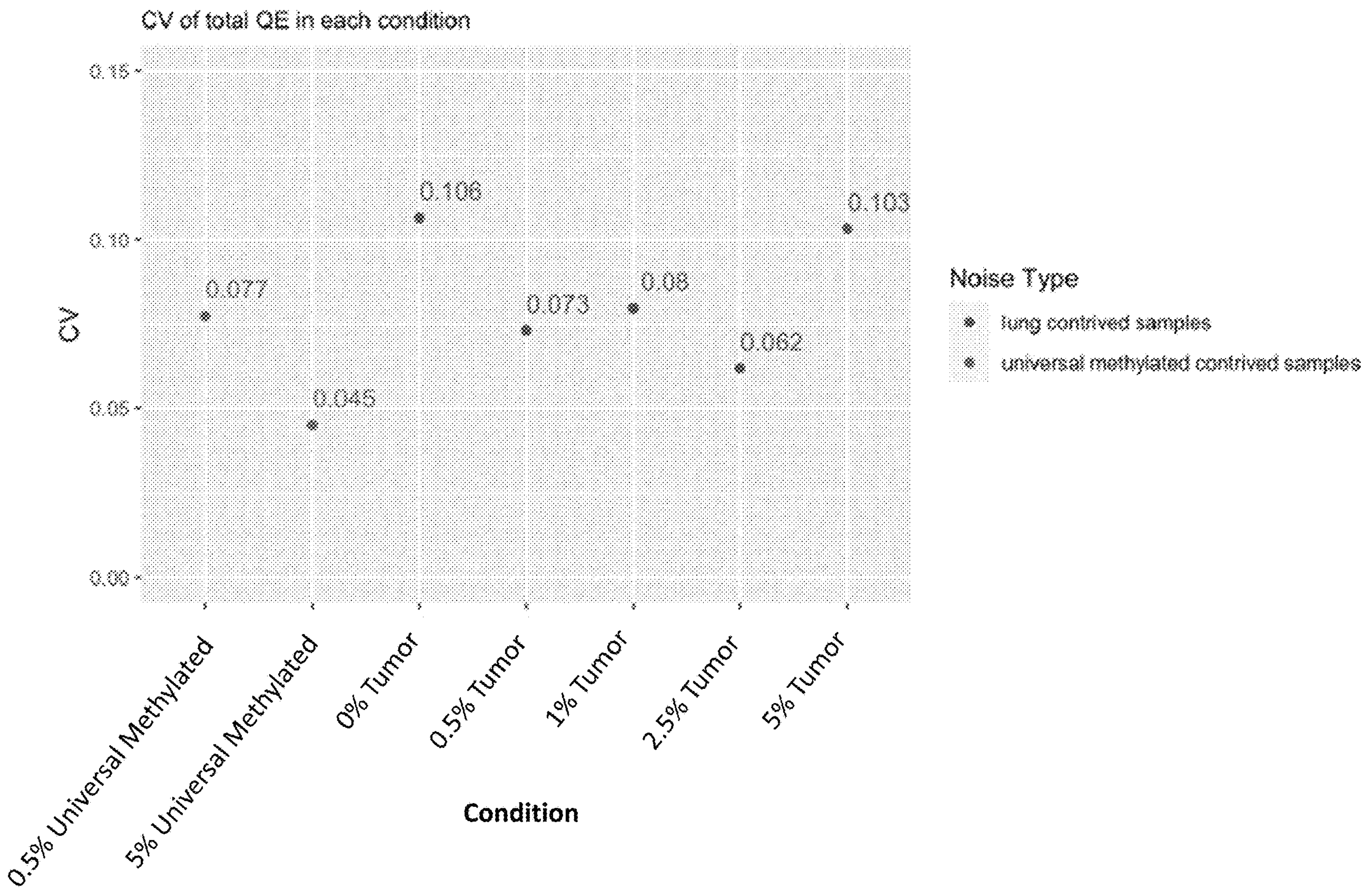

FIG. 3 shows concordance values of total QE for each of the samples analyzed in FIG. 2A.

Figure 4:
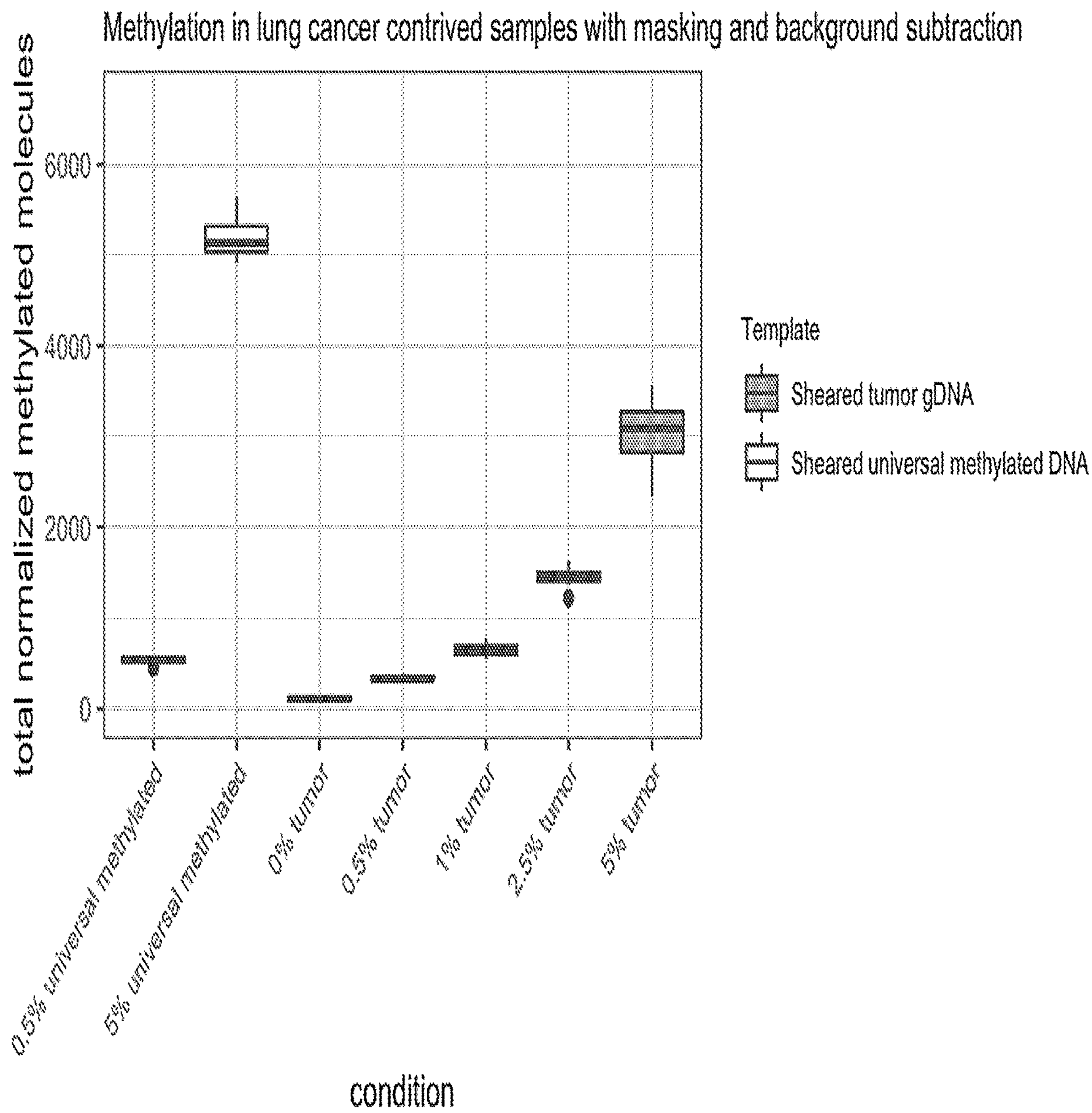

FIG. 4 shows methylation in lung cancer contrived samples with masking and background subtraction for each of the samples analyzed in and FIG. 3. FIG. 4 shows total normalized methylated molecules (y-axis) over the lung cancer contrived samples at various tumor fractions (0% tumor, 0.5% tumor, 1% tumor, 2.5% tumor, and 5% tumor) and controls: 0.5% universal methylated and 5% universal methylated were controls. The data is shown with background subtraction and masking of target loci with high background methylation.

Figure 5:
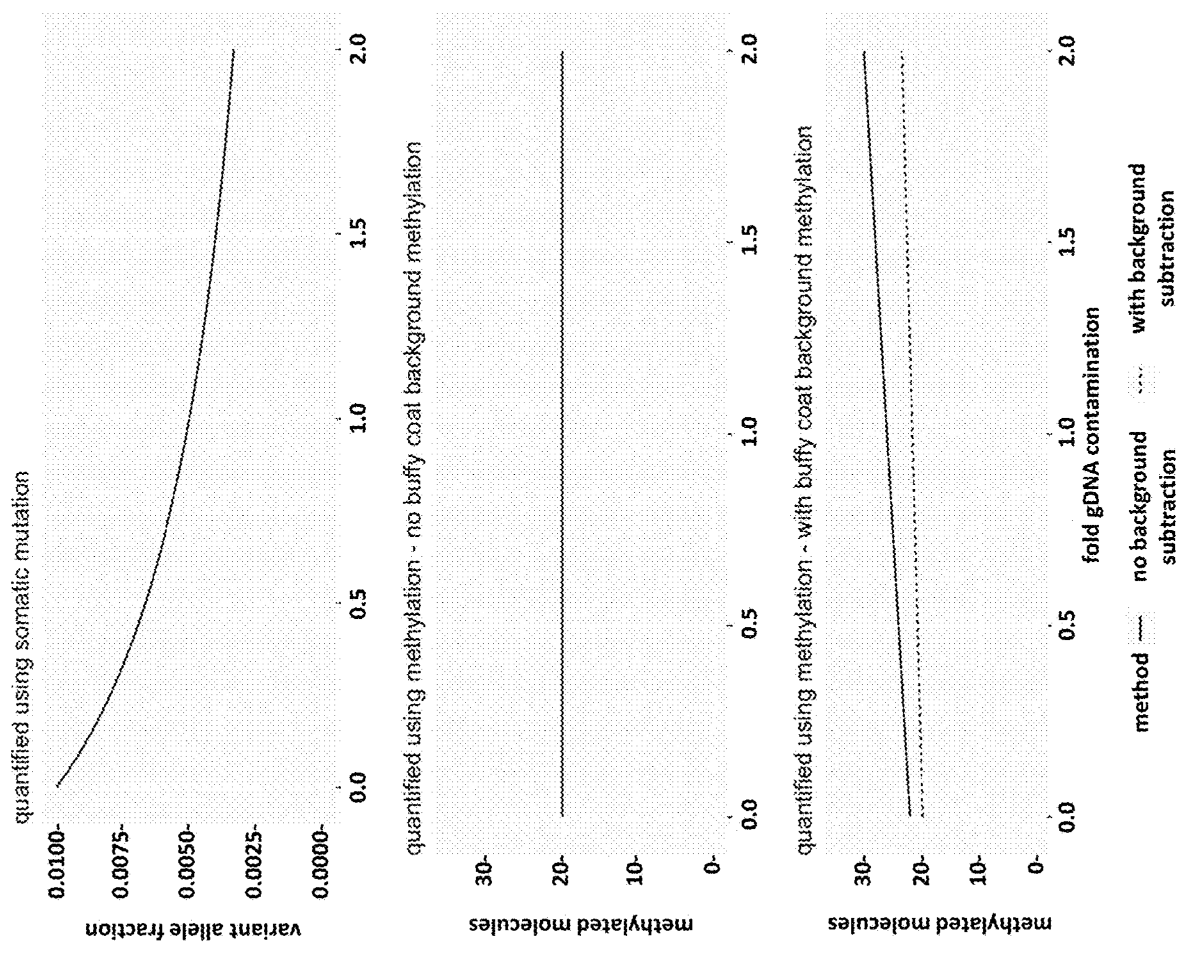

FIG. 5 shows data from simulations of cfDNA tumor signals quantified using somatic mutations and methylation approaches. Top panel shows variant allele fraction (y-axis) over fold gDNA contamination (x-axis)quantified using somatic mutation. Middle panel shows methylated molecules (y-axis) over fold gDNA contamination (x-axis) quantified using methylation with no buffy coat background methylation. Bottom panel shows methylated molecules (y-axis) over fold gDNA contamination (x-axis) quantified using methylation with buffy coat background methylation.

Figure 6:
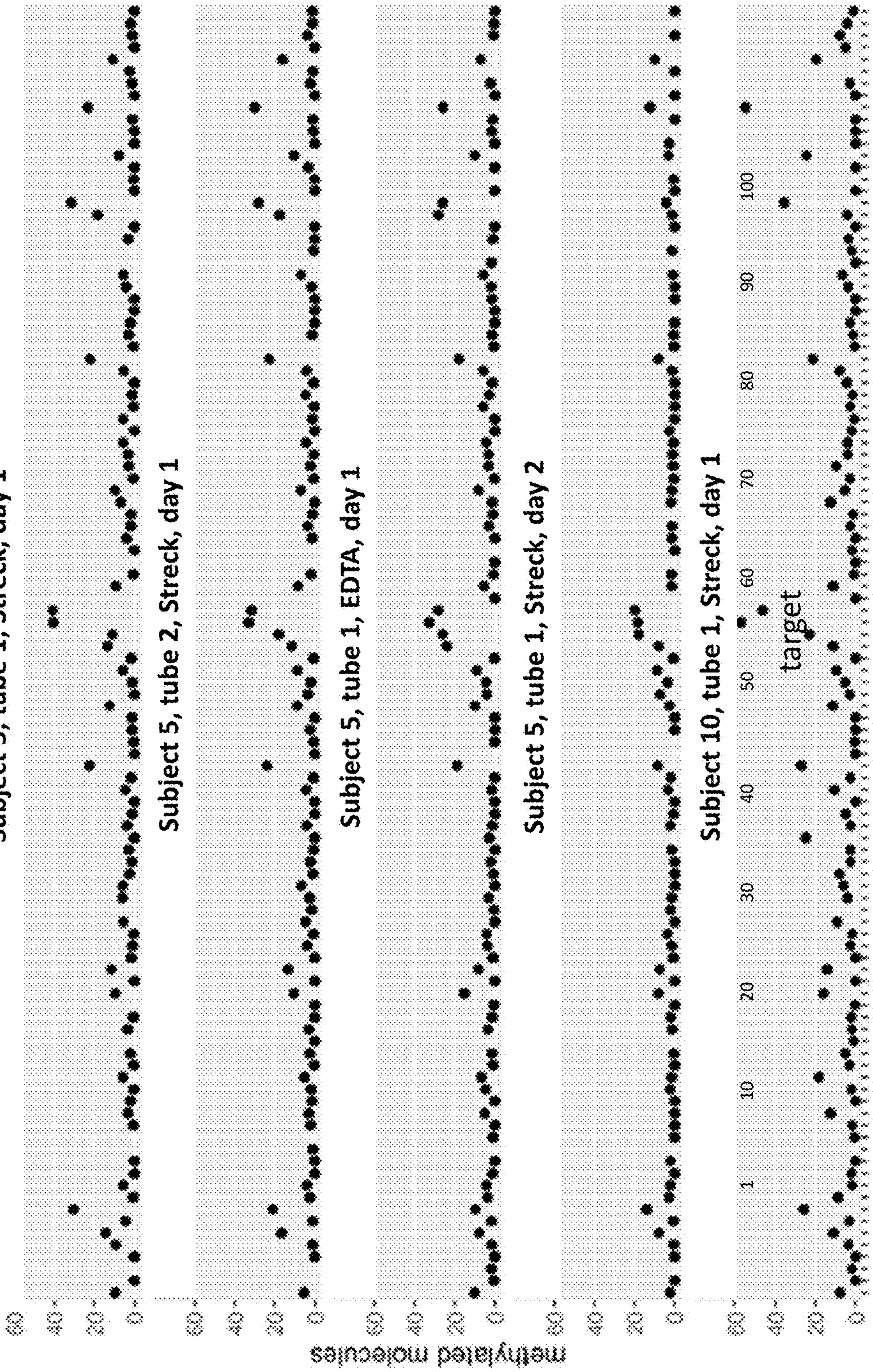

FIG. 6 shows methylation profiles for buffy coats (i.e., 5000 genomic equivalents (g.e.) of buffy coat) isolated from different tubes of the same blood draw, different tube types, different days, and different subjects. Data shown as methylated molecules (y-axis) for different buffy coats (x-axis).

Figure 7:
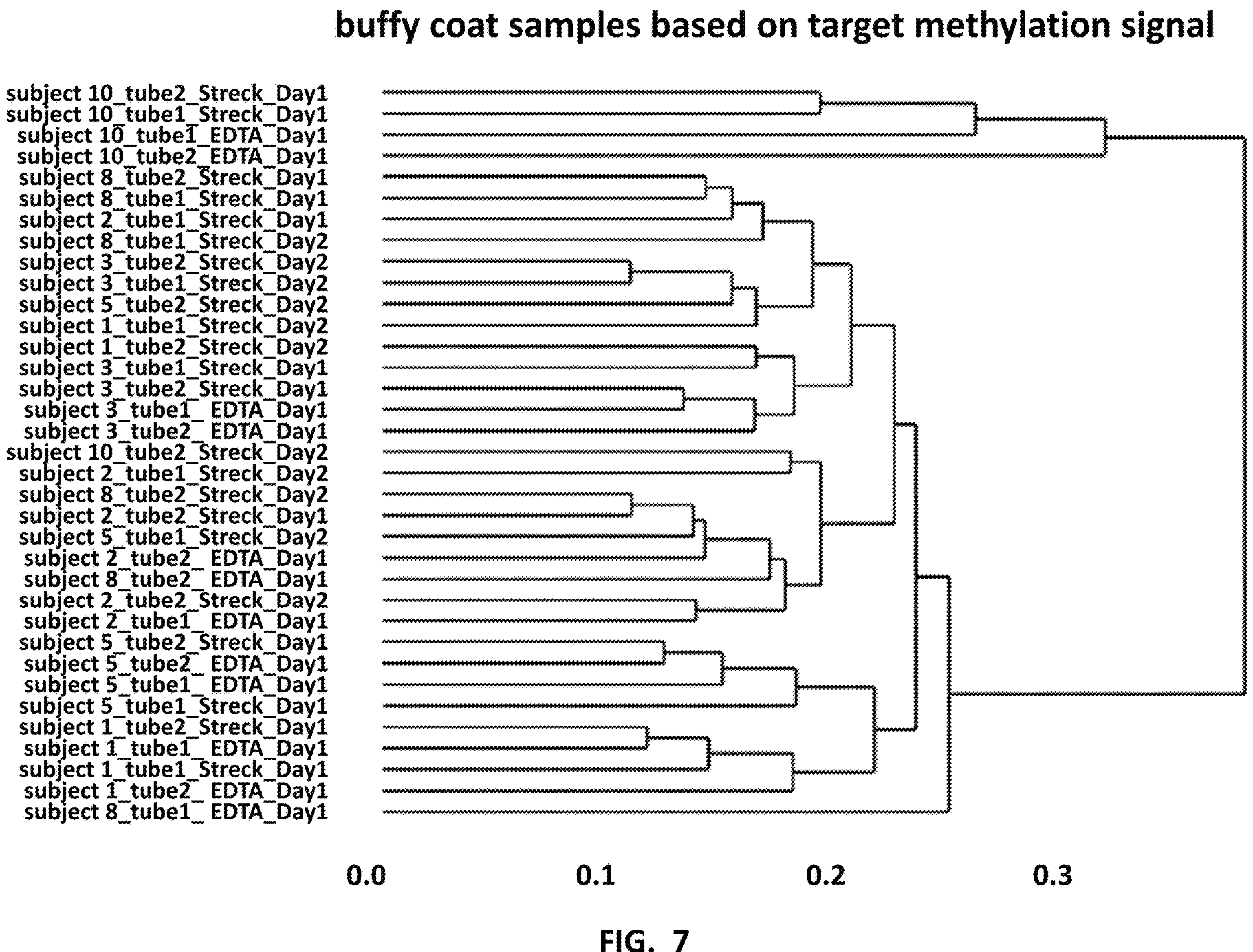

FIG. 7 shows hierarchical clustering of methylation profiles for buffy coats i.e., 5000 g.e. of buffy coat) isolated from different tubes of the same blood draw, different tube types, different days, and different subjects. Cluster distance was calculated using the L1 norm.

Figure 8:
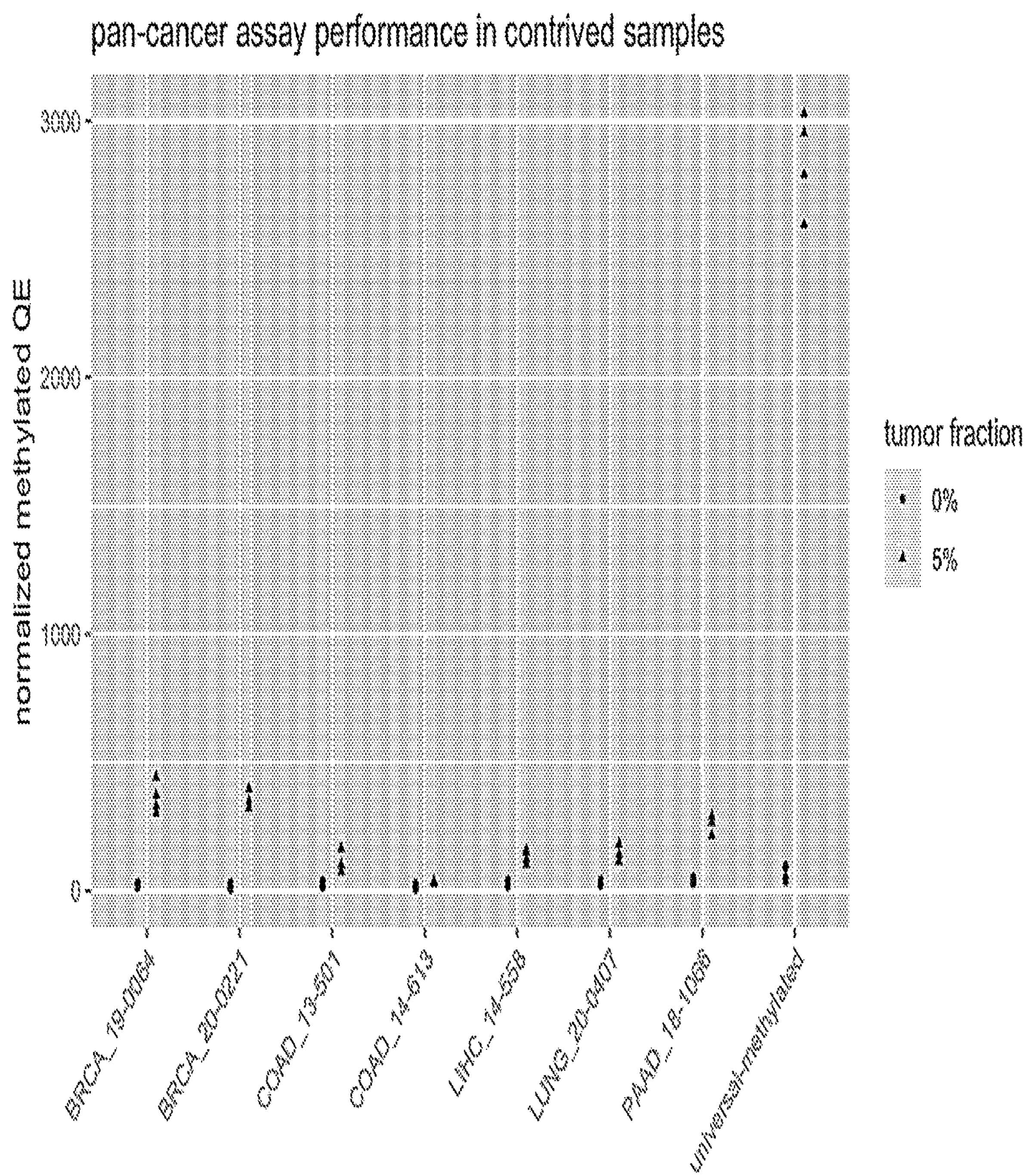

FIG. 8 shows data for pan-cancer assay performance in contrived samples. Data is presented as normalized methylated QE (y-axis) for each contrived samples from different cancer types. Contrived samples were prepared at 0% tumor fraction and 5% tumor fraction.

Figure 9A:
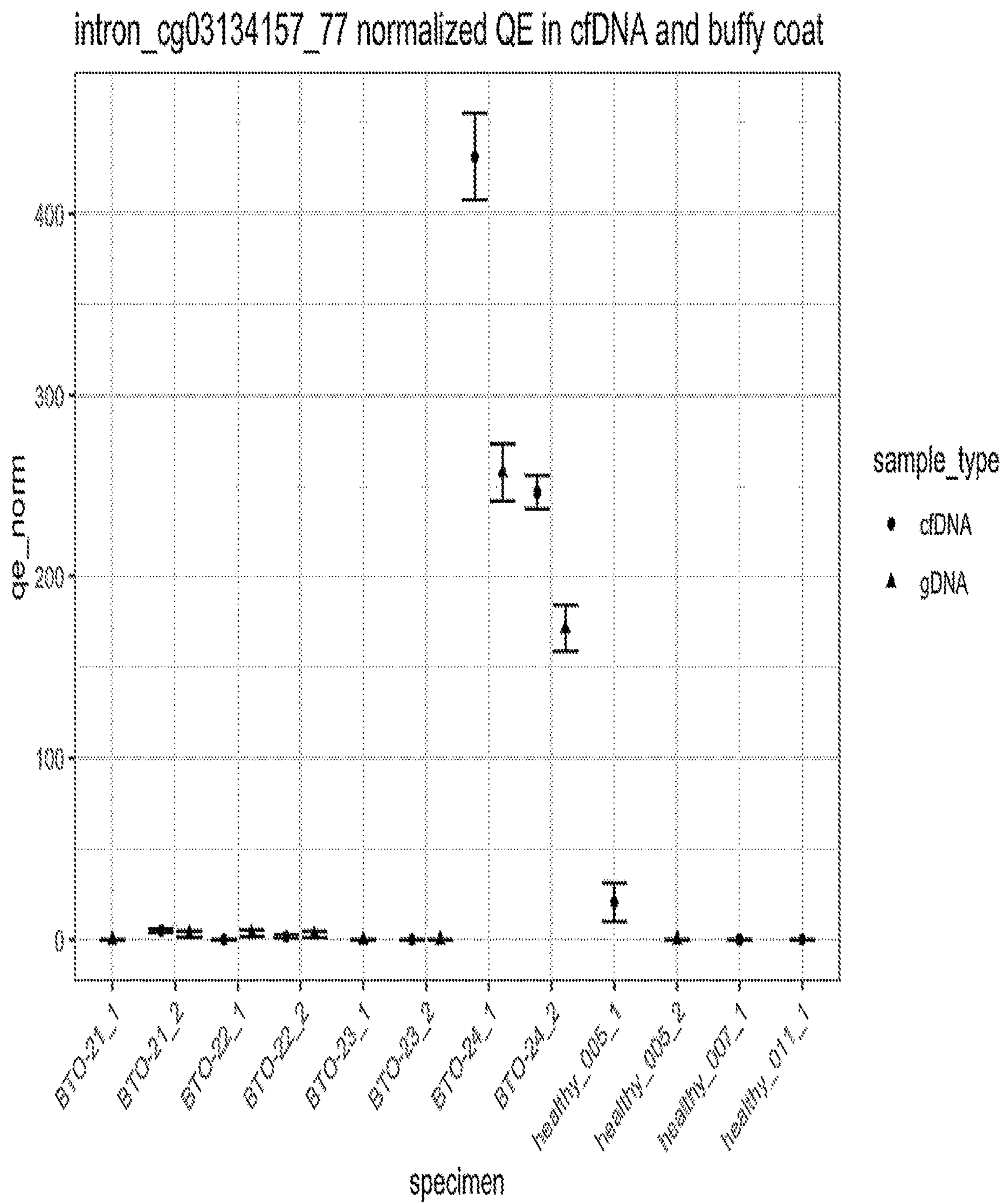
Figure 9B:
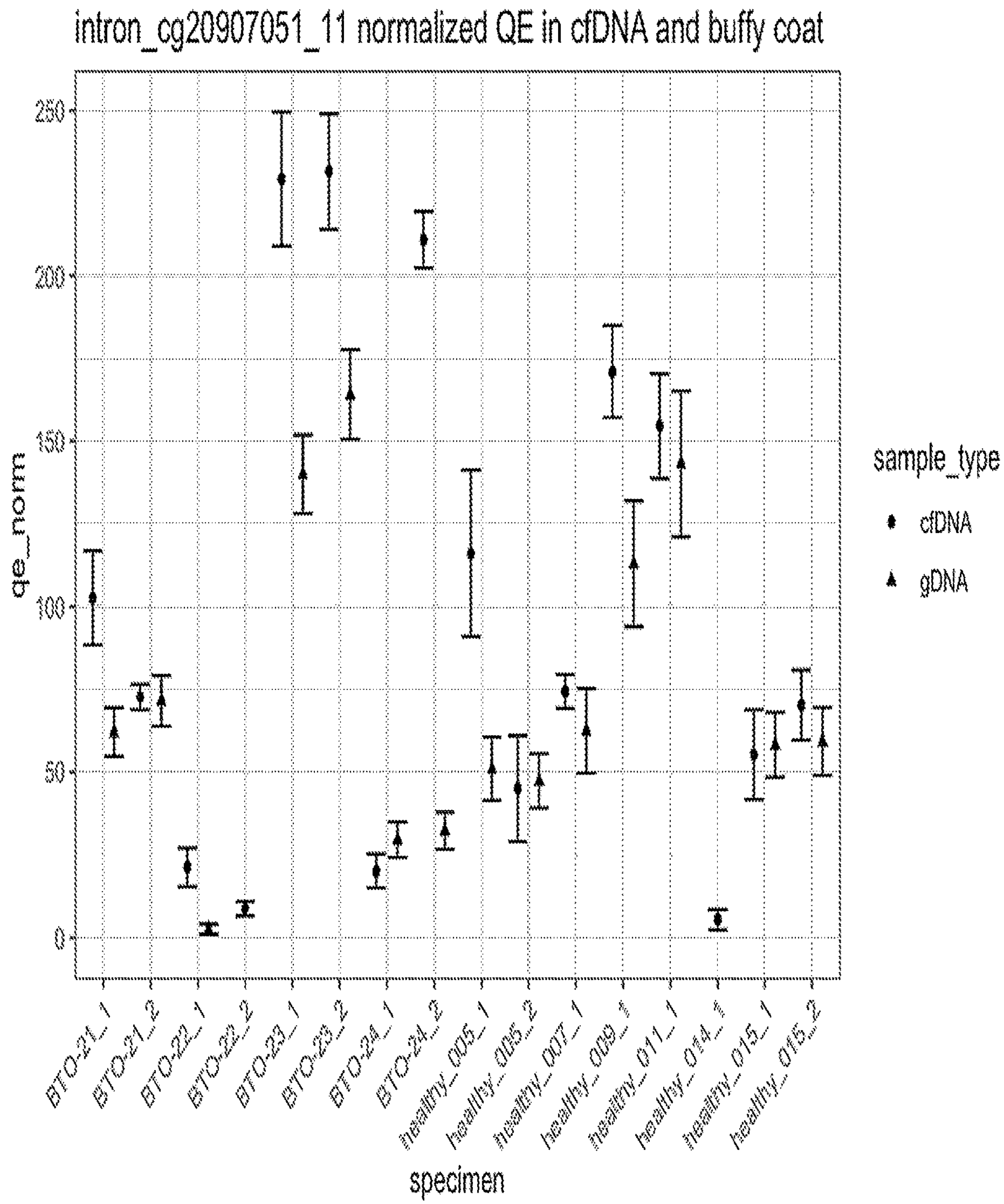
Figure 9C:
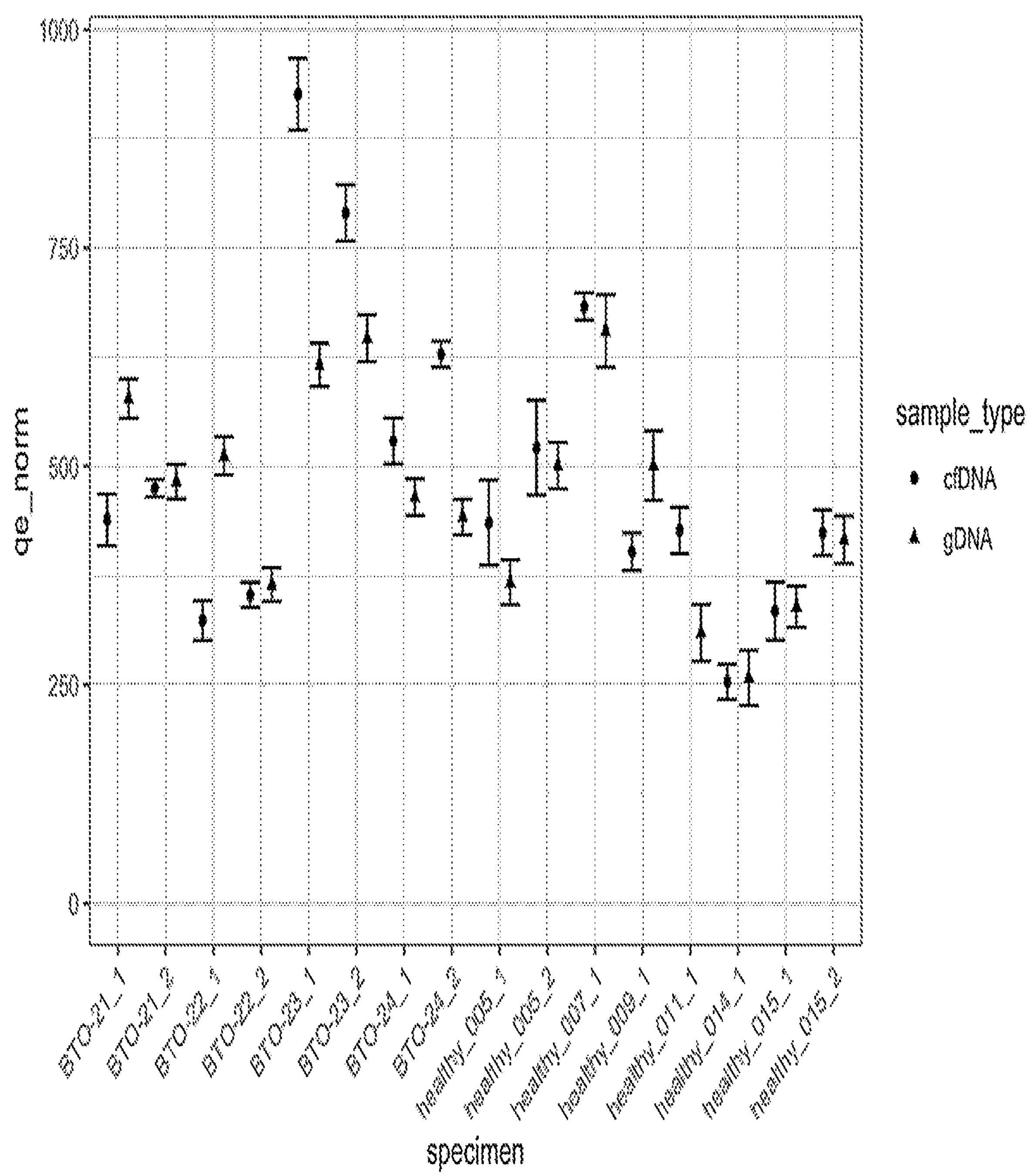
Figure 9D:
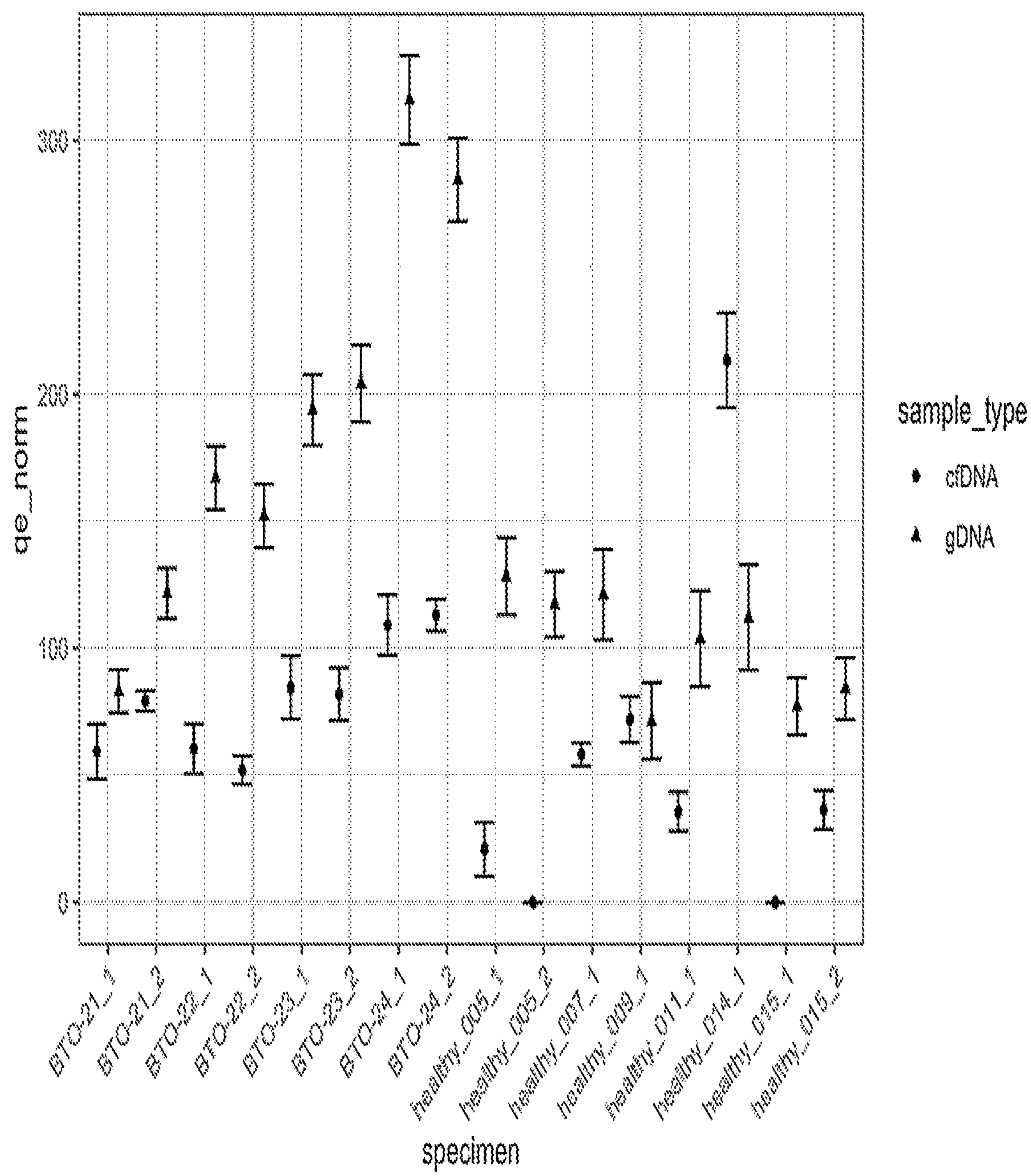
Figure 9E:
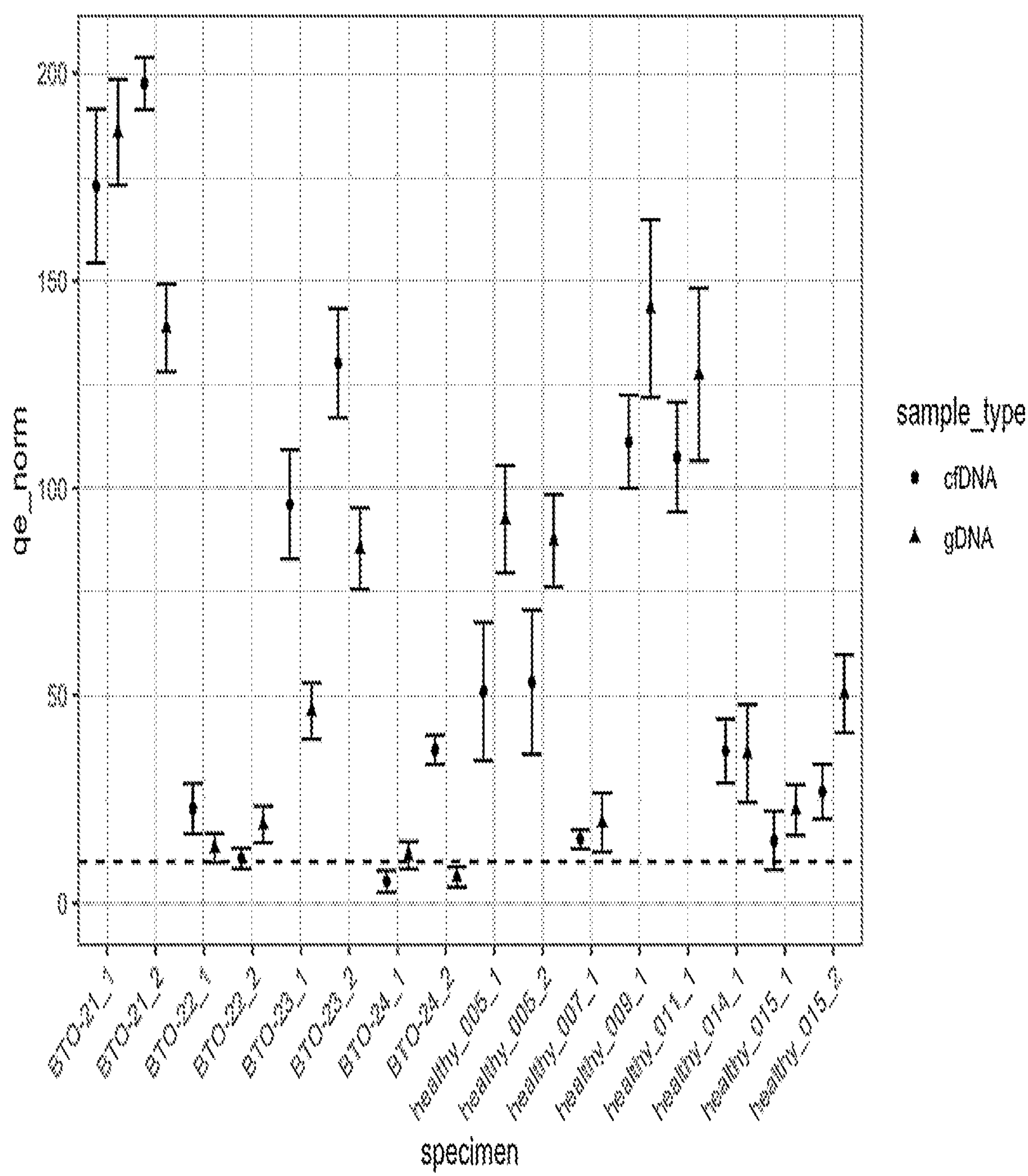
Figure 9F:
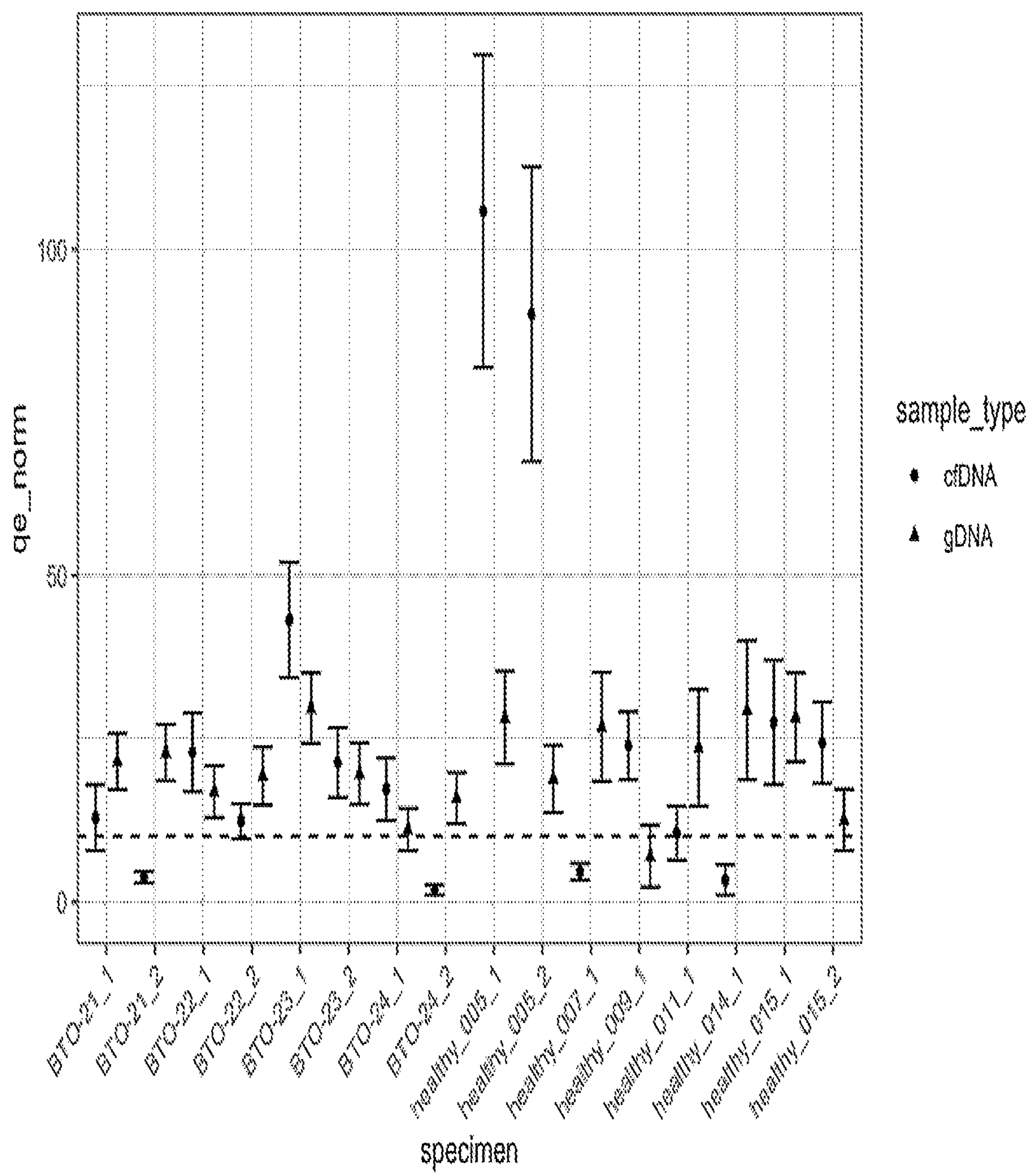

FIGS. 9A-9F show data for non-limiting examples of loci used in a "personalized blacklist." Data is presented as Tumor QE normalized (y-axis: "qe_norm") for each of the 12 samples indicated on the x-axis in cfDNA and buffy coat. FIG. 9A shows tumor QE (normalized) for the intron cg03134157_77. FIG. 9B shows tumor QE (normalized) for the intron cg20907051_11. FIG. 9C shows tumor QE (normalized) for the intron_cg12880300_0. FIG. 9D shows tumor QE (normalized) for the locus IRX4_cg13974394_0. FIG. 9E shows tumor QE (normalized) for the locus EMID2_cg25290307_0. FIG. 9F shows tumor QE (normalized) for intron_cg11453719_0.

Figure 10:
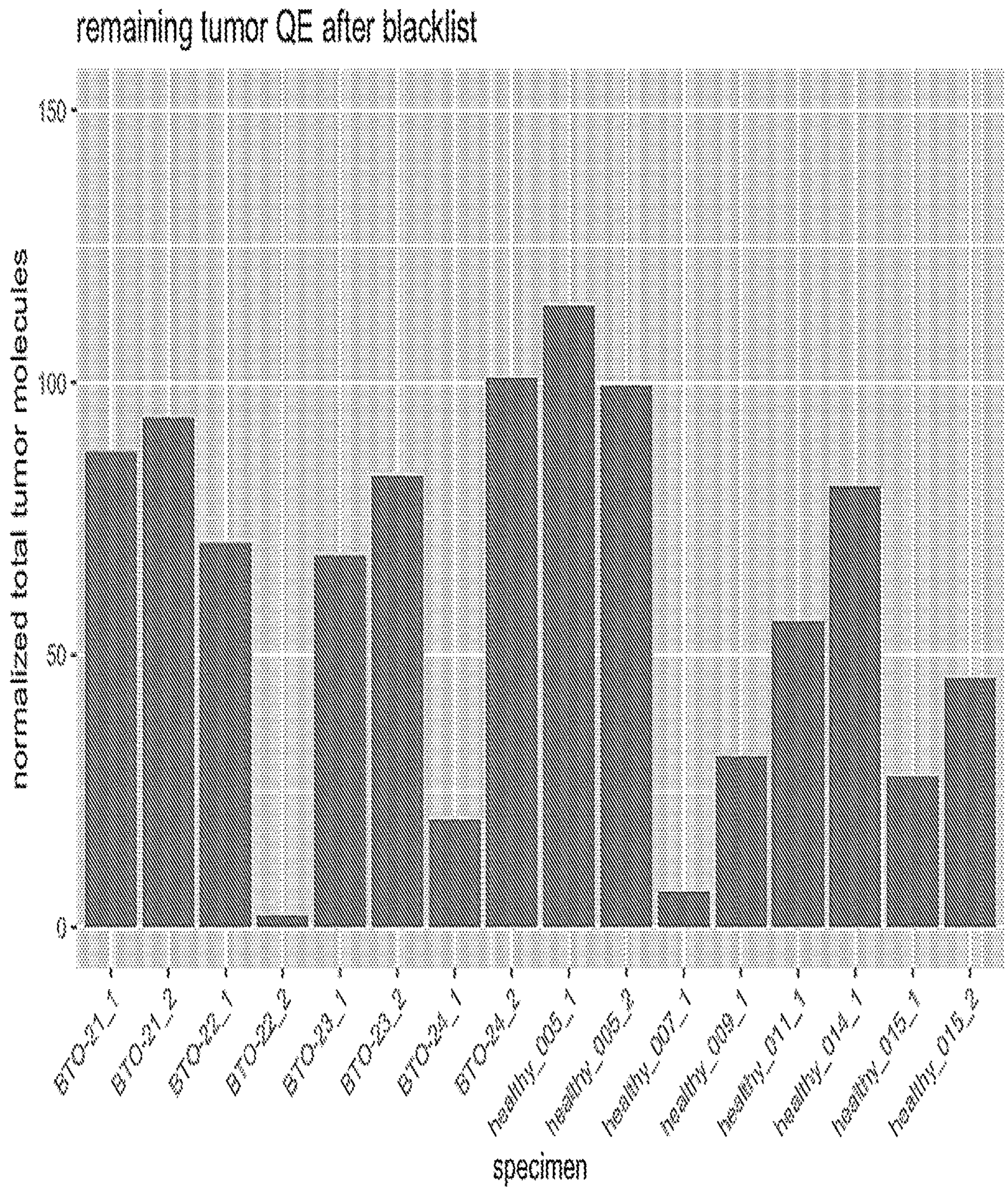

FIG. 10 shows normalized total tumor molecules (y-axis) for the specimens on the x-axis based on the global blacklist thresholds described herein (e.g., (1) max tumor QE in any non-cancer specimen>15; and (2) mean tumor QE (including 0s)>2).

Figure 11:
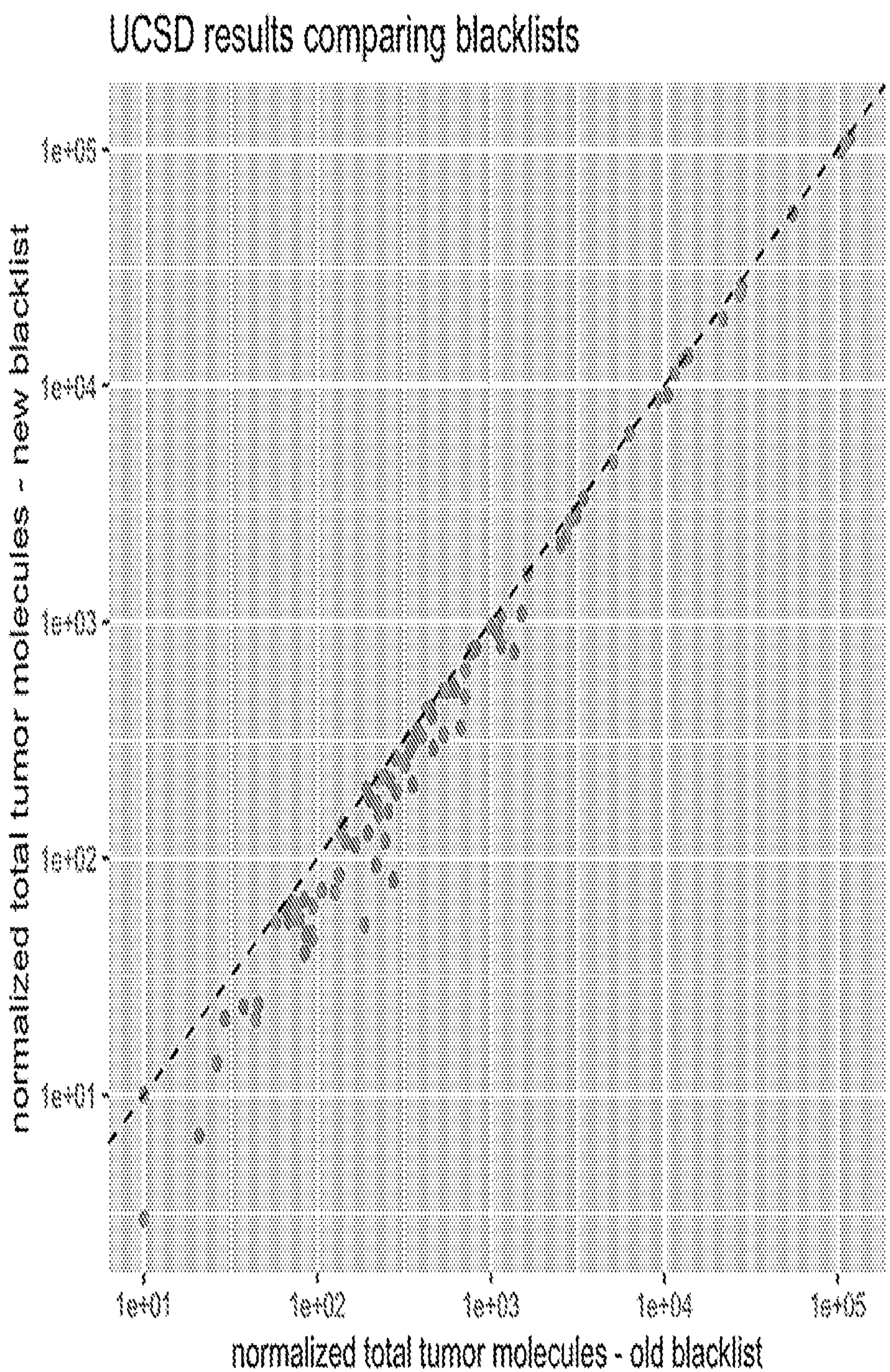

FIG. 11 shows normalized total tumor molecules for the new blacklist (y-axis) compared to the normalized total tumor molecules for the old blacklist. Each blacklist was applied to methylation data for the 30 subjects listed in FIG. 11 and plotted in the graph.

Figure 12A:
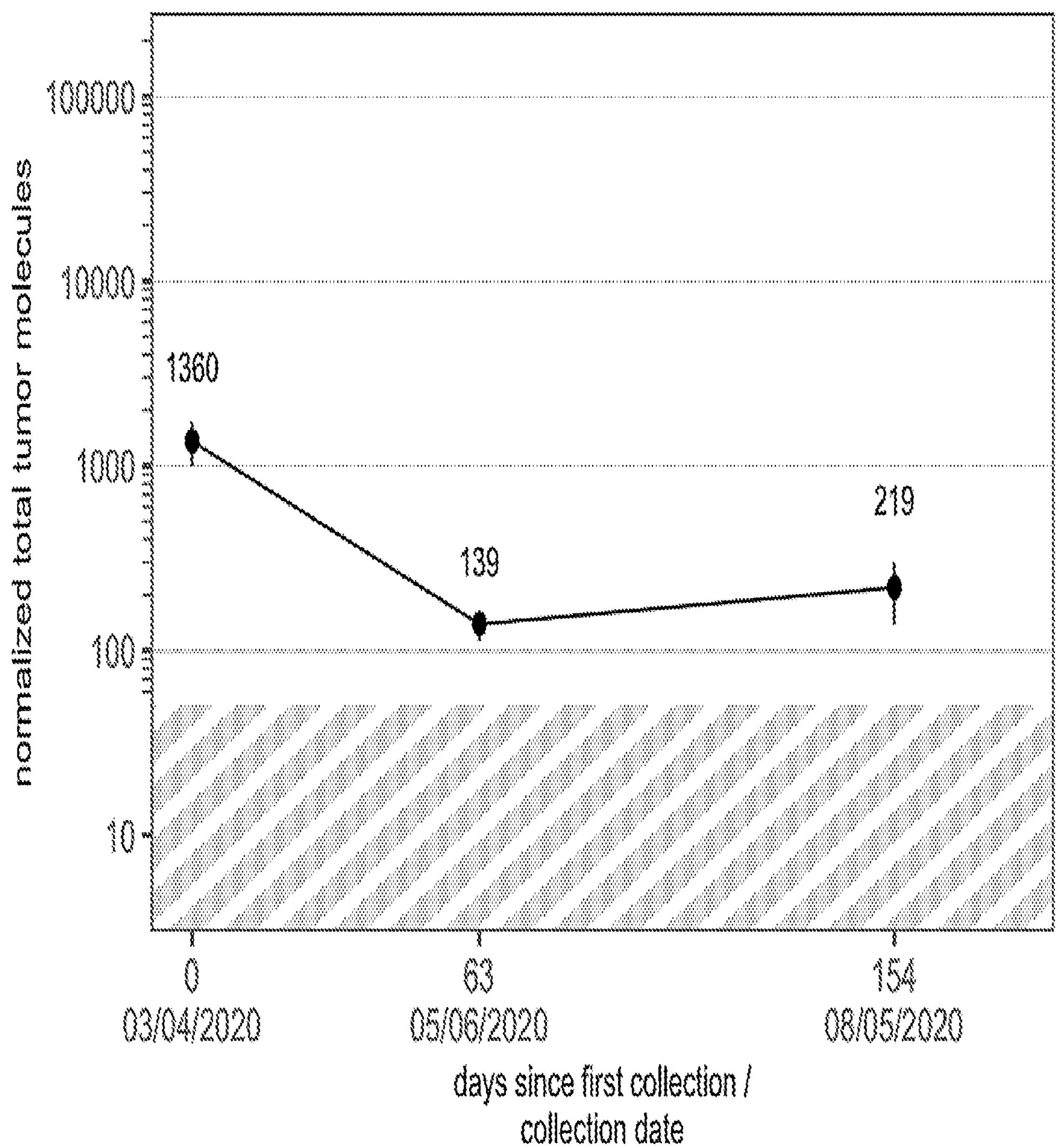
Figure 12B:
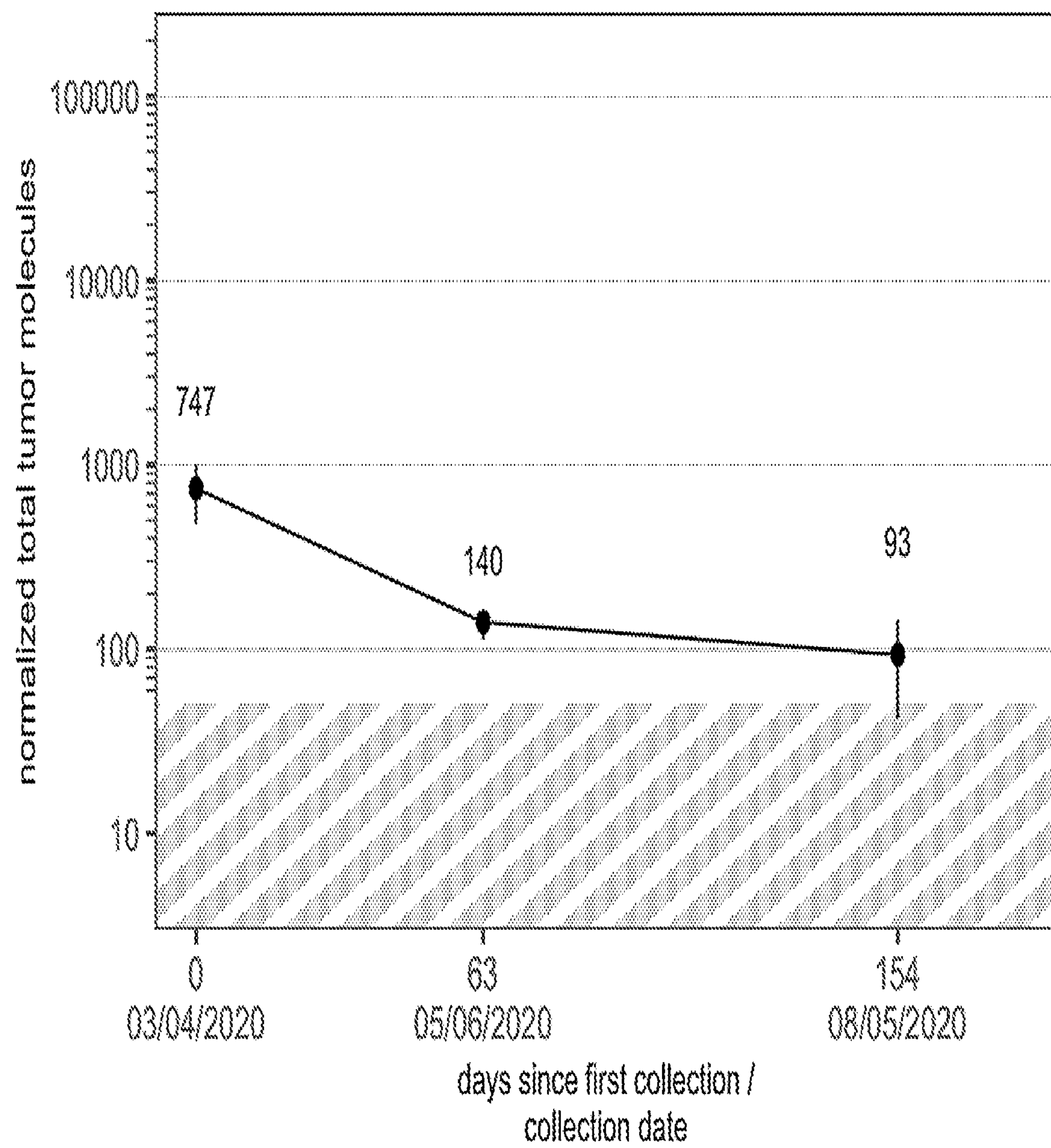
Figure 12C:
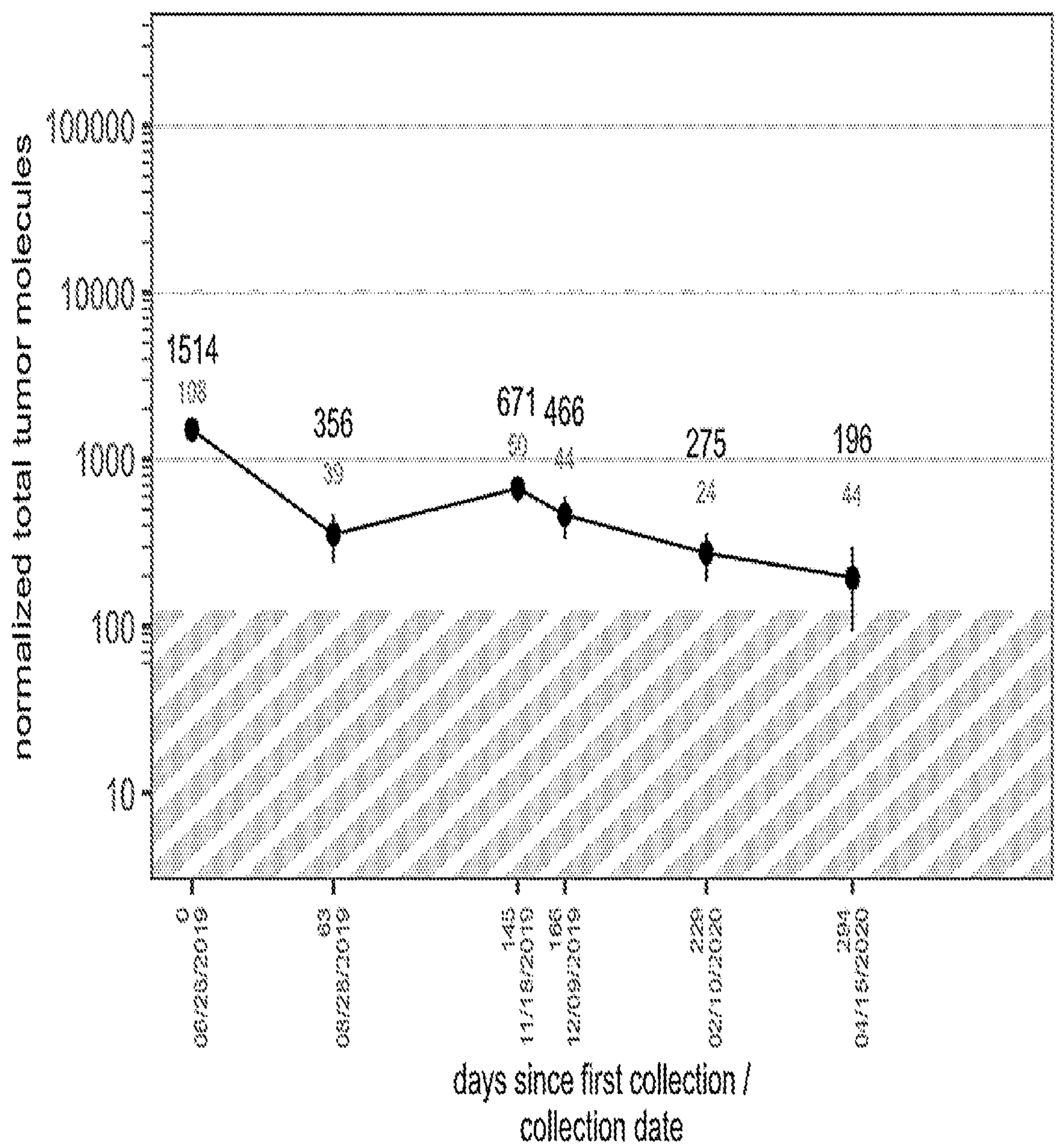
Figure 12D:
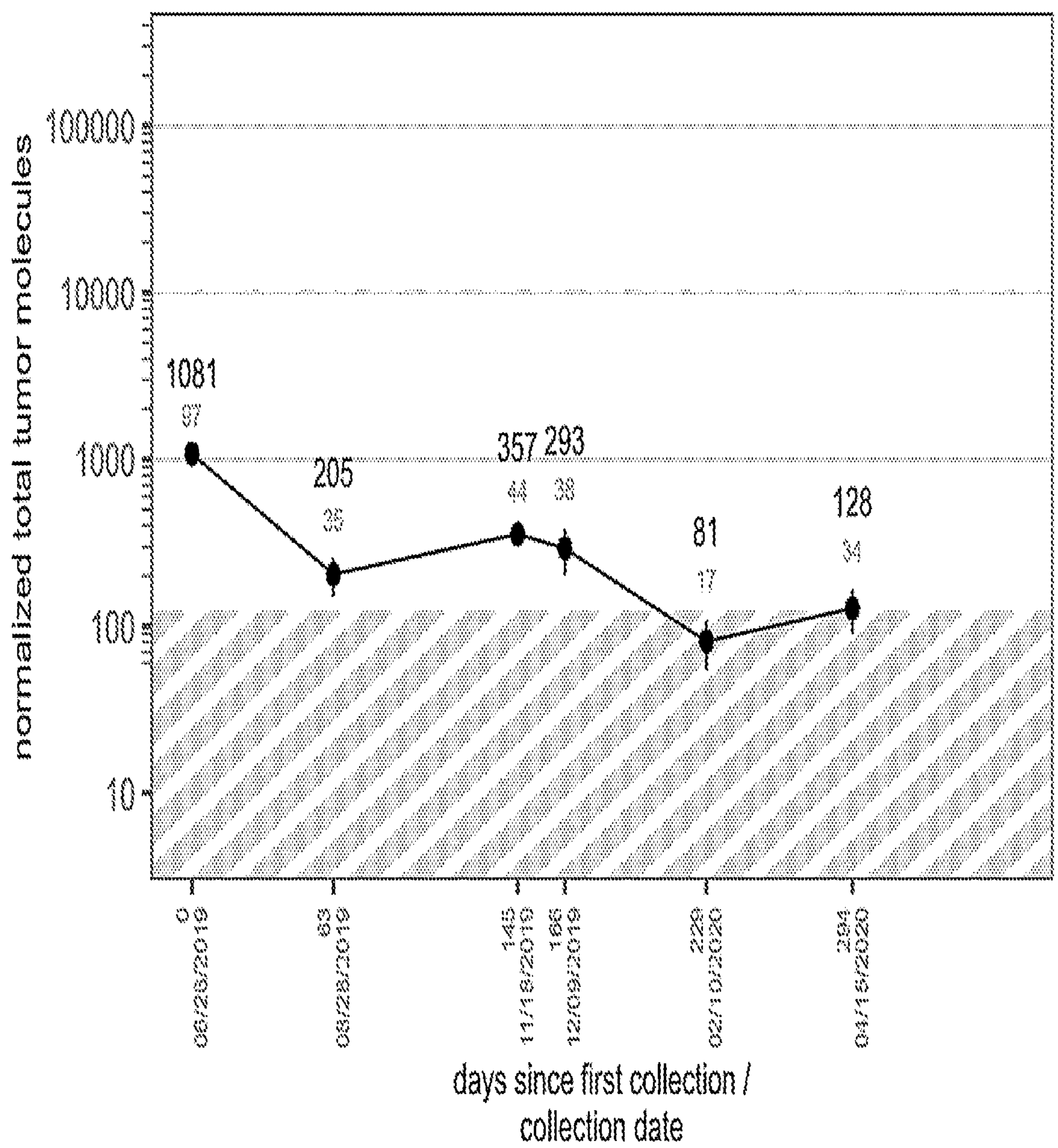
Figure 13B:
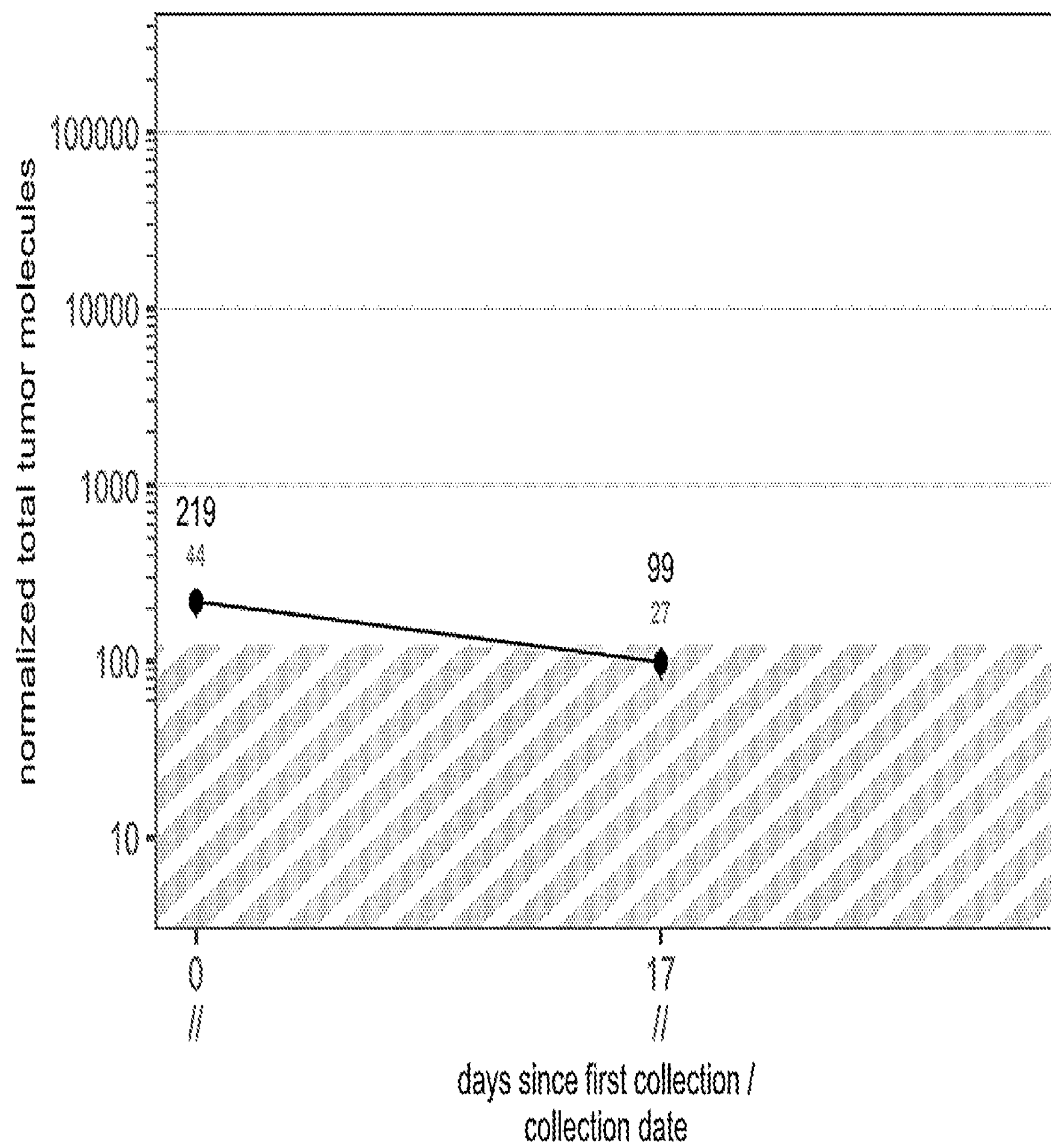
Figure 13C:
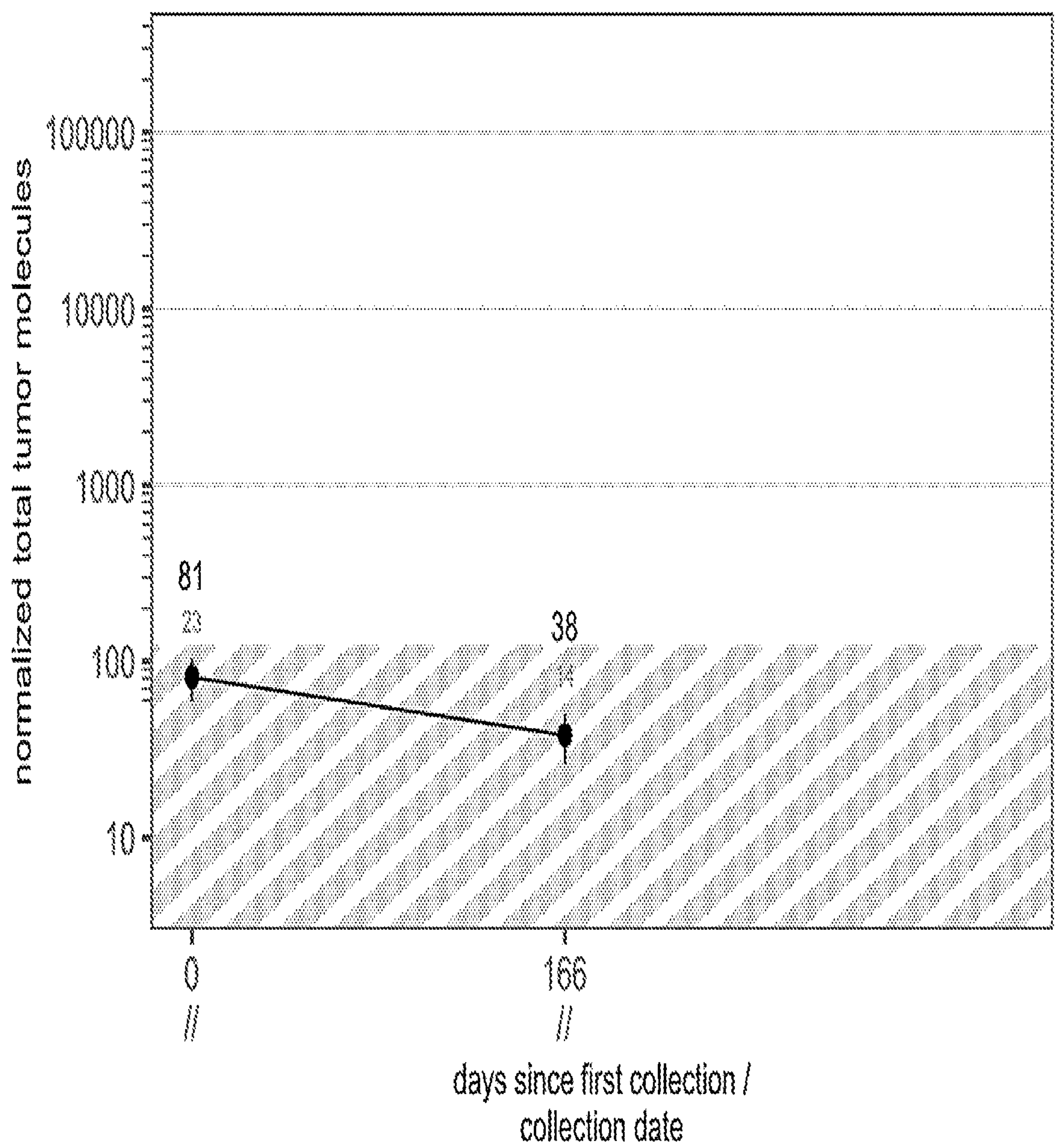
Figure 13D:
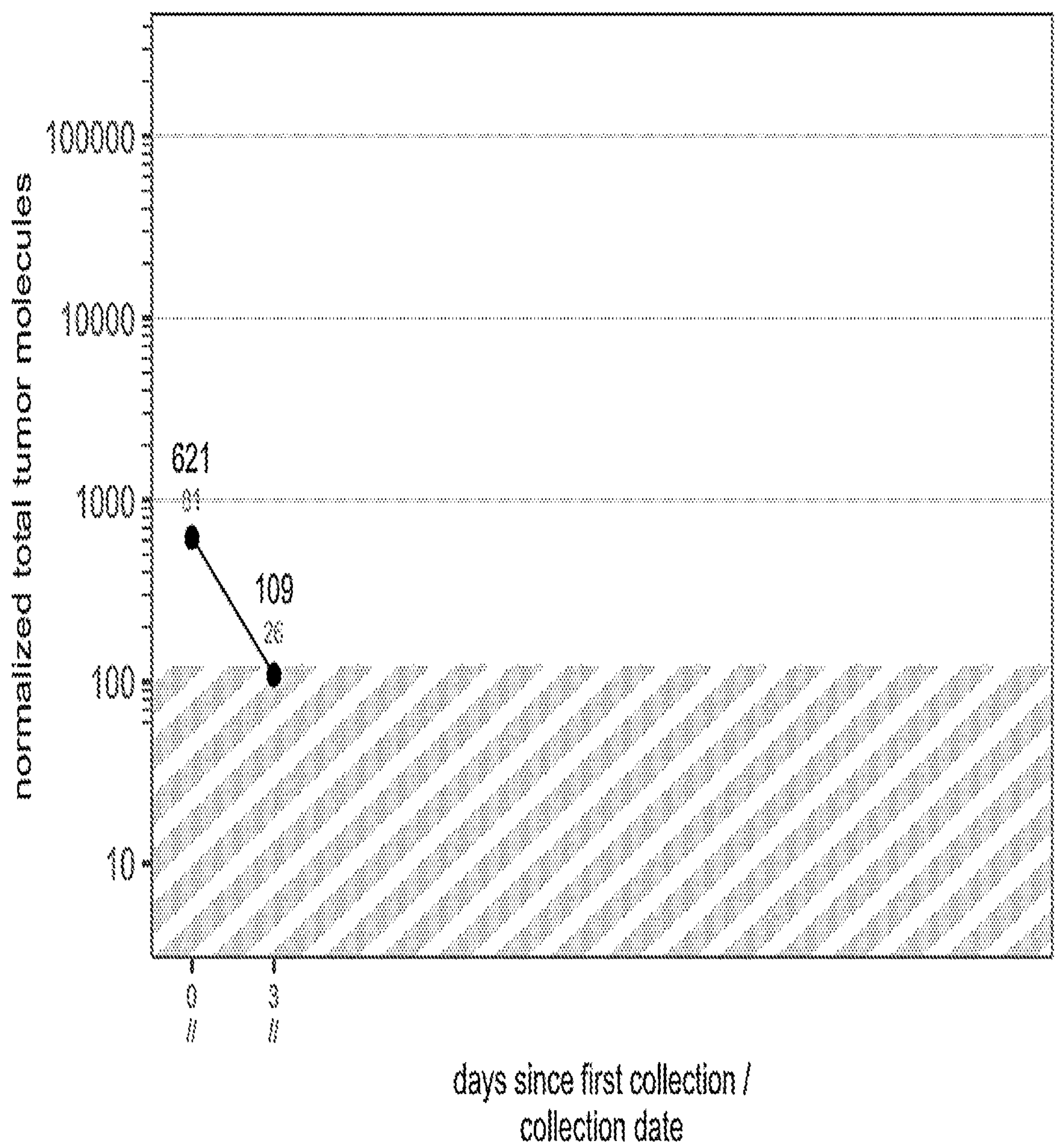
Figure 13E:
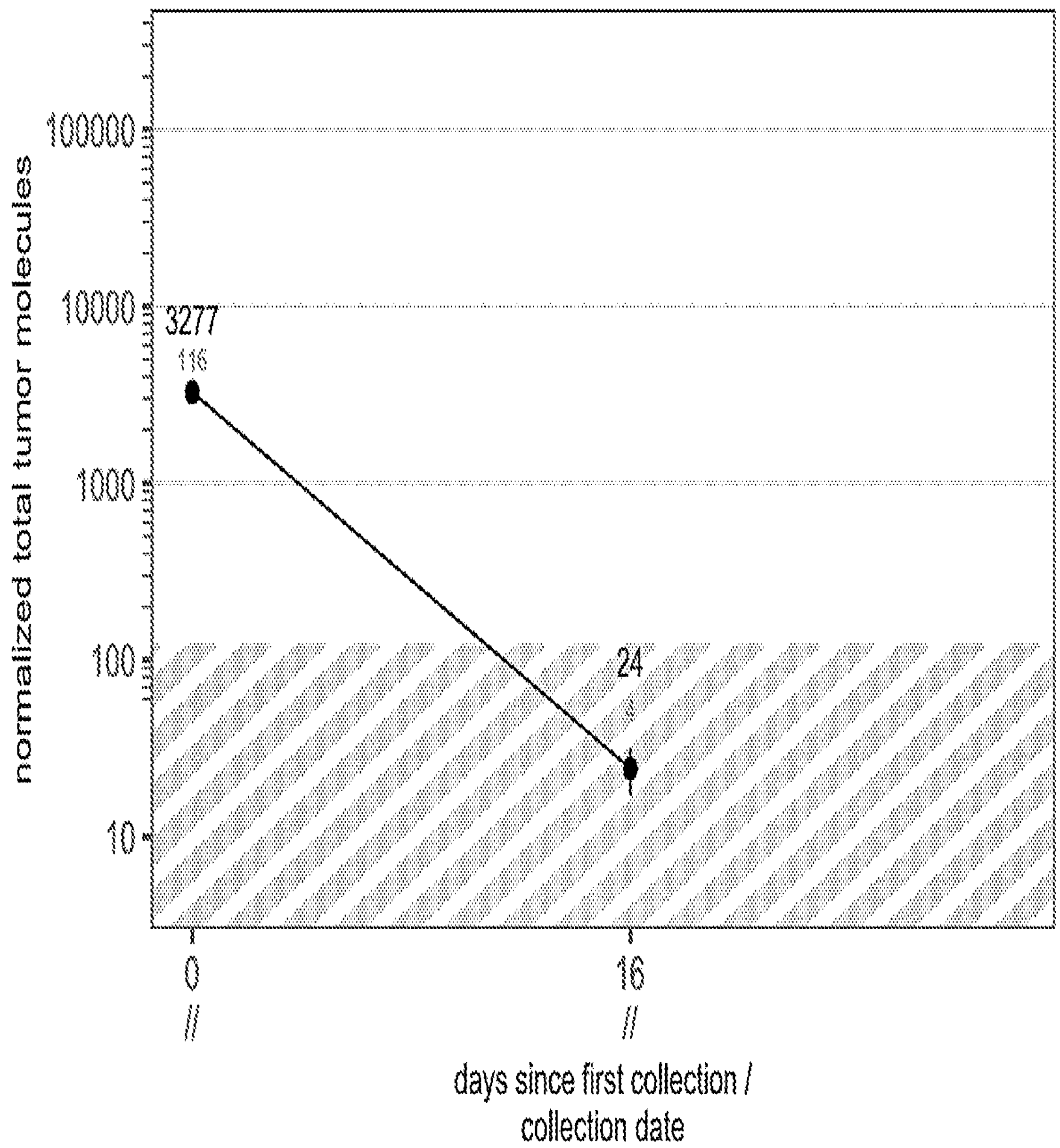

FIGS. 12A-12D show data for 2 subjects (out of 30), Subject 8272 and Subject 6885, that had slightly different methylation results after applying the new blacklist. Data is presented as normalized total tumor molecules (y-axis) for day 0, 63, and 154 since first collection. FIG. 12A shows data for Subject 8272 using old blacklist. FIG. 12B shows data for Subject 8272 using new blacklist. FIG. 12C shows data for Subject 6885 using old blacklist. FIG. 12D shows data for Subject 6885 using new blacklist.

FIGS. 13A-13E show data for 5 subjects (i.e., BTO-1 (FIG. 13A), BTO-2 (FIG. 13B), BTO-3 (FIG. 13C), BTO-4 (FIG. 13D), and BTO-5 (FIG. 13E)) generated using the new global blacklist.

Figure 14:
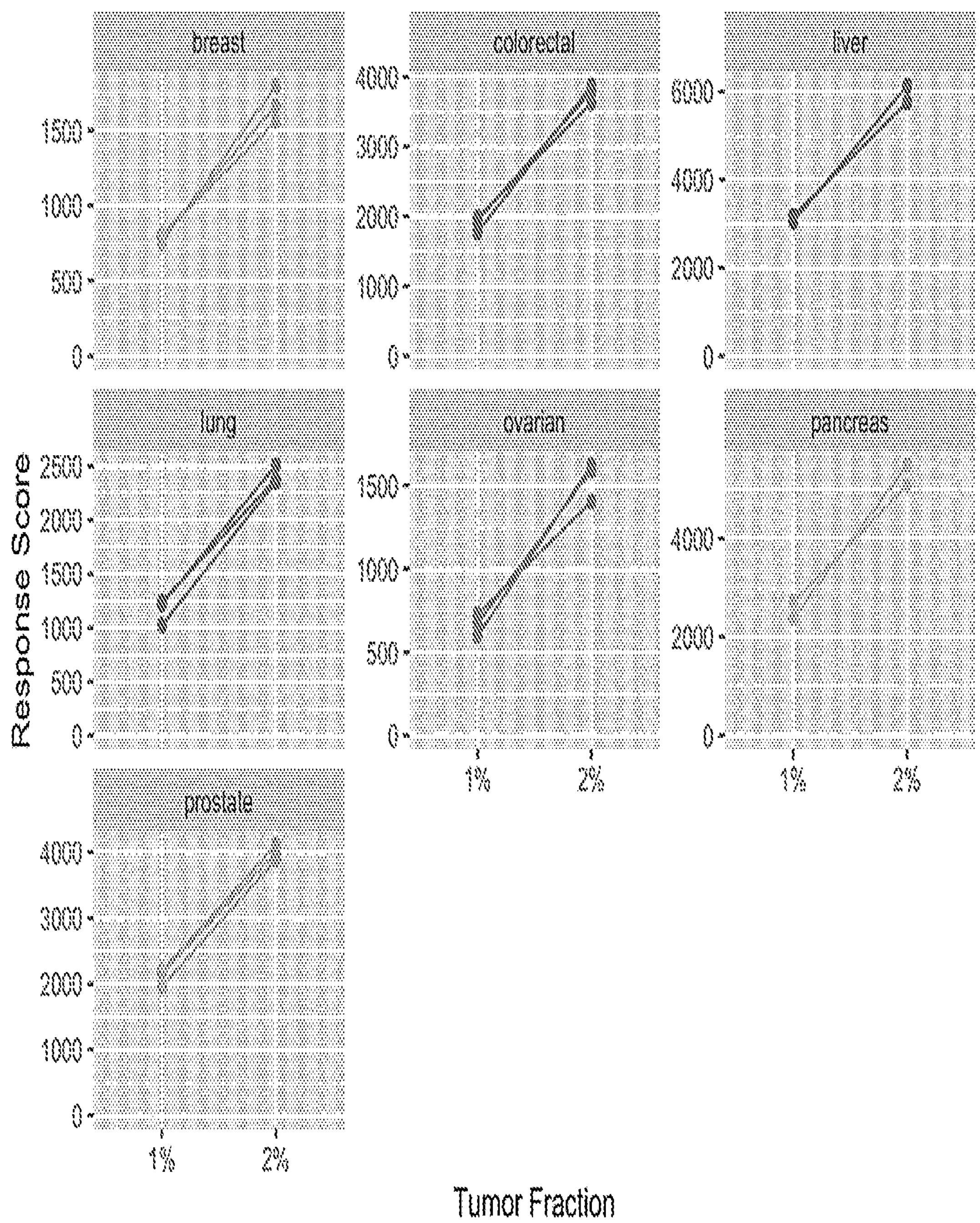

FIG. 14 shows Response Scores measured in triplicate at each tumor fraction for each tumor type.

Figure 15:
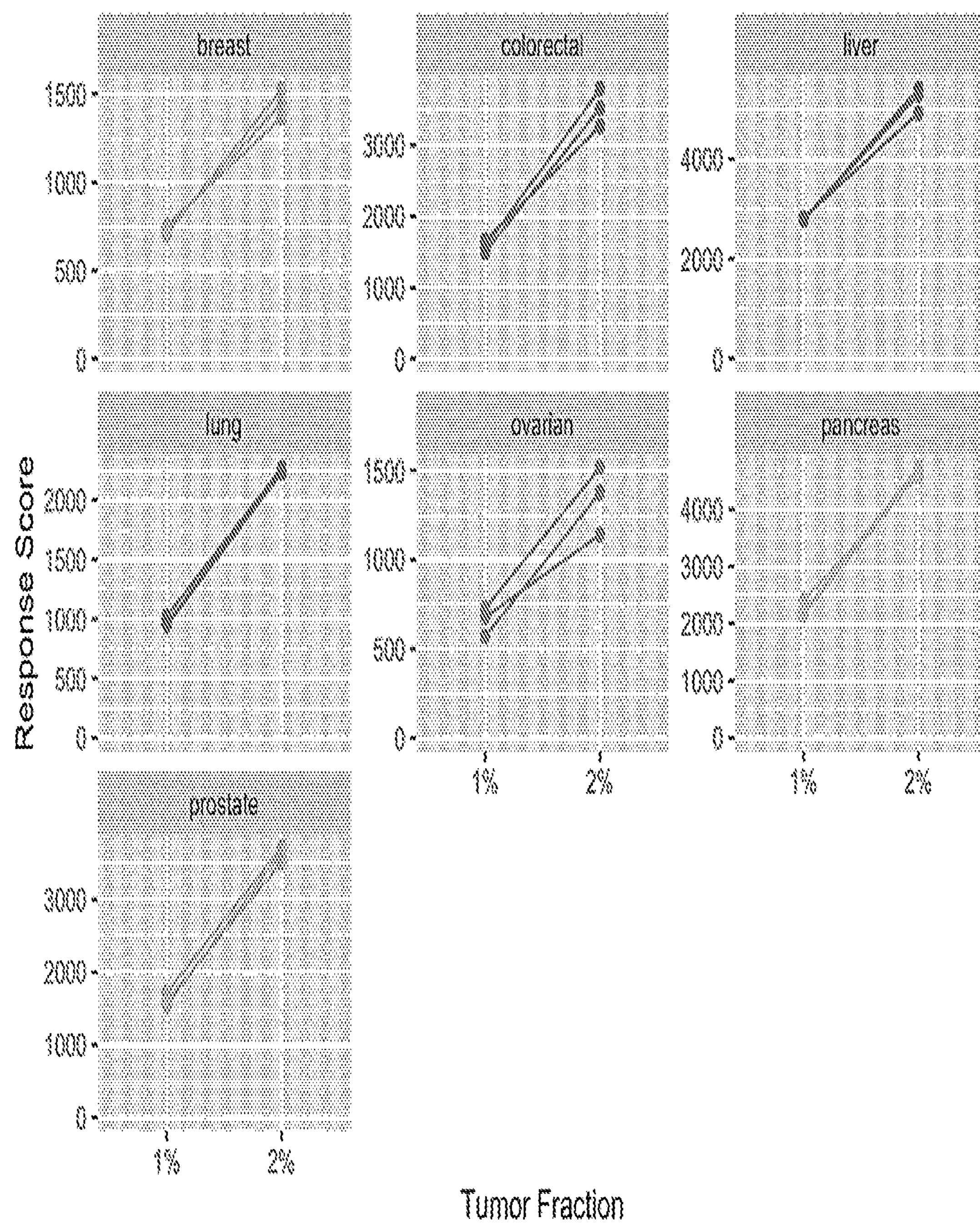

FIG. 15 shows Response Scores measured in triplicate at each tumor fraction for each tumor type.

Figure 16:
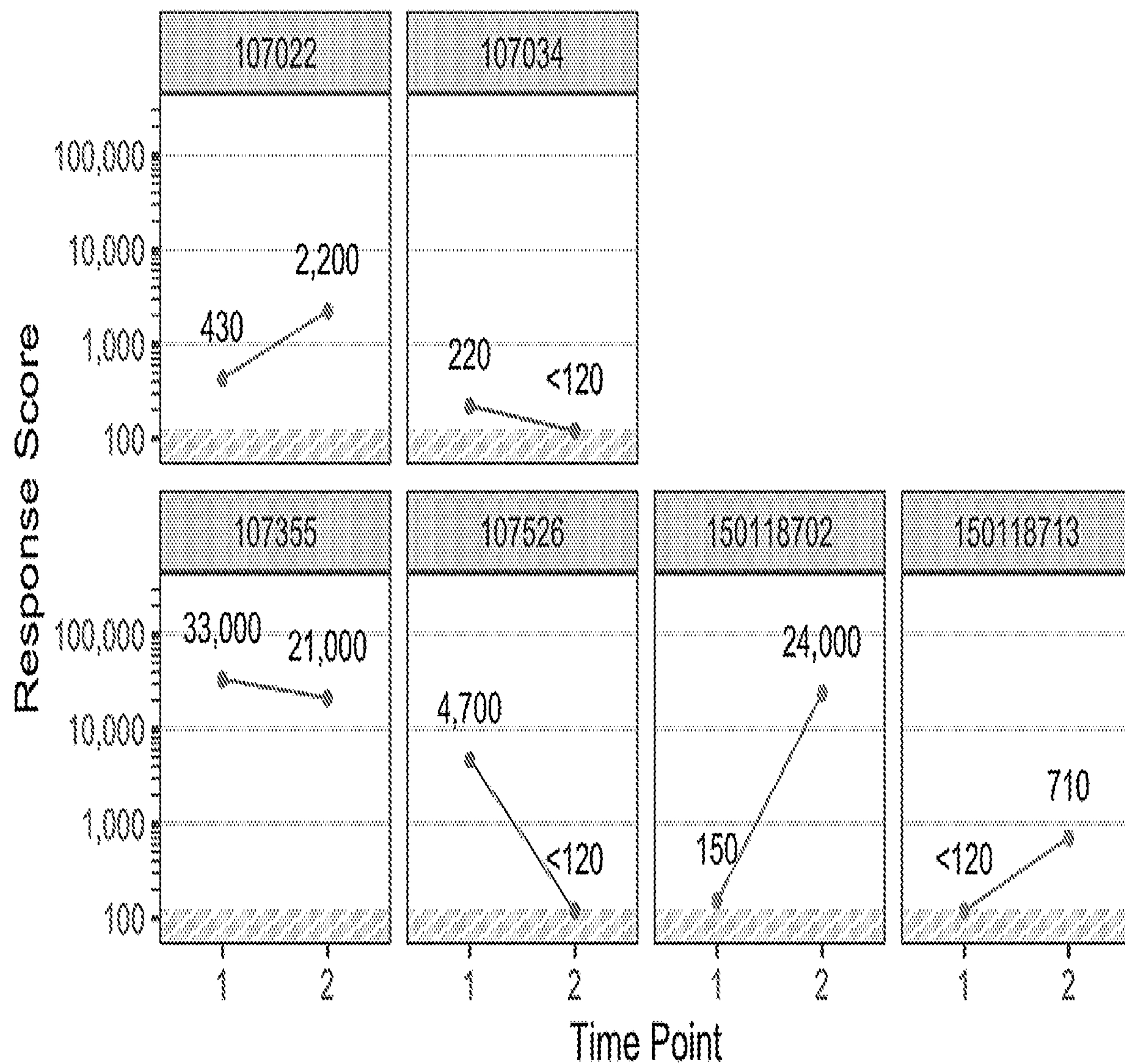

FIG. 16 shows Response Scores measured for 8 cancer subjects, each with samples from two time points. 8 cancer subjects included three cancer types (lung=4 subjects, pancreas=3 subjects, endometrial=1 subject). Colors in key indicate the call that was made based on the change in Response Score.

Figure 17:
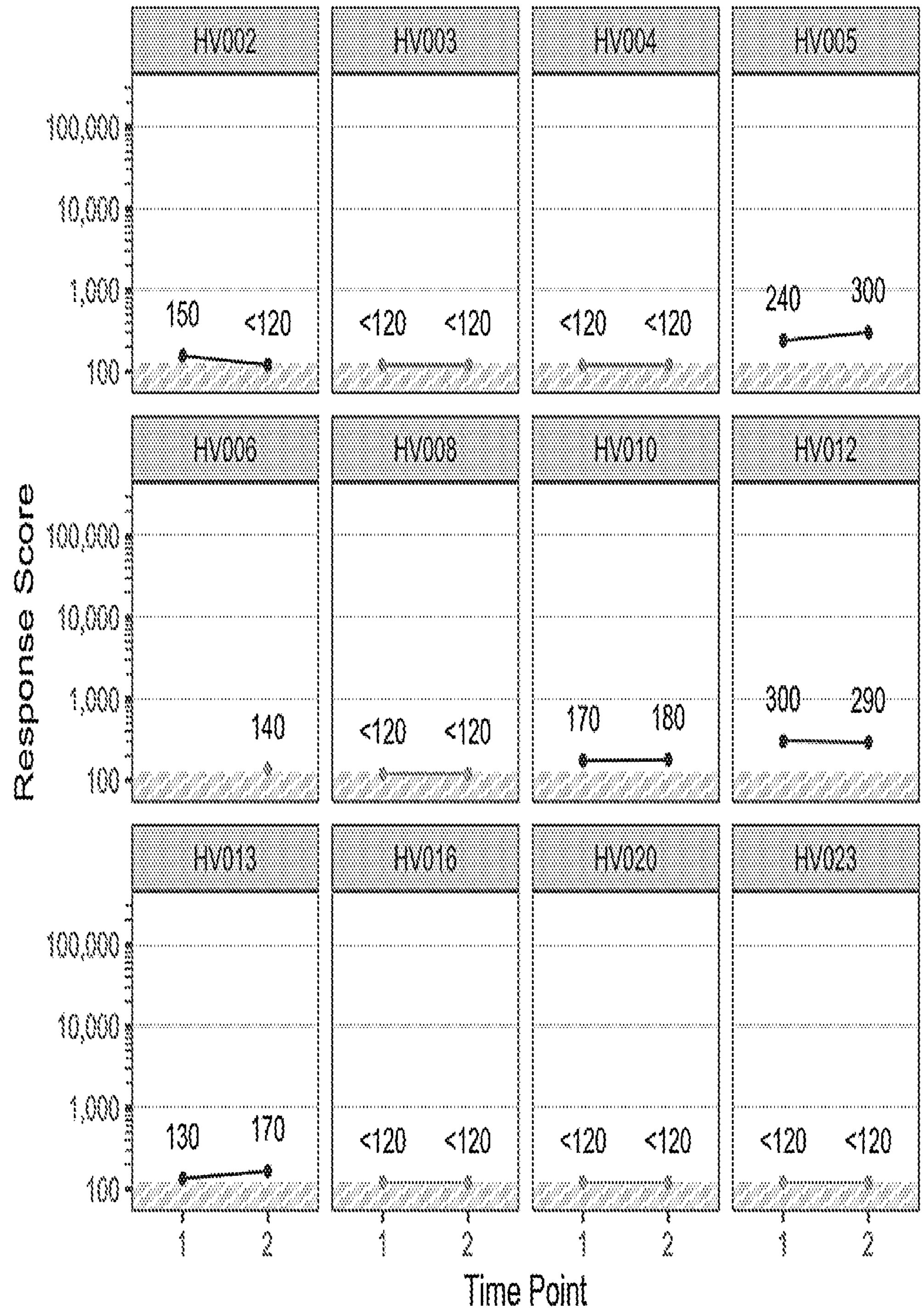

FIG. 17 shows Response Scores measured for 12 healthy subjects, each with samples from two time points. The cfDNA sample at time point 1 for subject HV006 failed sample QC criteria, so no call was made for that subject. No change or Indeterminate calls were made for the remaining 11 subjects.

Figure 18:
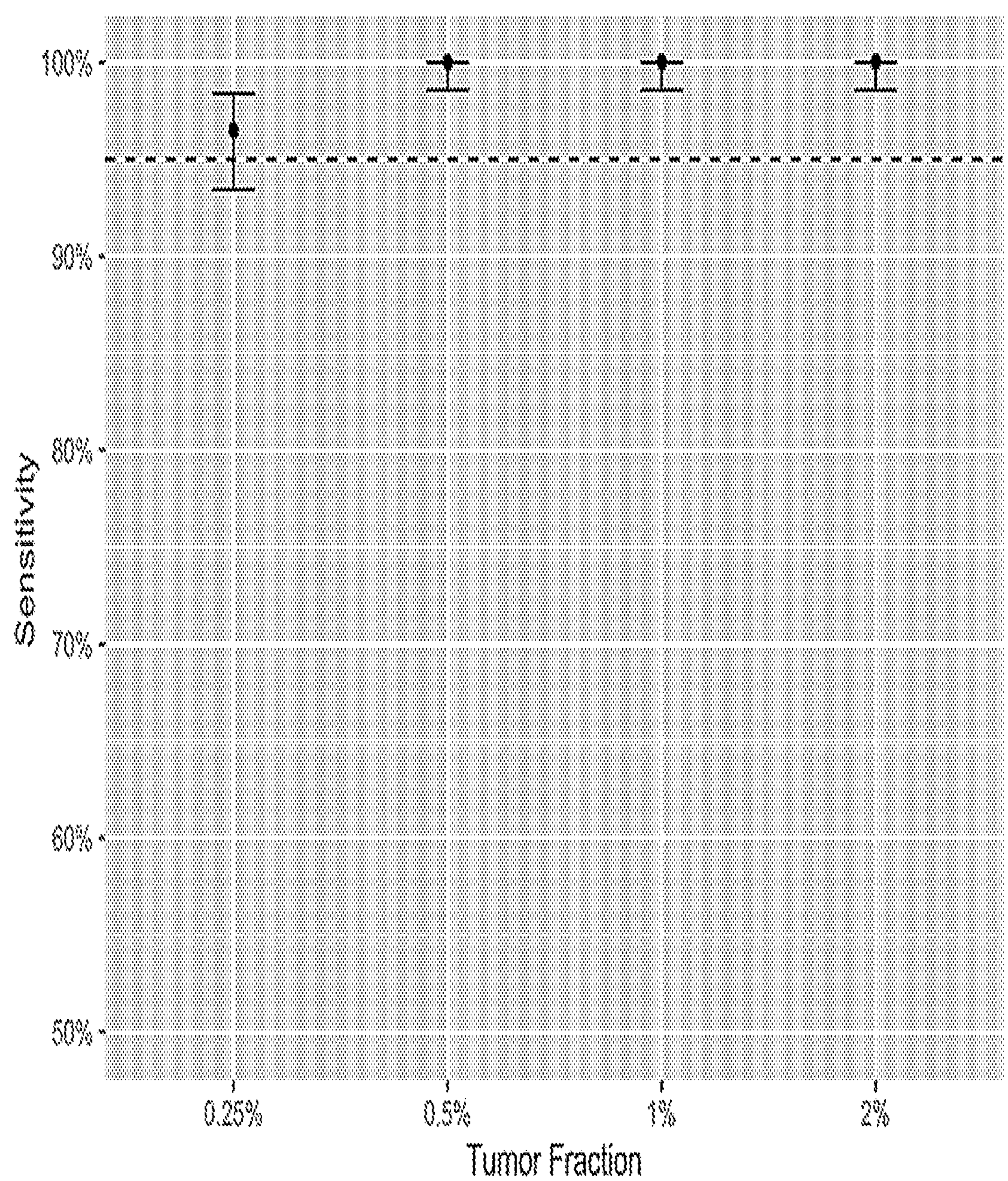

FIG. 18 shows sensitivity for each tumor fraction plotted with 95% confidence intervals. The dotted line indicates 95% sensitivity, i.e., the limit of detection sensitivity threshold. For each tumor fraction, sensitivity was calculated by comparing each of the 16 replicates to each of the 16 0% tumor fraction replicates (256 comparisons total).

Figure 19:
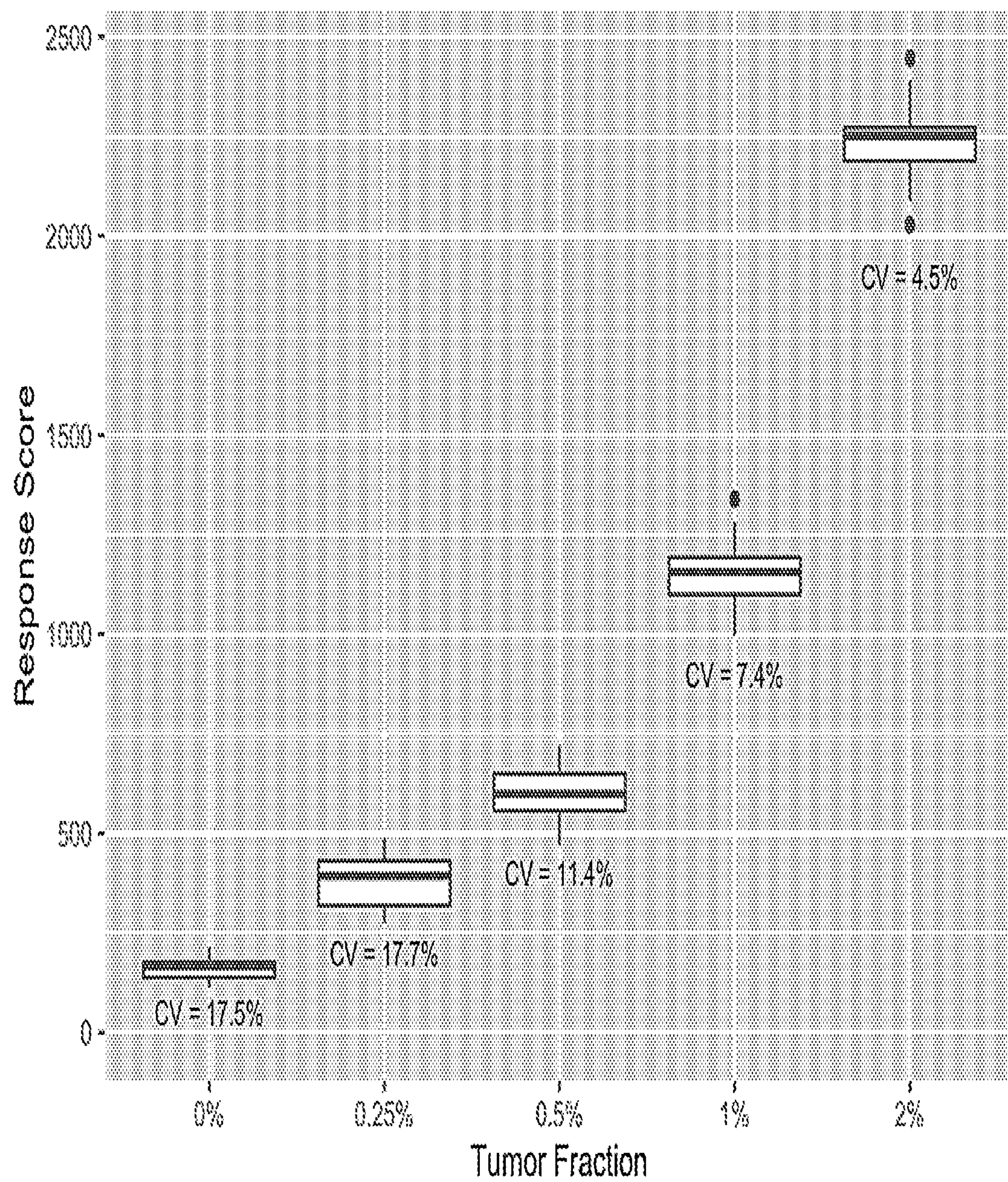

FIG. 19 shows box-plots for the median and interquartile range of Response Scores at each tumor fraction. The standard deviation and mean of each tumor fraction were used to calculate CV.

Figure 20:
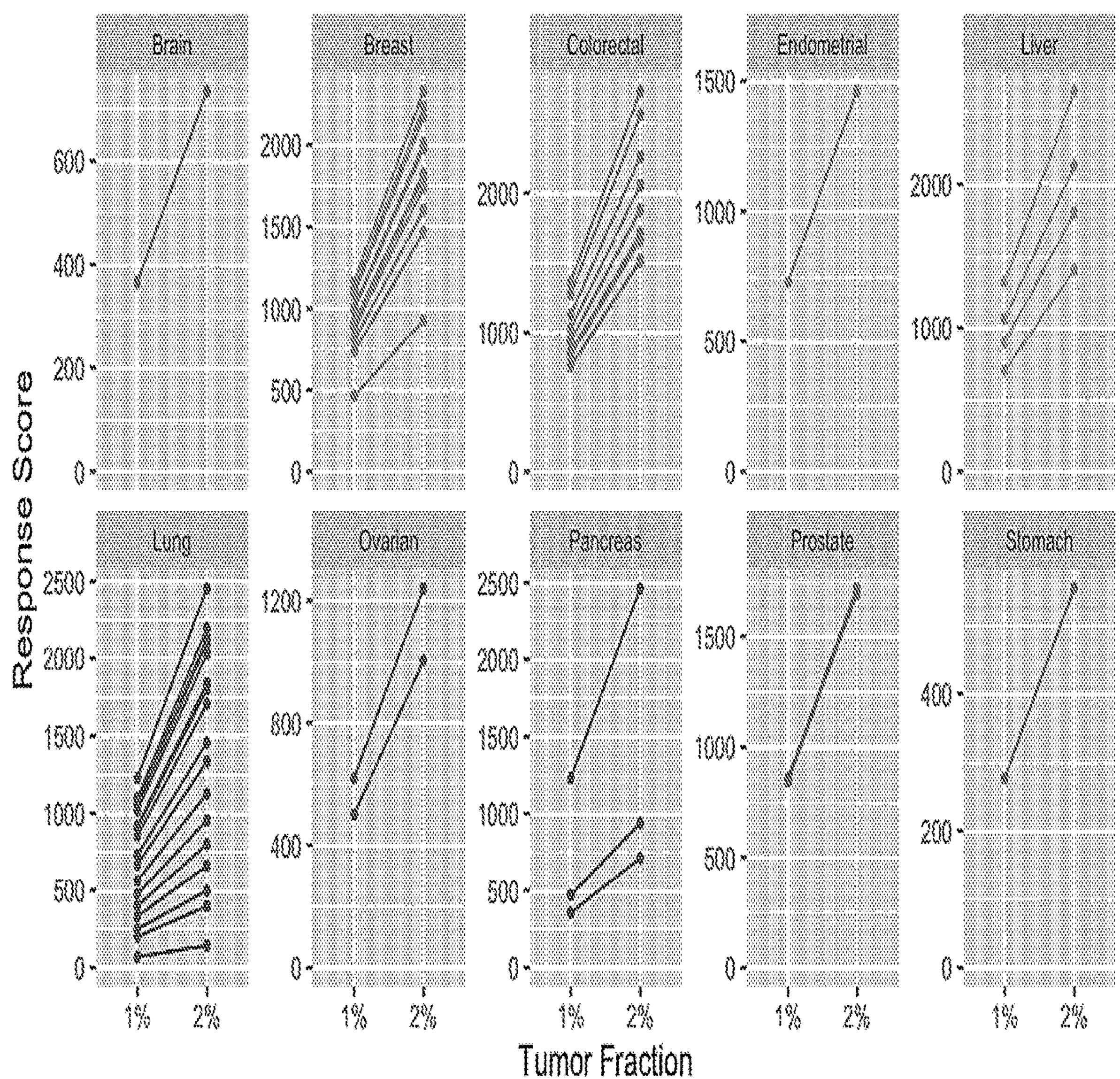

FIG. 20 shows Simulated Response Scores for 1% and 2% Tumor DNA Samples.

Figure 21:
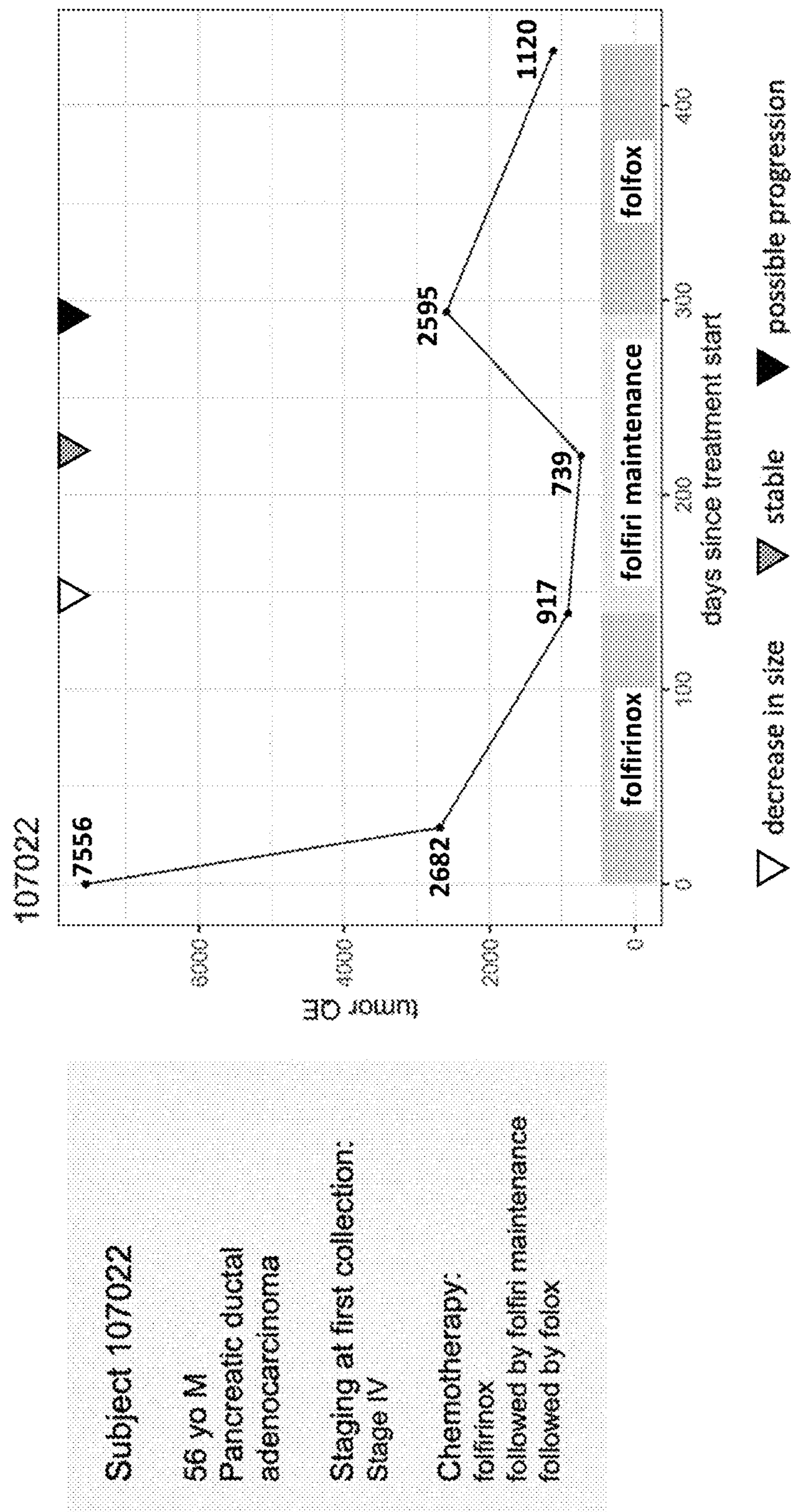

FIG. 21 shows methylation analysis for a 56 year old male subject with pancreatic ductal adenocarcinoma stage IV at time of first collection. Subject was treated with folfirinox ("folfiri"), followed by folfiri maintenance, and followed by folox. FIG. 21 shows tumor QE (y-axis) over days since last treatment (x-axis). Triangles indicate clinician-mediated staging of cancer using imaging.

Figure 22:
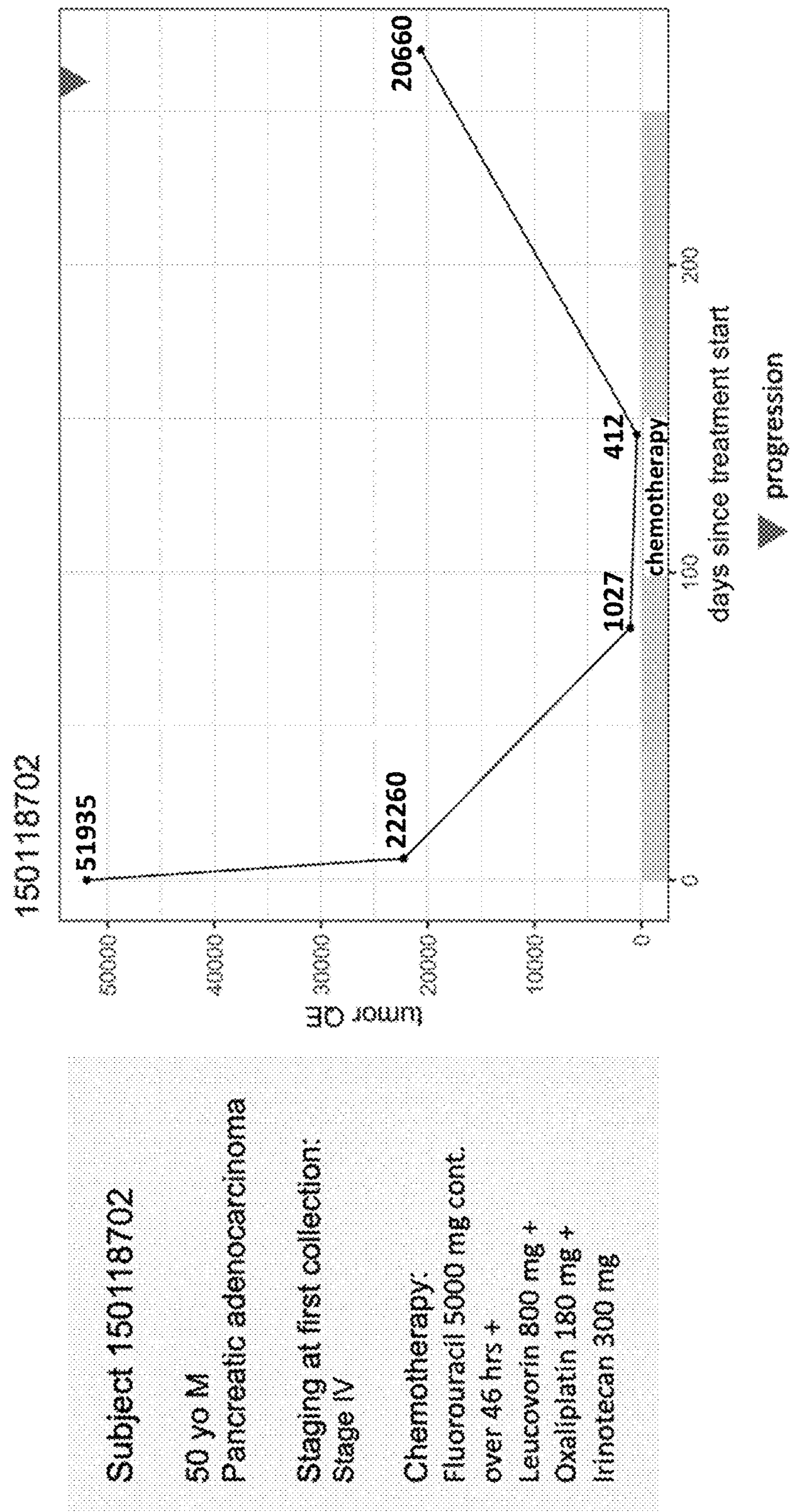

FIG. 22 shows methylation analysis for a 50 year old male subject with pancreatic adenocarcinoma stage IV at time of first collection. Subject was treated with fluorouracil 5000 mg continuous over 46 hours+leucovorin 800 mg+oxaliplatin 180 mg+Irinotecan 300 mg. FIG. 22 shows tumor QE (y-axis) over days since last treatment (x-axis). Triangle indicates clinician-mediated of cancer using imaging.

Figure 23:
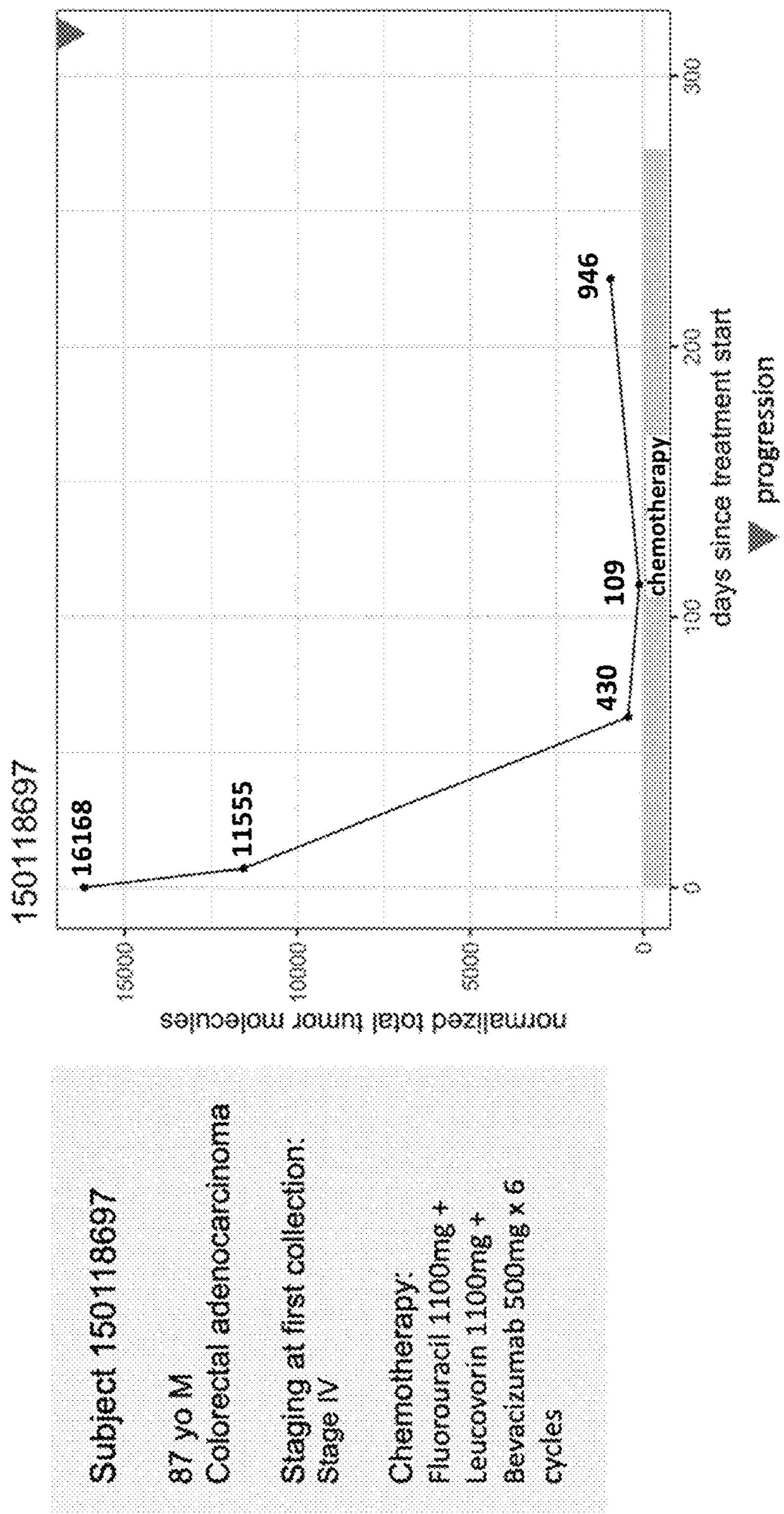

FIG. 23 shows methylation analysis for an 87 year old male subject with colorectal adenocarcinoma stage IV at time of first collection. Subject was treated with 6 cycles of fluorouracil 1100 mg+leucovorin 1100 mg+Bevacizumab 500 mg. FIG. 23 shows tumor QE (y-axis) over days since last treatment (x-axis). Triangle indicates clinician-mediated of cancer using imaging.

Figure 24:
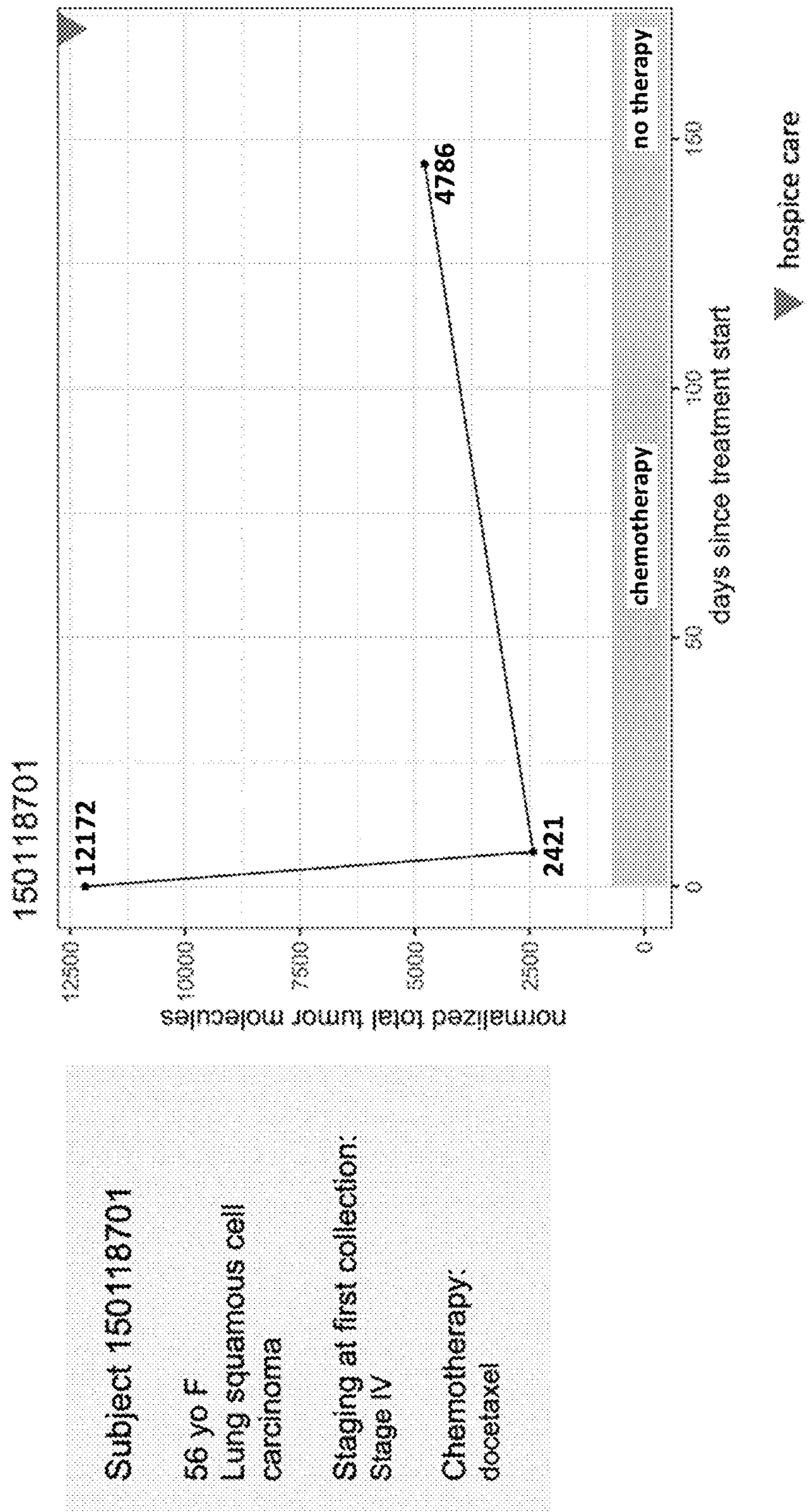

FIG. 24 shows methylation analysis for a 56 year old female subject with lung squamous cell carcinoma stage IV at time of first collection. Subject was treated with 6 docetaxel. FIG. 24 shows tumor QE (y-axis) over days since last treatment (x-axis). Triangle indicates subject entering into hospice care.

Figure 25:
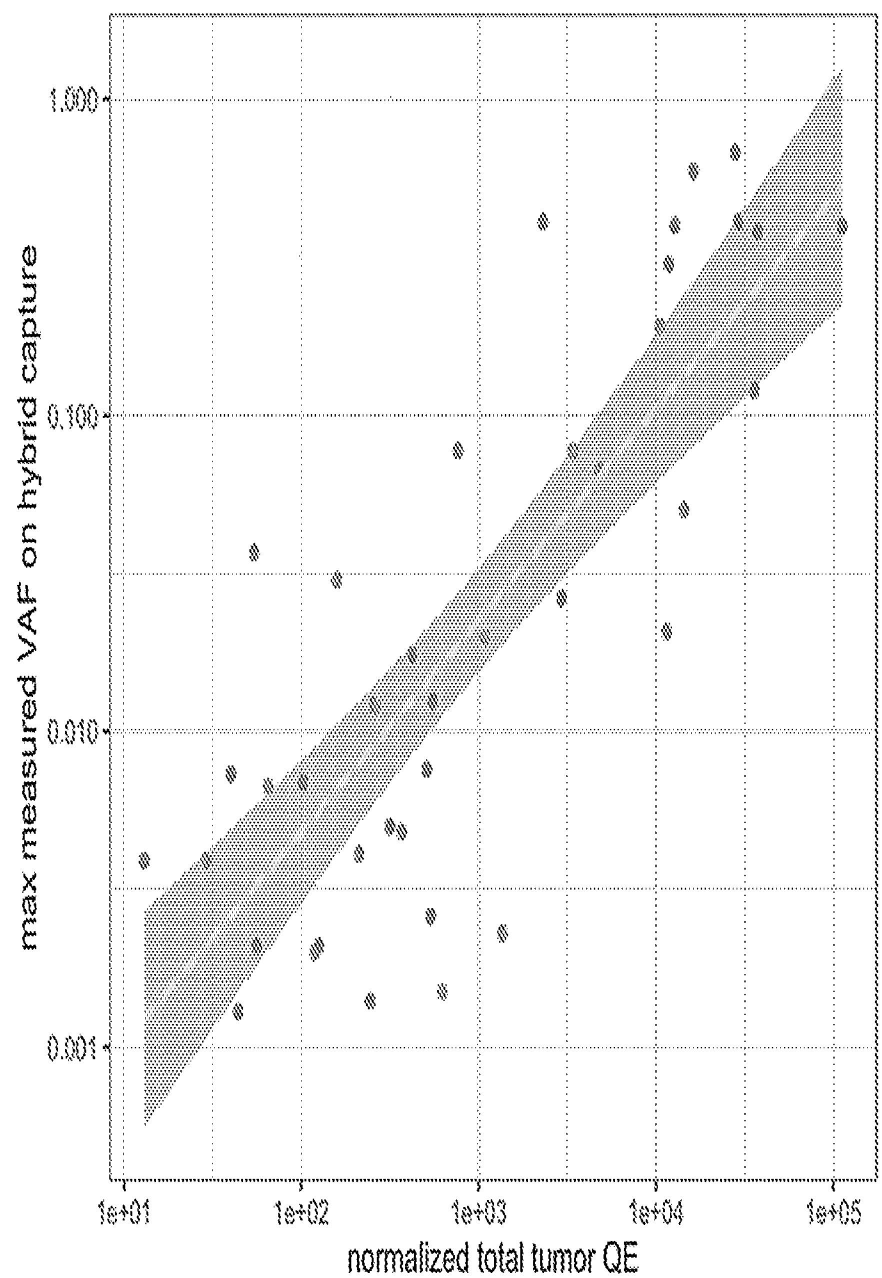

FIG. 25 shows results of a treatment selection assay performed on an aliquot of plasma collected at the same time point as the methylation assay for 40 different samples. FIG. 25 shows for each sample the maximum variant allele fraction (VAF) (y-axis label: max measured VAF on hybrid capture) versus the normalized total tumor QE (x-axis).

Figure 26:
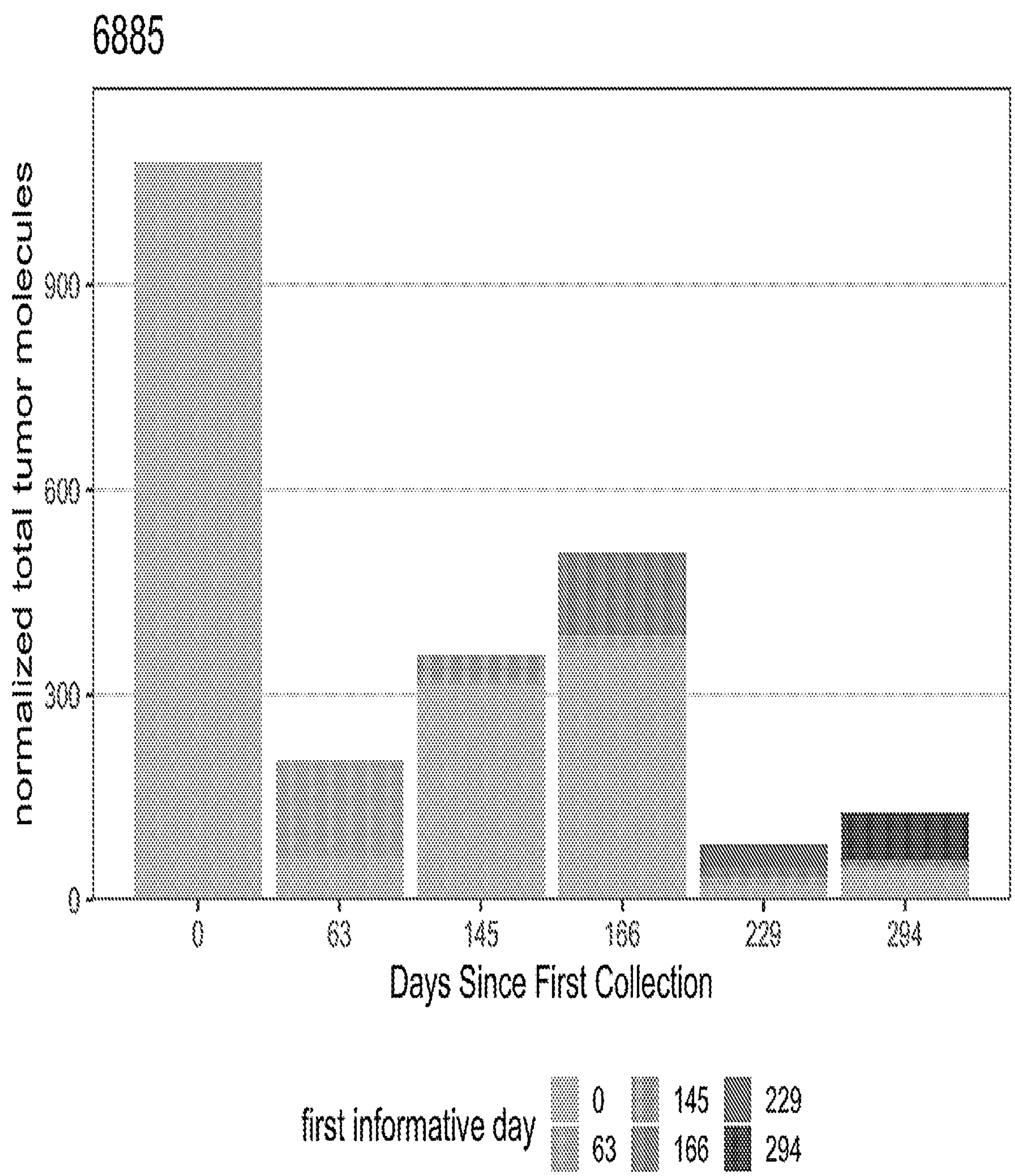

FIG. 26 shows a methylation profile for Subject 6885 measured at various time points over the course of about 294 days. In particular, FIG. 26 shows normalized total tumor molecules (y-axis) separated into loci by color. Methylation profiles were measured at day 0, 63, 145, 166, 229, and 294. Numbers in the key indicate the percentage of total methylation for each of the loci at that particular time point.

Figure 27:
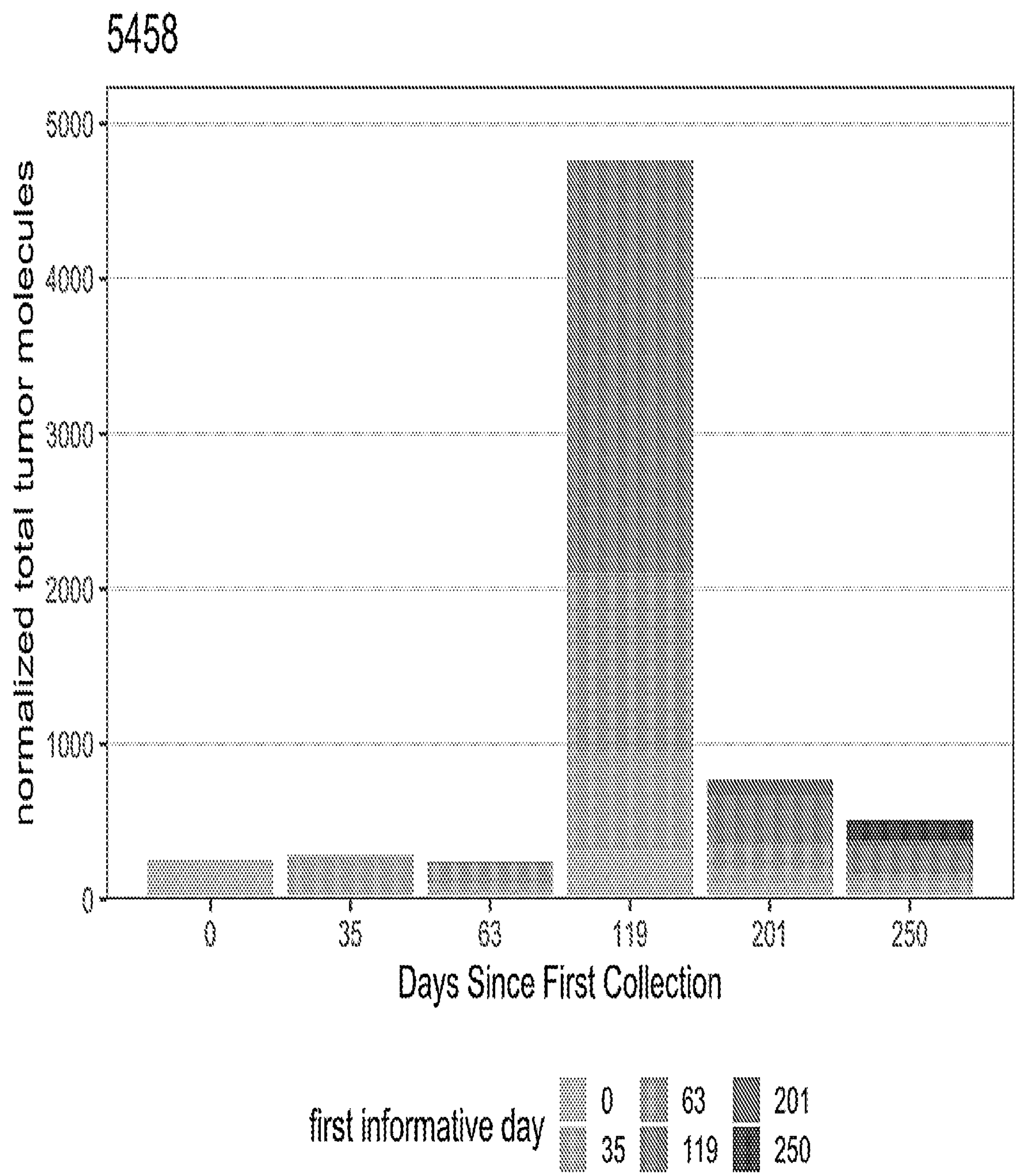

FIG. 27 shows a methylation profile for Subject 5458 measured at various time points over the course of about 250 days. In particular, FIG. 27 shows normalized total tumor molecules (y-axis) separated into loci by color. Methylation profiles were measured at day 0, 35, 63, 119, 201, and 250. Numbers in the key indicate the percentage of total methylation for each of the loci at that particular time point.

Figure 28:
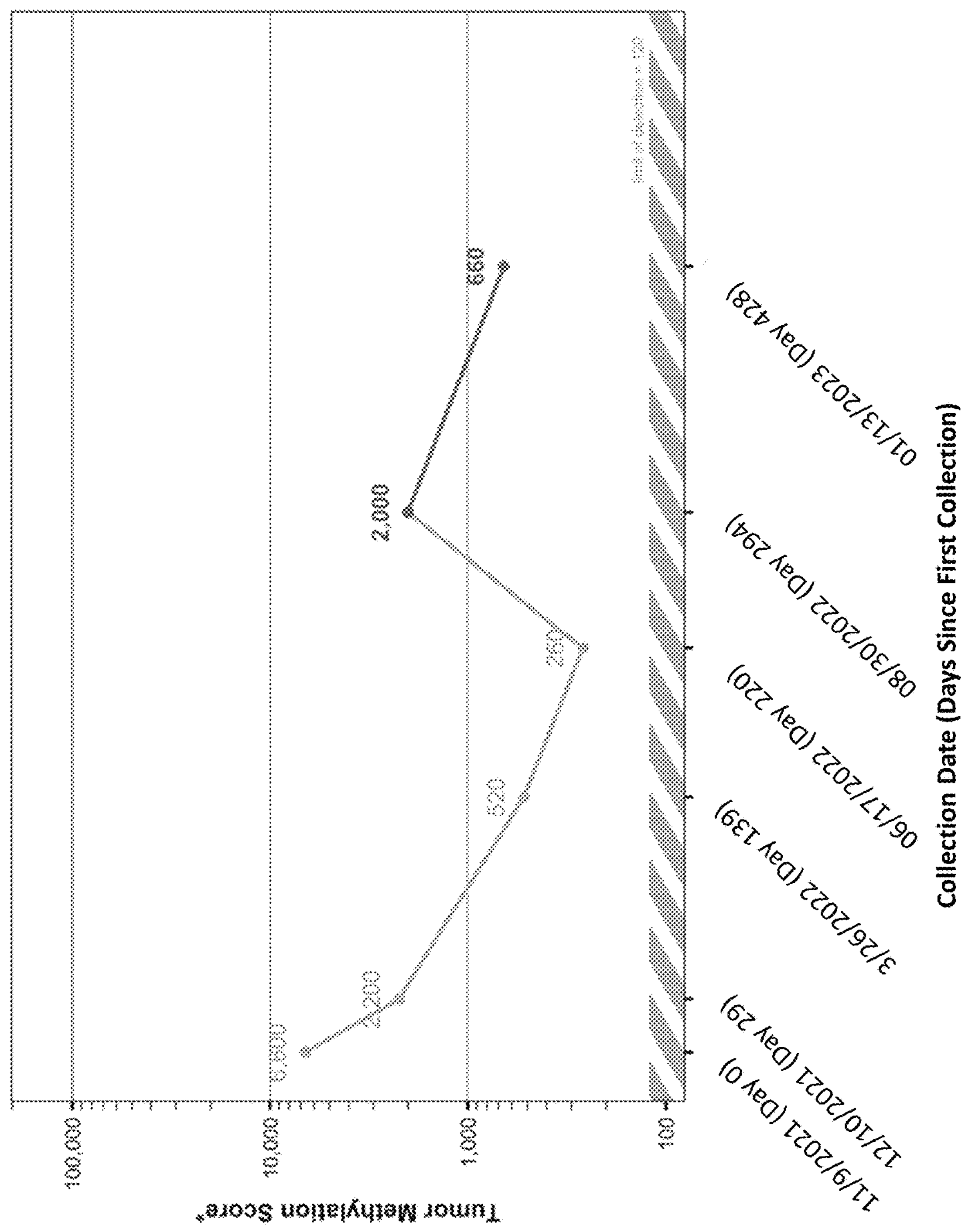

FIG. 28 shows the Tumor Methylation Score represented as the normalized sum of methylated molecules at >500 loci that are hypermethylated in circulating tumor DNA (ctDNA) for each of the collection dates. Days since first collection are indicated in parenthesis.

6. DETAILED DESCRIPTION

In one aspect, the present disclosure provides a method to quantify DNA methylation in a sample containing DNA sequences. The method can include treating the sample to encode the presence or absence of DNA methylation in the DNA sequences; adding to the sample a set of synthetic molecules, the set of molecules comprising target-associated regions having a nucleotide sequence that matches a target sequence region of an endogenous target molecule and variation regions with a nucleotide sequence that does not match a sequence region of an endogenous target molecule; generating a co-amplification mixture comprising an amplified set of synthetic molecules and an amplified set of at least ten target loci from the DNA sequences; sequencing the co-amplification mixture at a read depth of at least one read sequence per molecule in the sample to generate sequence reads; determining a number of the sequence reads that are methylated sequence reads; quantifying (determining) an absolute number of methylated molecules in the sample based on the number of methylated reads from the sample and a number of reads from the set of synthetic molecules; and optionally, aggregating the number of molecules across at least two loci.

Figure 1A:
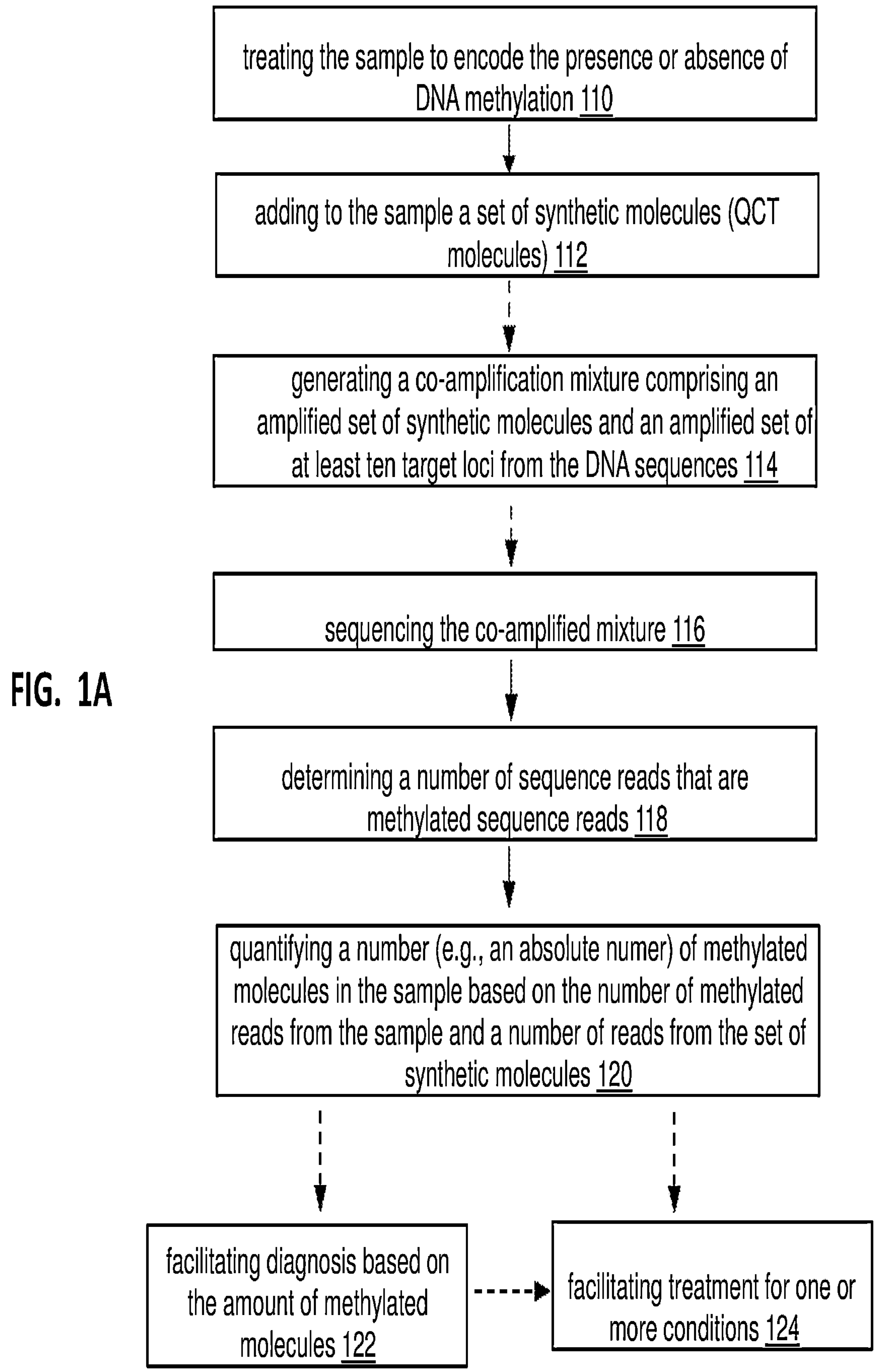
FIG. 1A shows a flowchart representation of a non-limiting embodiment of a method of quantifying DNA methylation in a sample.

As shown in FIG. 1A, embodiments of a method to quantify DNA methylation in a sample can include: treating the sample to encode the presence or absence of DNA methylation 110; adding to the sample a set of synthetic molecules (e.g., quality control template (QCT) molecules) where each synthetic molecule comprises a target-associated region and a variation region) 112; generating a co-amplification mixture comprising an amplified set of synthetic molecules and an amplified set of at least ten target loci from the DNA sequences 114; sequencing the co-amplification mixture at a read depth of at least one read sequence per molecule in the sample to generate sequence reads 116; determining a number of the sequence reads that are methylated sequence reads 118; quantifying (determining) a number (e.g., an absolute number) of methylated molecules in the sample based on the number of methylated reads from the sample and a number of reads from the set of synthetic molecules 120; and facilitating diagnosis based on the amount of methylated molecules 122 and/or facilitating treatment for one or more conditions 124.

In some embodiments, the addition of a spike-in of known sequence and quantity is added to the sample prior to treating the sample to encode the presence or absence of DNA methylation.

In some embodiments, treating the sample to encode presence or absence of DNA methylation is conducted by bisulfite conversion or enzymatic conversion or any other suitable methodology of treatment that separately identifies methylated DNA molecules.

In some embodiments, the set of co-amplification synthetic molecules is a set of quantitative counting templates (QCTs).

In some embodiments, the target loci are chosen due to an increase in DNA methylation in cancerous tissue compared to normal tissue.

In some embodiments, at least 100 target loci are amplified.

In some embodiments, at least 800 target loci are amplified.

In some embodiments, the co-amplification mixture is sequenced at a read depth of at least 1 read per molecule.

In some embodiments, the co-amplification mixture is sequenced at a read depth of 10 or more reads per molecule, 100 or more reads per molecule, or 1000 or more reads per molecule.

In some embodiments, the co-amplification mixture is sequenced at a read depth of at least 1000 sequencing reads per genomic location.

In some embodiments, further comprising aggregating the number of molecules across loci, wherein the loci are cancer specific loci.

In some embodiments, quantification of DNA methylation is performed in a cell-free DNA sample.

In some embodiments, cell-free DNA from plasma and cell-free DNA from the buffy coat is extracted from the same patient prior to any spike-in step and treating the sample to encode the presence or absence of DNA methylation.

In some embodiments, further comprising aggregating the number of molecules across loci in the cell-free DNA sample, wherein loci that contain lower than a threshold amount of methylated molecules in the buffy coat sample.

In some embodiments, a generated co-amplification mixture comprises an amplified set of spike-in molecules, amplified set of synthetic molecules, and amplified set of at least 10 target loci from the plurality of DNA sequences and at least one locus that demonstrates high methylation in cell-free DNA.

In some embodiments, further comprising aggregating the number of methylated molecules across target loci and at least one locus that demonstrates high methylation in cell-free DNA.

In some embodiments, further comprising normalizing the aggregate number of target methylated molecules by the aggregate number of molecules with high methylation in cell-free DNA.

In some embodiments, further comprising a step of background subtraction.

In some embodiments, further comprising a step of filtering hypermethylated loci.

In some embodiments, further comprising a step of background subtraction and a step of filtering hypermethylated loci.

In some embodiments, the step of background subtraction comprises subtracting the number of methylated molecules (or the methylation signal) as measured in the buffy coat from the number of methylated molecules (or the methylation signal) in the cfDNA.

In some embodiments, further comprising subtracting the number of methylated molecules (or the methylation signal) as measured in the buffy coat from the number of methylated molecules (or the methylation signal) in the cfDNA on a per-locus basis.

In some embodiments, the step of filtering hypermethylated loci comprises filtering target loci with high background methylation prior to quantifying the absolute number of methylated molecules in the sample.

In some embodiments, the filtered target loci include target loci having a number of methylated molecules (or the methylation signal) with buffy coat methylation above a threshold.

In some embodiments, the threshold is sample-specific. In some embodiments, the threshold is subject-specific. In such cases, this is referred to as a “personalized” blacklist. In some embodiments where the threshold is sample-specific or subject-specific the threshold is determined by evaluating the buffy coat methylation signal for loci with high methylation cfDNA signal in non-cancer subjects.

In some embodiments, the threshold comprises a pre-determined mean tumor methylated QE, a predetermined max tumor methylated QE, or a combination thereof.

In some embodiments, the pre-determined mean tumor methylated QE is equal to or greater than 0.5, equal to or greater than 1.0, equal to or greater than 1.5, equal to or greater than 2.0, equal to or greater than 2.5, equal to or greater than 3.0, equal to or greater than 3.0, equal to or greater than 3.5, equal to or greater than 4.0, equal to or greater than 4.5, or equal to or greater than 5.0.

In some embodiments, the pre-determined max tumor methylated QE in any non-cancer specimen is equal to or greater than 5, equal to or greater than 10, equal to or greater than 15, equal to or greater than 20, equal to or greater than 25, equal to or greater than 30, equal to or greater than 35, equal to or greater than 40, equal to or greater than 45, or equal to or greater than 50.

In one embodiment, the threshold comprises (1) max tumor QE in any non-cancer specimen>15; and (2) mean tumor QE (including 0s)>2.

In some embodiments, the target loci are selected to be differentially methylated across at least two cancer tissues of origin.

In some embodiments, at least 5 loci per cancer tissue of origin are targeted.

In some embodiments, cancer tissue of origin is determined based on the abundance of methylated molecules across targeted loci.

An aspect of the present disclosure provides a method to quantify the amount of tumor DNA in a sample containing DNA sequences, the method comprising: i. adding to the sample a set of synthetic molecules, the set of molecules comprising: target-associated regions having a nucleotide sequence that matches a target sequence region of an endogenous target molecule, and variation regions with a nucleotide sequence that does not match a sequence region of an endogenous target molecule; ii. generating a co-amplification mixture comprising an amplified set of synthetic molecules and an amplified set of at least 10 target loci from the DNA sequences; iii. sequencing the co-amplification mixture at a read depth of at least one read sequence per molecule in the sample to generate sequence reads; iv. quantifying the absolute number of molecules containing a somatic mutation in the sample based on the number of reads from the sample and the number of reads from the set of synthetic molecules; and v. determining a lower bound for variant allele fraction based on the total number of molecules present in the sample at each locus prior to amplification.

An aspect of the present disclosure provides a method to quantify methylation in a DNA sample, the method comprising: adding a spike-in of known sequence to the sample;

treating the sample to encode the presence or absence of methylation into the DNA sequence itself; adding to the sample a set of QCT or spike-in molecules, the set of molecules comprising: target-associated regions having a nucleotide sequence that matches a target sequence region of an endogenous target molecule, and variation regions with a nucleotide sequence that does not match a sequence region of an endogenous target molecules; amplifying the mixture of sample and QCT/spike-in molecules at 10 or more different loci simultaneously; sequencing the amplified mixture (at a read depth of at least one read per molecule in the sample); determining the number of reads that are methylated based on the read sequence; computational determining the number of methylated molecules in the sample based on the number of methylated reads from the sample and the number of reads from the QCT/spike-in at each locus; and aggregating the number of molecules across loci.

In some embodiments, the method comprises adding a constant amount of spike-in prior to methylation conversion to each sample so that the efficiency of the conversion process can be monitored.

In some embodiments, treating the sample to encode the presence or absence of methylation into the DNA sequence itself comprises performing a bisulfite conversion or an enzymatic conversion. Bisulfate conversion is described in U.S. Pat. No. 8,257,950, which is incorporated herein by reference in its entirety. Bisulfite conversion and enzymatic conversion converts unmethylated cytosines to uracils. Thus, whether each read came from a methylated molecule or not can be determined by determining the number of reads that are methylated based on the read sequence.

In some embodiments, QCTs can be used quantify each locus. Alternatively, in other embodiments, spike-in molecules can be used to quantify each locus.

In some embodiments, amplifying the mixture of samples and QCT/spike-in molecules at 10 or more different loci simultaneously. In some embodiments, these locations are chosen based on being more methylated in tumors compared to normal tissue of the same tissue type. In some embodiments, more than 100 locations are amplified. In some embodiments, more than 800 locations are amplified. In some embodiments, these loci have increased methylation in cancer.

In some embodiments, the method includes sequencing the amplified mixture (e.g., at a read depth of at least one read per molecule in the sample). The read depth qualifier could be optional. In some embodiments, the read depth qualifier is at least 1000 reads per locus (e.g., based on the expectation of 1000-2000 sample molecules at each genomic location per tube of blood).

In some embodiments, treating the sample to encode the presence or absence of methylation into the DNA sequence itself comprises bisulfite conversion or an enzymatic conversion.

In some embodiments, the method includes computational determining the number of methylated molecules in the sample based on the number of methylated reads from the sample and the number of reads from the QCT/spike-in at each locus. For spike-ins, the method includes dividing the number of sample reads by the number of spike-in reads times the number of spike-ins added to the sample.

In some embodiments, the method includes aggregating the number of molecules across loci. In certain embodiments, adding up a subset of loci (e.g. adding up just the lung cancer specific loci).

An aspect of the present disclosure includes a method to quantify methylation in a cell-free DNA sample, the method includes extracting cell-free DNA from the plasma and DNA from the buffy coat from the same person; adding a spike-in of known sequence to each DNA sample; treating each DNA sample to encode the presence or absence of methylation into the DNA sequence itself; adding to each DNA sample a set of QCT or spike-in molecules, the set of molecules comprising: target-associated regions having a nucleotide sequence that matches a target sequence region of an endogenous target, and variation regions with a nucleotide sequence that does not match a sequence region of an endogenous target molecules; amplifying the mixture of sample and QCT/spike-in molecules at 10 or more different loci simultaneously; sequencing the amplified mixture (at a read depth of at least one read per molecule in the sample); determining the number of reads that are methylated based on the read sequence; and computational determining the number of methylated molecules in the sample based on the number of reads from the sample and the number of reads from the QCT/spike-in at each locus; and aggregating.

In some embodiments, the method includes aggregating the number of molecules across loci in the cell-free DNA sample while excluding loci with significant amounts of methylated molecules in the buffy coat sample. In order to determine significance, if any, the method includes determining a threshold number of molecules.

For example, cfDNA has background methylation signal that differs from patient to patient. Because the majority of cell-free DNA originates from white blood cells, one aspect of the method can use the methylation signal from the buffy coat as a baseline. In some embodiments, the method includes minimizing the cfDNA background signal, by ignoring any loci with significant methylation in the buffy coat (e.g., useful for minimal residual disease (MRD) detection applications). In other embodiments, the method avoids performing background subtraction by choosing loci that have low methylation background in most people.

An aspect of the present disclosure includes a method to quantify methylation in a DNA sample, the method comprising: adding a spike-in of known sequence to the sample; treating the sample to encode the presence or absence of methylation into the DNA sequence itself; adding to the sample a set of QCT or spike-in molecules, the set of molecules comprising: a) target-associated regions having a nucleotide sequence that matches a target sequence region of an endogenous target, and b) variation regions with a nucleotide sequence that does not match a sequence region of an endogenous target molecule; amplifying the mixture of sample and QCT/spike-in molecules at least 10 different target loci simultaneously and at least one locus known to be highly methylated in cfDNA; sequencing the amplified mixture (at a read depth of at least one read per molecule in the sample); determining the number of reads that are methylated based on the read sequence; computational determining the number of methylated molecules in the sample based on the number of reads from the sample and the number of reads from the QCT/spike-in at each locus aggregating the number of methylated molecules across target loci and highly methylated loci; and normalizing the aggregate number of target methylated molecules by the aggregate number of highly methylated loci. For example, normalizing the aggregate number of target methylated molecules by the aggregate number of highly methylated loci can include 100 methylated molecules for 5000 input molecules.

For example, in some embodiments, the method can monitor the amount of ctDNA over time. Thus, the measurements of methylated molecules may need to be consistent relative to the total input amount of DNA. For example, if a patient's cancer is stable, but 2× the amount of cfDNA is collected in the second time point compared to the first time point, it could appear that the cancer doubled in size even though the cancer remained the same size. In one aspect of the present methods, the present method can look at loci that are highly methylated in cfDNA regardless of whether the cfDNA came from the tumor or not, and normalize the target loci to these highly methylated control loci.

An aspect of the present disclosure includes a method to quantify methylation in a DNA sample, the method comprising: treating the sample to encode the presence or absence of methylation into the DNA sequence itself; amplifying the mixture of sample and QCT/spike-in molecules at 10 or more different target loci simultaneously and at least one locus (e.g. at least one locus, at least two loci, at least three loci, at least four loci, at least five loci, at least six loci, at least seven loci, at least eight loci, at least nine loci, at least ten loci, and the like) known to be highly methylated in cfDNA; sequencing the amplified mixture (at a read depth of at least one read per molecule in the sample); determining the number of reads that are methylated based on the read sequence; computational determining the average number of methylated reads in target loci and the average number of methylated reads in highly methylated loci; aggregating the number of methylated reads across target loci and highly methylated loci; and normalizing the aggregate number of target methylated reads by the aggregate number of highly methylated loci methylated reads.

An aspect of the present disclosure includes a method to quantify methylation in a DNA sample, the method comprising: adding a spike-in of known sequence to the sample; treating the sample to encode the presence or absence of methylation into the DNA sequence itself; adding to the sample a set of QCT or spike-in molecules, the set of molecules comprising: a) target-associated regions having a nucleotide sequence that matches a target sequence region of an endogenous target, and b) variation regions with a nucleotide sequence that does not match a sequence region of an endogenous target molecule; amplifying the mixture of sample and QCT/spike-in molecules at 10 or more different loci simultaneously, with loci chosen to be differentially methylated across at least two cancer tissues of origin; sequencing the amplified mixture (at a read depth of at least one read per molecule in the sample) determining the number of reads that are methylated based on the read sequence; computational determining the number of methylated molecules in the sample based on the number of methylated reads from the sample and the number of reads from the QCT/spike-in at each locus; and determining the tissue of origin based on the abundance of methylated molecules across loci.

For example, methylation patterns are different across tumor tissues of origin. In one aspect of the present methods, the method includes determining the tumor tissue of origin from a cfDNA sample based on which locations have methylated molecules.

In some embodiments, amplifying the mixture of sample and QCT/spike-in molecules at 5 or more loci (e.g., loci per cancer tissue of origin).

In some embodiments, determining the tissue of origin on the abundance of methylated molecules across loci comprises assigning a score to each tissue type.

In an aspect of the present disclosure, provided herein is a method to quantify the amount of tumor DNA in a DNA sample, the method comprising: adding to the sample a set of QCT or spike-in molecules, the set of molecules comprising: a) target-associated regions having a nucleotide sequence that matches a target sequence region of an endogenous target, and b) variation regions with a nucleotide sequence that does not match a sequence region of an endogenous target molecules; amplifying the mixture of sample and QCT/spike-in molecules at 10 or more different loci simultaneously; sequencing the amplified mixture (at a read depth of at least one read per molecule in the sample); computational determining the number of molecules containing a somatic mutation in the sample based on the number of reads from the sample and the number of reads from the QCT/spike-in at each locus; and determining a lower bound for variant allele fraction based on the total number of molecules initially present in the sample at each locus.

In another aspect, this disclosure features a method of determining a DNA methylation profile in a subject, the method comprising: treating a sample isolated from subject to encode the presence or absence of DNA methylation in the DNA sequences; adding to the sample a set of synthetic molecules, the set of molecules comprising: target-associated regions having a nucleotide sequence that matches a target sequence region of an endogenous target, and variation regions with a nucleotide sequence that does not match a sequence region of an endogenous target molecule; generating a co-amplification mixture comprising an amplified set of synthetic molecules and an amplified set of at least ten target loci from the DNA sequences; sequencing the co-amplification mixture at a read depth of at least one read sequence per molecule in the sample to generate sequence reads; determining a number of the sequence reads that are methylated sequence reads; quantifying (determining) a number of methylated molecules for each target loci in the sample based on the number of methylated sequence reads from each target loci in the sample and a number of reads from the set of synthetic molecules; and determining the methylation pattern in the subject based on the number of methylated molecules for target loci in the sample.

In another aspect, this disclosure features a method of determining a DNA methylation profile in a subject over time, the method comprising: at a first time point: i) treating a sample isolated from subject to encode the presence or absence of DNA methylation in the DNA sequences; ii) adding to the sample a set of synthetic molecules, the set of molecules comprising: target-associated regions having a nucleotide sequence that matches a corresponding nucleotide sequence to an endogenous target, and variation regions with a nucleotide sequence that does not match a sequence region of an endogenous target molecule; iii) generating a co-amplification mixture comprising an amplified set of synthetic molecules and an amplified set of at least ten target loci from the DNA sequences; iv) sequencing the co-amplification mixture at a read depth of at least one read sequence per molecule in the sample to generate sequence reads; v) determining a number of the sequence reads that are methylated sequence reads; vi) quantifying (determining) a number of methylated molecules for each target loci in the sample based on the number of methylated sequence reads from each target loci in the sample and a number of reads from the set of synthetic molecules; repeating steps i) to vi) at a second time point; and determining the methylation pattern in the subject based on the number of methylated molecules for each target loci in the sample at the first time point and the number of methylated molecules for each target loci in the sample at the second time point.

In some embodiments of determining a DNA methylation profile in a subject over time, the method includes repeating steps i) to vi) at a third time point, at a fourth time point, or at a fifth time point; and determining the methylation pattern in the subject based on the number of methylated molecules for each target loci in the sample at the third time point, at a fourth time point, or at a fifth time point.

In some embodiments of determining a DNA methylation profile in a subject, the method includes, upon detection of a change in the DNA methylation profile, performing a treatment selection assay on the subject. In some embodiments, the treatment selection assay comprises genomic profiling to detect novel somatic mutations, the abundance of somatic mutations, or both.

In some embodiments, the method detects a methylation signal at each loci, thereby creating a methylation profile at each time point comprising an aggregation of the methylation signals at each loci (see, e.g., Example 10). The methylation profile can then change over time with each time point represented as an aggregation of the methylation signals at each loci (see, e.g., Example 10).

Quantifying methylation profiles over time can enable monitoring of changes in methylation profiles that are indicative of changes in disease progression. For example, a large increase in the percentage that one or more loci contribute to the methylation profile (i.e., a large increase in the composition of the methylation pattern associated with one or more loci) from one point to another time point may indicate an increase in disease progression (e.g., an increase in tumor size).

In another aspect, this disclosure features a method for quantifying the abundance of a somatic mutation in a sample containing DNA sequences, the method comprising: determining the abundance of the somatic mutation in the sample; quantifying the DNA methylation in the sample comprising the steps of: treating the sample to encode the presence or absence of DNA methylation in the DNA sequences, wherein the sample comprises at least ten target loci from the DNA sequences; adding to the sample a set of synthetic molecules, the set of molecules comprising: target-associated regions having a nucleotide sequence that matches a target sequence region of an endogenous target, and variation regions with a nucleotide sequence that does not match a sequence region of an endogenous target molecule; generating a co-amplification mixture comprising an amplified set of synthetic molecules and an amplified set of at least ten target loci from the DNA sequences; sequencing the co-amplification mixture at a read depth of at least one read sequence per molecule in the sample to generate sequence reads; determining a number of the sequence reads that are methylated sequence reads; quantifying (determining) an absolute number of methylated molecules in the sample based on the number of methylated reads from the sample and a number of reads from the set of synthetic molecules; and returning a true call result for the abundance of the somatic mutation when the number of methylated molecules is above a predetermined or dynamically calculated threshold; and a no-call result for the abundance of the somatic mutation when the number of methylated molecules is at or below the predetermined or dynamically calculated threshold.

In some embodiments, the somatic mutation is selected from one or more of: a single nucleotide variant, a copy number alteration, an insertion, and a deletion.

In some embodiments, determining the abundance of the somatic mutation comprises using a variant allele fraction (VAF).

In some embodiments, the abundance of the somatic mutation indicates the presence of cancer when the abundance of the somatic mutation is at or above a predetermined threshold.

In some embodiments, the method includes, upon returning of a true call and the abundance of the somatic mutation indicates the presence of cancer, performing a treatment selection assay on the subject. In some embodiments, the treatment selection assay comprises genomic profiling to detect novel somatic mutations, the abundance of somatic mutations, or both.

In some embodiments, the method also includes, upon returning of a no-call, repeating the method of determining abundance of a somatic mutation and quantifying DNA methylation on a different sample taken from the subject.

Embodiments of the methods described herein, for example as shown in FIG. 1A, can be performed in any suitable manner. Embodiments of the method as shown in FIG. 1A can include every combination and permutation of the various system components and the various method processes, including any variants (e.g., embodiments, variations, examples, specific examples, figures, etc.), where portions of embodiments of the method and/or processes described herein can be performed asynchronously (e.g., sequentially), concurrently (e.g., in parallel), or in any other suitable order by and/or using one or more instances, elements, components of, and/or other aspects of the system 200 and/or other entities described herein.

Any of the variants described herein (e.g., embodiments, variations, examples, specific examples, figures, etc.) and/or any portion of the variants described herein can be additionally or alternatively combined, aggregated, excluded, used, performed serially, performed in parallel, and/or otherwise applied.

Portions of embodiments of the method as described in FIG. 1A can be embodied and/or implemented at least in part as a machine configured to receive a computer-readable medium storing computer-readable instructions. The instructions can be executed by computer-executable components that can be integrated with the system. The computer-readable medium can be stored on any suitable computer-readable media such as RAMs, ROMs, flash memory, EEPROMs, optical devices (CD or DVD), hard drives, floppy drives, or any suitable device. The computer-executable component can be a general or application specific processor, but any suitable dedicated hardware or hardware/firmware combination device can alternatively or additionally execute the instructions.

As a person skilled in the art will recognize from the previous detailed description and from the figures and claims, modifications and changes can be made to embodiments of the method (e.g., as shown in FIG. 1A), and/or variants without departing from the scope defined in the claims.

6.1. Generating Synthetic Molecules and Adding the Synthetic Molecules to the Sample In some embodiments, the method to quantify DNA methylation in a sample can include: adding, to the treated sample, a set of synthetic molecules (e.g., QCT molecules), the set of synthetic molecules including: target-associated regions with sequence similarity to a target sequence region of endogenous target molecules (e.g., associated with the genetic disorder; etc.), and variation regions (e.g., including embedded molecular identifier (EMI) regions including a set of variable "N" bases, where each "N" base is selected from any one of an "A" base, a "G" base, a "T" base, and a "C" base) with sequence dissimilarity to a sequence region of the endogenous target molecules.

In some embodiments, the methods can include generating a set of QCT molecules, which can function to generate molecules to be used (e.g., added, processed, sequenced, etc.) at one or more stages (e.g., steps, phases, periods, time periods, etc.) of at least one of sequencing library preparation and sequencing (e.g., high-throughput sequencing, etc.), such as for facilitating downstream computational processing (e.g., determining number of QCT sequence reads for facilitating quantifying the number (or percentage) of methylated molecules).

Figure 1B:
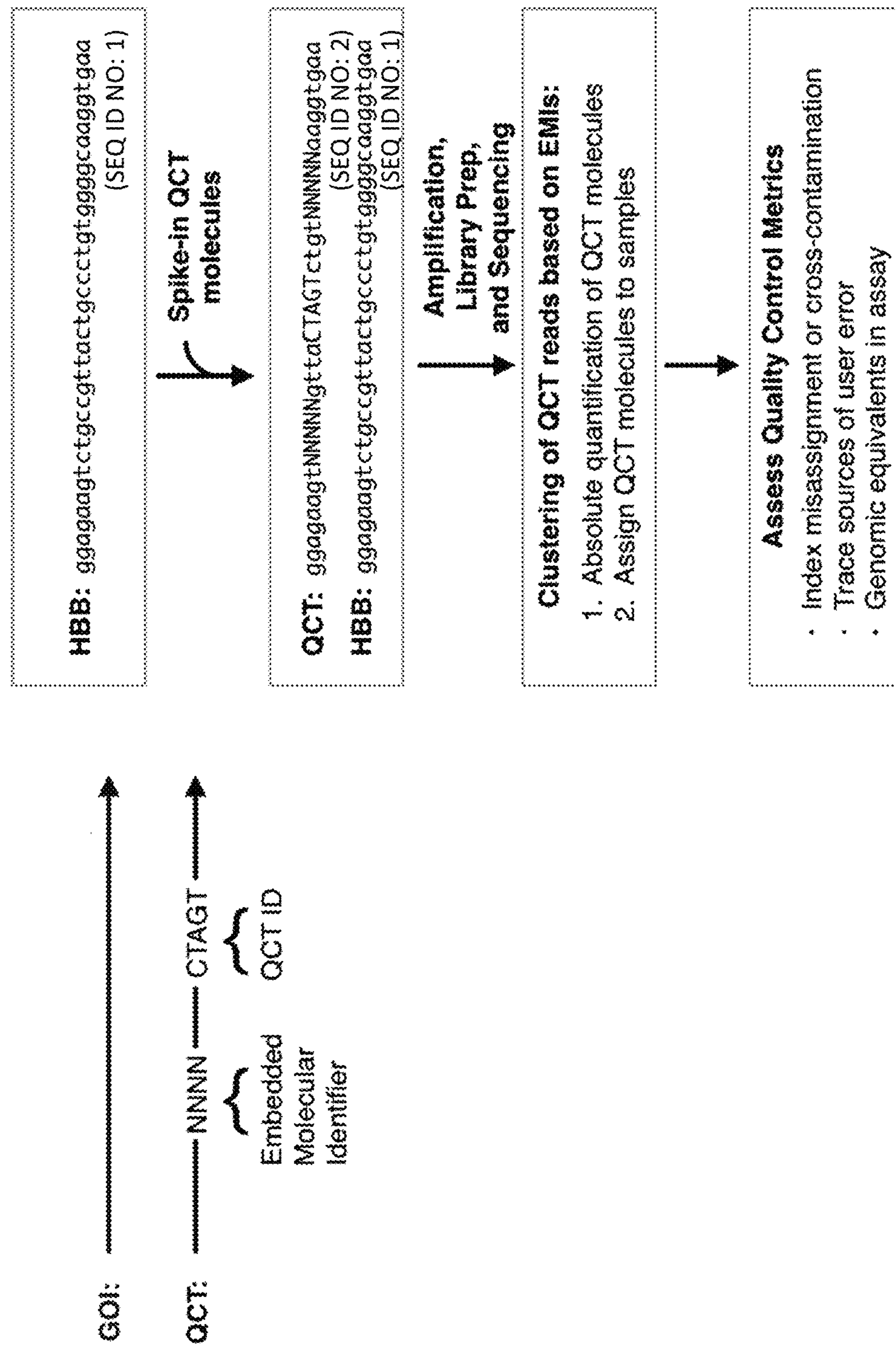
FIG. 1B shows a flowchart representation of a non-limiting embodiment of a method of quantifying DNA methylation in sample.

In some embodiments, synthetic molecules (e.g., QCT molecules) include target-associated regions (e.g., one or more target-associated regions per QCT molecule; etc.). As shown in FIG. 1B, target-associated regions include sequence similarity (e.g., full sequence similarity; sequence similarity satisfying a threshold condition; sequence similarity of a specified number of bases; etc.) to one or more target sequence regions of one or more target molecules (e.g., endogenous target molecules; corresponding to one or more biological targets; etc.), but can additionally or alternatively include any suitable association with any suitable components of one or more target molecules. Target-associated regions preferably enable co-amplification of the corresponding QCT molecules (e.g., including the target-associated regions, etc.) and nucleic acid molecules (e.g., nucleic acids, nucleic acid fragments, etc.) including the target sequence region, which can facilitate improved accuracy in molecular counting (e.g., in determining molecule count parameters; by accounting for amplification biases; etc.), but can additionally or alternatively enable any suitable processes associated with the sequencing library preparation, sequencing, and/or portions of embodiments of the methods described herein. In an example, the methods described herein can include co-amplification of the set of QCT molecules and nucleic acid molecules including the biological target, based on the sequence similarity of the target-associated region and the target sequence region of the biological target, and where quantifying the DNA methylation in the sample can include determining a target molecule count (e.g., methylated molecule count) describing a number of methylated molecules associated with the sequencing, based on the set of synthetic molecules (e.g., QCT sequence read clusters).

In some embodiments, synthetic molecules (e.g., QCT molecules) can omit target-associated regions. For example, QCT molecules can be used with components of samples including biological targets, without target-association (e.g., without having pre-determined similarity to target sequence regions of the biological targets) and/or without corresponding co-amplification with components of the samples (e.g., nucleic acid molecules including the target sequence regions; etc.). In some examples, QCT molecules can be pre-processed to be adapted to sequencing, such as where the pre-processed QCT molecules can be added to a processed sample suitable for sequencing, to be co-sequenced without the need for co-amplification (e.g., for improving user friendliness). QCT molecules omitting target-associated regions are preferably usable for facilitating contamination parameter determination but can additionally or alternatively be used for facilitating any suitable sequencing-related parameter determination. In a specific example, the set of QCT molecules can be adapted for subsequent sequencing (e.g., high-throughput sequencing such as NGS; etc.), where generating the set of QCT molecules can include amplifying a first subset of QCT molecules (e.g., each including a first shared QCT identifier region; etc.) of the set of QCT molecules; and amplifying a second subset of QCT molecules (e.g., each including a second shared QCT identifier region; etc.) of the set of QCT molecules, where the QCT molecule sequencing reads are derived from the sequencing corresponding to: a QCT mixture generated based on the first subset of QCT molecules and the sample including the biological target (e.g., including first target molecules corresponding to the biological target; etc.), and an additional QCT mixture generated based on the second subset of QCT molecules and an additional sample including the biological target (e.g., including second target molecules corresponding to the biological target; etc.), where the sample and the additional sample respectively correspond to a first sample compartment and a second sample compartment of the sample compartments. However, target-associated regions and/or QCT molecules omitting target-associated regions can be configured in any suitable manner.

In some embodiments, synthetic molecules (e.g., QCT molecules) include one or more variation regions (e.g., one or more variation regions per QCT molecule; adjacent variation regions; separated variation regions; etc.). As shown in FIG. 1B, a variation region preferably includes sequence dissimilarity (e.g., complete sequence dissimilarity; dissimilarity of a specified number of bases; partial sequence dissimilarity; etc.) to one or more sequence regions (e.g., distinct from a target sequence region; etc.) of target molecules. A variation region can additionally or alternatively include one or more EMI regions. In a variation, an EMI region can include a set of variable "N" bases (e.g., one or more variable "N" bases, etc.), where each "N" base is selected (e.g., randomly selected; selected according to predetermined statistical distributions and/or probabilities; etc.) from any one of an "A" base, a "G" base, a "T" base, and a "C" base. In a variation, an EMI region can include a synthesized region (e.g., on a microarray; using silicon-based synthesis; etc.) including one or more specified bases (e.g., designed and synthesized bases; etc.), such as synthesized regions designed to facilitate QCT sequence read cluster determination (e.g., by maximizing pairwise hamming distance between EMI regions; etc.). In variations, a QCT molecule can additionally or alternatively include a plurality of EMI regions (e.g., a variation region including a plurality of EMI regions; adjacent EMI regions; separated EMI regions; EMI regions including variable "N" bases; EMI regions including synthesized regions; etc.). For example, each variation region of the set of QCT molecules can include an embedded molecular identifier region including a set of variable "N" bases, where each "N" base is selected from any one of an "A" base, a "G" base, a "T" base, and a "C" base, where each QCT molecule of the set of QCT molecules further includes an additional EMI region including an additional set of variable "N" bases, where the additional EMI region is separated from the EMI region by a sequence region of the QCT molecule, such as where the set of variable "N" bases and the additional set of variable "N" bases can each include a determined (e.g., predetermined) number of "N" bases (e.g., greater than three "N" bases, greater than any suitable number of "N" bases, an exact number of "N" bases; etc.), and where determining a sequencing-related parameter (e.g., contamination parameter) can be based on QCT sequence read clusters derived based on the EMI regions and the additional EMI regions of the set of QCT molecules (e.g., based on distinct EMI sequence reads corresponding to pairs of an EMI region and an additional EMI region; etc.).

In some embodiments, as shown in FIG. 1B, a QCT molecule can include a QCT identifier region identifying the QCT molecule (and/or other suitable QCT molecules), such as a shared QCT identifier region (e.g., a shared sequence region, with dissimilarity to one or more sequence regions of the target molecules, etc.) identifying QCT molecules belong to a set of QCT molecules (e.g., where different QCT identifier regions are unique to different sets of QCT molecules, etc.). In an example, the variation region of the each QCT molecule of a first set of QCT molecules can include a first EMI region separated from a second EMI region by at least a first QCT identifier region, where each additional QCT molecule of a second set of QCT molecules can include a first additional EMI region separated from a second additional EMI region by at least a second QCT identifier region. In an example, the first, the second, the first additional, and the second additional EMI regions can include a set of variable "N" bases, and where each "N" base is selected from any one of an "A" base, a "G" base, a "T" base, and a "C" base, and where computationally determining the set of QCT sequence read clusters can include determining the set of QCT sequence read clusters based on the first and the second QCT identifier regions, and on the first, the second, the first additional, and the second additional EMI regions. In an example, for the each QCT molecule of the first set of QCT molecules, the corresponding QCT molecule sequence is characterized by full sequence similarity to a first sequence template of the biological target except for the first QCT identifier region, the first EMI region, and the second EMI region; and where, for the each additional QCT molecule of the second set of QCT molecules, the corresponding additional QCT molecule sequence is characterized by full sequence similarity to a second sequence template except for the second QCT identifier region, the first additional EMI region, and the second additional EMI region. In a specific example, QCT molecule sequences can be identical to the target molecule sequence (e.g., one or more regions of the target molecule sequence; etc.), except for two separate sections of 5N sequences interrupted by a distinct, previously determined QCT identifier region (e.g., unique identifier sequence, etc.). In a specific example, QCT identifier regions (e.g., unique QCT ID sequence, as shown in FIG. 1B), can be used to enable the use of multiple QCT libraries that can be added at one stage for internal control or at different stages for tracking of loss of input biological targets or other user errors. Additionally or alternatively, QCT identifier regions can be configured in any suitable manner. However, QCT molecules can include any suitable combination of any suitable type of regions (e.g., where different QCT molecules include the same or different types of and/or number of regions; with any suitable sequence similarity and/or dissimilarity to sequence regions of target molecules; etc.).

In some embodiments, the method can additionally or alternatively include generating one or more QCT libraries (e.g., each QCT library including QCT molecules, etc.) such as where a QCT library can include multiple sets of QCT molecules such as where each set of QCT molecules is identifiable by a different QCT identifier region. In an example, generating a QCT library can include amplifying different sets of QCT molecules (e.g., for preparation for sequencing, such as where the QCT molecules are amplified prior to addition to one or more components of a sample to generate a QCT mixture; etc.). In examples, generating a QCT library can include determining a number of QCT molecules to include in the QCT library. In a specific example, the solutions to the birthday problem can be used to determine the maximum number of unique QCT molecules that should be included in each sample given a particular diversity of QCT molecules, such as where, for 4^10 sequences, which can be generated by 10 variable N bases in a QCT molecule, up to 1200 QCT molecules can be used with probability of ~0.5 of a single valid EMI collision (exp(−1200*1199/2/4^10)~0.5), and where at 200 QCT molecules, the probability of a single valid collision is ~2%. In a specific example, generating a QCT library can include generating a QCT library adapted for deployment (e.g., at a single stage of the at least one of the sequencing library preparation and the high throughput sequencing, etc.) of less than 0.00001 nanograms (and/or other suitable amounts) of amplifiable QCT molecules for each sample of a set of samples. However, determining the number of QCT molecules to include in a QCT library, and generating QCT libraries, can be performed in any suitable manner.

In one embodiment, the QCT libraries can be generated by synthesizing complementary strand to single-stranded oligonucleotide sequences that contain variable "N" sequences. In a specific example, double stranded QCT libraries can be generated by re-suspending and annealing the QCT ultramers with a complementary primer sequence, extending the sequences using Klenow Fragment (exo-), and treating with Exonuclease I. The final product can be purified to remove unused single stranded DNA molecules, and QCT libraries can be quantified using fluorometric assays such as Qubit HS assay, from which the number of QCT molecules to be added to each sample can be calculated by using the expected molecular weight of the double-stranded QCT molecules. However, generating QCT molecules can be performed in any suitable manner.

In some embodiments, synthetic molecule libraries (e.g., QCT libraries) can be added at different sequencing library preparation stages (e.g., sample preparation stages) and/or sequencing stages to trace loss-of-sample. In one embodiment, if a first set of QCT molecules (e.g., QCT1 molecules; first QCT molecules including a first shared QCT identifier region; etc.) is dispensed at the point of sample collection, and an equal amount of a second set of QCT molecules (e.g., QCT2 molecules; second QCT molecules including a second shared QCT identifier region; etc.) is dispensed after sample purification (or after treating the sample to encode the presence or absence of DNA methylation), the purification yield (or treatment efficiency yield) may be assessed via comparisons of molecules counts for the first set of QCT molecules and the second set of QCT molecules (e.g., QCT1 vs QCT2 molecule counts, etc.). In one example, the synthetic molecule libraries can be used to trace the efficiency of treating the sample to encode the presence or absence of DNA methylation (i.e., measure bisulfite conversion efficiency).

In some embodiments, the set of synthetic molecules includes: target-associated regions having a nucleotide sequence that matches a target sequence region of an endogenous target, and variation regions with a nucleotide sequence that does not match a target sequence region of an endogenous target molecule. As used herein, the term "matches" refers to sufficient complementarity between two nucleotide sequences where the sequences bind and form the basis for a nucleic acid extension reaction (e.g., amplification). Sufficient complementarity can refer to a match with up to 5 mismatches between the two nucleotide sequences (e.g., the target associated region on a synthetic molecule and the target sequence region on the endogenous target). As used herein, the phrase "does not match" refers to insufficient complementarity between two nucleotide sequences such that sufficient Watson-Crick base pairing is not achieved to enable the two nucleotide sequences to bind and no or little amplification occurs when put into an amplification reaction. Insufficient complementarity can refer to a match with greater than 5 mismatches between the two nucleotide sequences (e.g., the target associated region on a synthetic molecule and the target sequence region on the endogenous target).

6.2. Co-Amplification and Sequencing the Co-Amplification Mixture

In some embodiments, generating a co-amplification mixture comprising an amplified set of synthetic molecules and an amplified set of at least ten target loci from the DNA sequences comprises includes amplifying a synthetic molecule (e.g., QCT molecule) comprising a target-associated region and a nucleic acid molecule (e.g., a nucleic acid that encodes the presence or absence of DNA methylation). For example, target-associated regions preferably enable co-amplification of the corresponding QCT molecules (e.g., including the target-associated regions, etc.) and nucleic acid molecules (e.g., nucleic acids, nucleic acid fragments, etc.) including the target sequence region, which can facilitate improved accuracy in molecular counting (e.g., in determining molecule count parameters; by accounting for amplification biases; etc.), but can additionally or alternatively enable any suitable processes associated with the sequencing library preparation, sequencing, and/or portions of embodiments of the method. In an example, co-amplification of the set of QCT molecules and nucleic acid molecules including the methylated DNA is based on the sequence similarity of the target-associated region and the target sequence region of the methylated DNA.

In some embodiments, the sample includes DNA sequences with loci that are expected to have an increase in DNA methylation in cancerous tissue compared to non-cancerous tissue. Loci that are expected to have an increase in DNA methylation in cancerous tissue compared to non-cancerous tissue are chosen based on, for example and without limitation, a population based survey of methylated loci a patient specific metric (e.g., methylation patterns from a tumor), and/or literature-based studies that identify methylated loci.

In some embodiments, the loci that have an expected increase in DNA methylation in cancerous tissue compared to non-cancerous tissue are amplified and analyzed for the presence of DNA methylation. In some embodiments, the loci that have an expected increase in DNA methylation in cancerous tissue compared to non-cancerous tissue include at least 10, 20, 50, 100, 200, 300, 400, 500, 600, 700, 800, 900, 1000 or more locus, where each locus is expected to have an increase in DNA methylation in cancerous tissue compared to non-cancerous tissue. In some embodiments, the loci that have an expected increase in DNA methylation in cancerous tissue compared to non-cancerous tissue also include loci (e.g., normalization loci) where the DNA sequence is methylated (e.g., highly methylated) in both cancerous tissue and non-cancerous tissue. In such cases, generating a co-amplification mixture results in the co-amplification mixture including: an amplified set of synthetic molecules, an amplified set of a set (e.g., at least ten target loci that have an expected increase in DNA methylation in cancerous tissue compared to non-cancerous tissue), and an amplified set of at least one normalization loci (e.g., a loci that is methylated (e.g., highly methylated) in both cancerous and non-cancerous tissue.

In some embodiments, sequencing (e.g., in relation to 116) associated with one or more embodiments of the method 100 preferably includes high throughput sequencing, which can include and/or be associated with any one or more of: NGS, NGS-associated technologies, massively parallel signature sequencing, Polony sequencing, 454 pyrosequencing, Illumina sequencing, SOLiD sequencing, Ion Torrent semiconductor sequencing, DNA nanoball sequencing, Heliscope single molecule sequencing, Single molecule real time (SMRT) sequencing, Nanopore DNA sequencing, any generation number of sequencing technologies (e.g., second-generation sequencing technologies, third-generation sequencing technologies, fourth-generation sequencing technologies, etc.), amplicon-associated sequencing (e.g., targeted amplicon sequencing), metagenome-associated sequencing, sequencing-by-synthesis, tunneling currents sequencing, sequencing by hybridization, mass spectrometry sequencing, microscopy-based techniques, and/or any suitable technologies related to high throughput sequencing. In some embodiments, sequencing can include any suitable sequencing technologies (e.g., Sanger sequencing, capillary sequencing, etc.).

6.3. Determining Methylated Molecules and Quantifying Methylated Molecules

In some embodiments, determining the number of methylated molecules in the sample based on the number of methylated reads from the sample and the number of reads from the QCT/spike-in at each locus include one or more of target molecule counts (e.g., absolute molecule count of methylated molecules, such as in the original sample; absolute count of endogenous target molecules, such as in the original sample; etc.); reference molecule counts (e.g., absolute count of endogenous reference molecules; such as in the original sample; etc.); QCT molecule counts (e.g., corresponding to a number of valid QCT sequence read clusters; corresponding to a number of distinct QCT molecules added to components of the sample; etc.); associated ratios (e.g., correction factors; ratios between a molecule count and an associated number of sequence reads; etc.); and/or any other suitable parameters associated with methylated molecule counts.

As show in FIG. 1A, methylated molecule counts are preferably used in facilitating one or more diagnoses 122, but can additionally or alternatively be used for (e.g., as inputs for) any suitable portions of embodiments of the method 100, including facilitating treatment of one or more conditions 124.

In some embodiments, determining a methylated molecule count parameter (e.g., methylated molecule count; etc.) can be based on a correction factor ratio determined based on a QCT molecule count (e.g., corresponding to a number of QCT sequence read clusters, such as a number of valid QCT sequence read clusters; etc.) and QCT molecule sequence reads (e.g., a number of the QCT molecule sequence reads corresponding to the QCT sequence read clusters; etc.), such as by multiplying the number of methylated molecule sequence reads by the correction factor ratio. In a specific example, the number of valid non-contaminating QCT sequence read clusters (e.g., remaining QCT sequence read clusters after discarding the QCT sequence read clusters with 2 or fewer reads, and/or with any suitable number or fewer of reads; etc.) can indicate the QCT molecule count (e.g., the number of QCT molecules for a particular sample compartment; for a particular sample; for a particular sample identifier; etc.). In a specific example, by dividing the QCT molecule count by the sequencing reads resulting from the corresponding QCT molecules, the correction factor can be found, such as where the correction factor multiplied by the sequencing reads belonging to the target molecules (e.g., in the particular sample compartment; from the particular sample; associated with the particular sample identifier; etc.) would result a target molecule count (e.g., an absolute number of initial biological target molecules that were accessible by the assay for amplification; etc.). In an example, the average QCT sequencing depth used in determining the absolute count of the endogenous target molecules and the absolute count of endogenous reference molecules is determined separately from their corresponding QCTs.

Alternatively, in one embodiment, the read depth threshold for discarding QCT sequence read clusters (e.g., for determining molecule count parameters and/or suitable sequencing-related parameters; etc.) can be determined adaptively based on features of QCT molecule sequence read (e.g., EMI sequence read) depth distribution. For example, a threshold may be set for each indexed sample by computing the mean EMI read depth within each sample, computing the square-root of this mean read depth, and discarding QCT sequence read clusters with read depth below the square-root of the mean read depth. Additionally or alternatively, read depth thresholds for discarding QCT sequence read clusters can be computed in any suitable manner. However, determining methylated molecule count can be performed in any suitable manner.

In some embodiments, variant calling comprises determining the variant allele frequency (VAF) of the DNA variant. As used herein, "variant allele frequency" or "variant allele fraction" refers to the percentage of sequence reads observed matching a specific DNA variant divided by the overall coverage at that locus.

In some embodiments (e.g., of quantifying DNA methylation), the method in FIG. 1A can be used a) to determine parameters for use in algorithms for determining the diagnostic outcome of assays, b) to track the loss of input methylated DNA (e.g., at different stages of the assay), c) to return a no-call result when the number of methylated molecules is too low (e.g., to determine when an assay is not reliable, etc.), d) to return a no-call result when a corresponding quantification of an abundance of somatic mutation(s) in a sample is too low (e.g., to determine when an assay is not reliable), e) to design assays for detecting changes in methylation profiles over, and/or f) aiding therapeutic and clinical decision-making based on the results of diagnostic assays.

Embodiments can additionally or alternatively determine the portion of biological material that is accessible by the assay, such as through quantification of the biological targets (e.g., methylated molecules) based on using the QCT molecules, which can improve upon measuring the total genomic material available and calculating the expected biological target (e.g., methylated molecules) concentration, due to not all targets being accessible by assays. In a specific example, this may be due to shearing of DNA to a short size distribution, as in the case of circulating free DNA that is assayed in applications of liquid biopsy applications where circulating tumor DNA is assayed.

Some embodiments of the methods provided herein (see, e.g., FIG. 1A) can be used in association with one or more conditions (e.g., in association with characterizing, diagnosing, treating, and/or performing processes related to one or more conditions; etc.), where the conditions can include and/or otherwise be associated with cancer (e.g., through analyses associated with any suitable oncogenes, cancer biomarkers, and/or other cancer-associated targets; through analyses associated with liquid biopsies), and/or any other suitable conditions. In an example, the method (of FIG. 1A and/or as described herein) can include determining a methylated molecule count (e.g., corresponding to a number of methylated molecules in a sample; based on use of QCT molecules; etc.) for facilitating diagnosis associated with liquid biopsies.

In some embodiments, the number of methylated molecules for the cfDNA and the number of methylated molecules for gDNA are quantified in the same workflow. For example, methylated molecules of cfDNA and methylated molecules of gDNA can be indexed (e.g., using defined index sequences) in order to be able to differentiate between the source of methylated molecules (e.g., cfDNA versus gDNA). This enables the cfDNA and gDNA to be amplified and/or sequenced in the same reaction (e.g., multiplexing).

6.4. Processing the Methylated Sequencing Reads

Some embodiments of the methods provided herein (see, e.g., FIG. 1A) include a step of processing the methylated sequence reads. In some embodiments, processing of the methylated sequence reads includes filtering out selected hypermethylated target loci; and/or subtracting background methylation. The processing step (e.g., filtering out selected hypermethylated target loci and/or subtracting background methylation) can be performed prior to determining the number of methylated molecules in the sample based on the number of methylated reads from the sample and a number of sequence reads from the set of synthetic molecules. The processing step (e.g., filtering out selected hypermethylated target loci and/or subtracting background methylation) can be performed prior to determining the number of molecules in the number of methylated molecules in the sample based on the number of methylated reads from the sample and a number of sequence reads from the set of synthetic molecules but prior to an aggregating step.

In some embodiments, the step of subtracting background methylation includes subtracting the number of methylated molecules as measured in the buffy coat (i.e., gDNA) from the number of methylated molecules in the cfDNA. In such cases, methylated molecules are quantified for both cfDNA and gDNA. For example, methylation measured in gDNA is then subtracted from cfDNA methylation in order to remove background from the cfDNA methylation signal. In some embodiments, the step of background subtraction includes subtracting the number of methylated molecules as measured in the buffy coat (i.e., gDNA) from the number of methylated molecules in the cfDNA on a per-locus basis. For example, methylation measured in gDNA for a particular target loci is subtracted from cfDNA methylation measured for the same target loci in order to remove background from the cfDNA methylation signal on a per-locus basis.

In some embodiments, the step of filtering out selected hypermethylated target loci comprises filtering out target loci having a total number of methylated molecules in the buffy coat above a threshold (e.g., a predetermined number of quantified methylated molecules). In some embodiments, the step of filtering out selected hypermethylated target loci can include filtering out target loci with high background methylation prior to quantifying the number of methylated molecules in the sample. In some embodiments, the selected hypermethylated target loci that are filtered out include target loci having a high methylation cfDNA signal in non-cancer subjects. In some embodiments, the selected hypermethylated target loci are selected from a global blacklist (see, e.g., Example 6). In some embodiments, the selected hypermethylated target loci are selected from a personal blacklist (see, e.g., Example 6).

In some embodiments, the selected hypermethylated target loci that are filtered out include target loci having a number (e.g., a total number) of methylated molecules in the buffy coat above a threshold. In some embodiments, the threshold is sample specific (e.g., the number of methylated molecules in the buffy coat is determined for each sample). In some embodiments, the threshold is subject-specific (e.g., the number of methylated molecules in the buffy coat is determined for each subject). In some embodiments, the threshold includes a pre-determined mean tumor methylated quantitative equivalent (QE), a predetermined max tumor methylated QE, or a combination thereof. Quantitative equivalents (QE) is an estimate of the number of genomic equivalents of a locus based on QCT analysis. In some embodiments, the threshold includes a max tumor QE in any non-cancer specimen of >15, where a hypermethylated target loci having a max tumor QE of greater than 15 in any non-cancer specimen is filtered out. In some embodiments, the threshold includes a mean tumor QE (including 0s)>2, where a hypermethylated target loci having a mean tumor QE>2 is filtered out.

6.5. Aggregating and Normalizing

Some embodiments of the methods provided herein (see, e.g., FIG. 1A) include a step of aggregating the number of methylated molecules across all or a subset of the target loci (e.g., a subset of the at least ten target loci) to quantify DNA methylation in a sample. In some embodiments, aggregating comprises aggregating the number of methylated molecules across at least two target loci (e.g., at least two of the at least ten target loci) to quantify the DNA methylation in the sample. In some embodiments, the method includes aggregating the methylated molecules in the cfDNA (plasma) sample across at least two loci (e.g., at least two of the at least ten target loci). In some embodiments, the method includes aggregating the methylated molecules in the buffy coat (gDNA) sample across at least two loci (e.g., at least two of the at least ten target loci).

In some embodiments, aggregating the number of methylated molecules across all or a subset of the target loci (e.g., all or a subset of the at least ten target loci) comprises aggregating target loci that contain lower than a threshold amount of methylated molecules in the buffy coat sample. The threshold of amount of methylated molecules in the buffy coat sample can be predetermined or dynamically calculated. A dynamically calculated threshold is a threshold that is not fixed but varies based on certain conditions or inputs. In the case of a threshold amount of methylated molecules, the threshold can be dynamically calculated based on factors such as the size of the system being studied, the concentration of molecules present, or the sensitivity of the detection method used to measure the molecules. For example, in a sample (e.g., a blood draw) the threshold amount of methylated molecules may vary depending on cancer type or the stage of the cancer.

Some embodiments of the methods provided herein (see, e.g., FIG. 1A) include a step of normalizing the aggregate number of methylated molecules to help quantify the DNA methylation in a sample. In one embodiment, the method includes normalizing the aggregate number of target methylated molecules by the methylated molecules in the normalization loci (e.g., methylated molecules for at least one normalization loci). In some embodiments, the method includes normalizing the aggregate number of target methylated molecules by the aggregate number of methylated molecules in the normalization loci. In such cases, the method includes aggregating the number of methylated molecules across at least two normalization loci. In some embodiments, the method includes normalizing the aggregate number of methylated molecules from at least two of the at least 10 target loci by the methylated molecules for the at least one normalization locus.

The aggregating and/or normalizing steps enable quantification of a tumor methylation score that represents the normalized sum of methylated molecules (e.g., at at least ten target loci) that are hypermethylated in the sample.

Some embodiments of the methods provided herein (see, e.g., FIG. 1A) can be used for quantifying the abundance of tumor DNA in a sample (see, e.g., Section 6.8).

Some embodiments of the methods provided herein (see, e.g., FIG. 1A) can be used for determining DNA methylation profile in a subject (see, e.g., Section 6.9).

Some embodiments of the methods provided herein (see, e.g., FIG. 1A) can be used for quantifying the abundance of a somatic mutation in a sample (see, e.g., Section 6.10).

Additionally or alternatively, data described herein (e.g., sequencing-related parameters, identifiers, read depths, sequence reads, sequence region determinations, QCT molecule designs, primer designs, etc.) can be associated with any suitable temporal indicators (e.g., seconds, minutes, hours, days, weeks, time periods, time points, timestamps, etc.) including one or more: temporal indicators indicating when the data was collected, determined, transmitted, received, and/or otherwise processed; temporal indicators providing context to content described by the data, such as temporal indicators indicating the sequence of stages of sequencing library preparation and/or sequencing; changes in temporal indicators (e.g., data over time; change in data; data patterns; data trends; data extrapolation and/or other prediction; etc.); and/or any other suitable indicators related to time.

Additionally or alternatively, parameters, metrics, inputs, outputs, and/or other suitable data described herein can be associated with value types including any one or more of: scores, binary values, classifications, confidence levels, identifiers (e.g., sample identifiers, QCT molecule identifiers, etc.), values along a spectrum, and/or any other suitable types of values. Any suitable types of data described herein can be used as inputs, generated as outputs, and/or manipulated in any suitable manner for any suitable components associated with embodiments of the method 100 and/or system 200.

In some cases the embodiments as described in FIG. 1B can additionally or alternatively include a sample handling network configured to generate molecules (e.g., QCT molecules; QCT libraries; etc.), process biological samples, and/or perform other suitable processes; a sequencing system configured to sequence processed genetic material from mixtures generated based on biological samples and QCT molecules; a computing system (e.g., a remote computing system; a local computing system; etc.) configured to analyze the sequence reads, determine QCT sequence read clusters, determine sequencing-related parameters, facilitate diagnoses, facilitate treatment, and/or perform other suitable processes (e.g., computational processes); and/or any other suitable components. The components of the system in FIG. 1B can be physically and/or logically integrated in any manner (e.g., with any suitable distributions of functionality across the components, such as in relation to portions of embodiments of the method in FIG. 1A; etc.). However, the method FIG. 1A and system FIG. 1B can be configured in any suitable manner.

6.6. Facilitating Diagnosis, Treatment, or Additional Assessment

In one aspect, this disclosure features a method (FIG. 1A) that can additionally or alternatively include facilitating diagnosis 122, which can function to aid, determine, provide, and/or otherwise facilitate one or more diagnoses for one or more conditions.

Facilitating one or more diagnoses can include any one or more of determining one or more diagnoses (e.g., based on number of methylated molecules; etc.); providing one or more diagnoses (e.g., to one or more users; to one or more care providers, such as for use by one or more care providers in providing medical diagnoses to patients; etc.); aiding one or more diagnoses (e.g., providing one or more sequencing-related parameters and/or other suitable parameters to one or more care providers and/or other suitable entities, for use in determining a diagnosis, such as in combination with other data; etc.); and/or any suitable processes associated with diagnoses. For example, aiding diagnosis can include providing a quantification of DNA methylation in a sample from a patient (e.g., to a user; to a care provider; etc.) adapted for use in determination of a diagnostic outcome for assays associated with liquid biopsies. In an example, quantifying DNA methylation can include quantifying the number of methylated molecules in the sample, (e.g., the absolute number of methylated molecules in the sample) for facilitating diagnosis associated with liquid biopsies.

In some embodiments, facilitating diagnosis (e.g., cancer diagnosis) can include facilitating diagnosis based on the amount of methylated molecules in the sample (see FIG. 1A, 122). For example, determining the absolute number of methylated molecules can include determining the absolute number of methylated molecules associated with a DNA sequence, based on dividing the total read count for the methylated molecules by the average QCT sequencing depth, where determining the absolute number of methylated molecules can include determining the absolute number of methylated molecules associated with a second DNA sequence not expected to have a methylation, based on dividing the total read count for the methylated molecules by the average QCT sequencing depth, and where facilitating the diagnosis (e.g., the cancer diagnosis) can include facilitating the diagnosis (e.g., cancer diagnosis; etc.) of the methylated molecule based on the comparison.

In some embodiments, facilitating diagnosis (e.g., cancer diagnosis) can include facilitating diagnosis based on the amount of methylated molecules in the sample (see FIG. 1A, 122). For example, determining the absolute number of methylated molecules can include determining the absolute number of methylated molecules, based on dividing the total read count for the methylated molecules by the average QCT sequencing depth, where determining the absolute count of the methylated molecules can include determining the absolute count of the methylated molecules in a sample not expected to have methylated sequence at the same correspond DNA sequence, based on dividing the total read count for the methylated molecules by the average QCT sequencing depth, and where facilitating the diagnosis (e.g., cancer diagnosis) can include facilitating the diagnosis (e.g., cancer diagnosis) of the methylated molecules based on the comparison.

In one aspect, this disclosure features a method (FIG. 1A) that can additionally or alternatively include facilitating treatment 124. For example, the methods described herein, including: the quantification of DNA methylation, the determination of a DNA methylation profile, and/or the quantification of the abundance of a somatic mutation can be used to assess whether a cancer treatment has been effective for a particular patient. The results provided by the methods described herein can help inform an oncologists future treatment decisions. In one example, where a method to quantify DNA methylation in a sample results in the discovery of increase DNA methylation in a subject, the subject's oncologist can use the quantified DNA methylation increase as a basis, in part, for adjusting the subject's treatment regimen. In another example, where a method to determine the methylation profile in a sample results in the discovery of a change in the DNA methylation profile indicative of a change in the subject's cancer, the subject's oncologist can use the change in DNA methylation profile as a basis, in part, for adjusting the subject's treatment regimen. In another example, where a method for quantifying the abundance of a somatic mutation in a sample results in the discovery of somatic mutations indicative of cancer and/or a change in the cancer, the subject's oncologist can use the quantification of the abundance of the somatic mutation as a basis, in part, for adjusting the subject's treatment regimen.

In one embodiment, this disclosure features a method that can additionally or alternatively include recommending additional assessment of the subject based on, which can function to aid, determine, provide, and/or otherwise facilitate diagnosis or treatment. For example, the methods described herein, including: the quantification of DNA methylation, the determination of a DNA methylation profile, and/or the quantification of the abundance of a somatic mutation can be used as the basis for making additional assessments of the subject or recommending that additional assessments of the subject. In some cases, making an additional assessment includes subjecting the subject to a treatment selection assay. In some cases, making an additional assessment includes subjecting the subject to a genomic profiling assay (i.e., an assay to assess mutation profile of the subject).

In one embodiment, the quantified DNA methylation in a sample collected from a subject, quantified according to the methods described herein, can be incorporated into a clinical recommendation for the subject. A clinical recommendation can include a plan for further testing or treatment: For example, based on the quantified DNA methylation in the sample and the clinical implications of the DNA methylation, a plan for further testing or treatment can be developed. In some cases, this may involve additional testing to confirm the diagnosis, monitoring for disease progression or recurrence, or prescribing targeted therapies that are specific to the subject's DNA methylation profile.

6.7. Quantifying DNA Methylation in Sample

This disclosure also features methods to quantify DNA methylation in a sample comprising DNA sequences.

In some embodiments, the method includes: treating the sample to encode the presence or absence of DNA methylation in the DNA sequences. In other embodiments the sample has already been treated to encode the presence or absence of DNA methylation in the DNA sequences.

In some embodiments, the sample (e.g., the sample containing a mixture of methylated and unmethylated DNA sequences) may include at least ten target loci from the DNA sequences (e.g., loci that are amplified and assessed to quantify methylation). In some cases, each locus of the at least ten target loci is chosen due to an expected increase in DNA methylation at each loci in cancerous tissues compared to normal tissue. The sample can also include normalization loci (e.g., loci that are highly methylated in both cancerous tissues and normal tissue (e.g., non-cancerous tissue)). In some cases, the normalization loci are included in the target loci (e.g., the at least ten target loci). The method also includes adding to the sample a set of synthetic molecules that include target-associated regions having a nucleotide sequence that matches a target sequence region of an endogenous target molecule (wherein the endogenous target molecule comprises at least one of the target loci), having at least one of the target loci, and variation regions with sequence that does not match a sequence region of an endogenous target molecule. The method further includes generating a co-amplification mixture comprising an amplified set of synthetic molecules and an amplified set of at least ten target loci from the DNA sequences. In some embodiments, the co-amplification mixture comprises at least one normalization locus that is expected to have high methylation in cfDNA across both cancerous and non-cancerous tissues. The method includes sequencing the co-amplification mixture to generate sequence reads, and determining a number of the sequence reads that are methylated sequence reads. The method additionally includes quantifying (determining) a number (e.g., an absolute number) of methylated molecules in the sample (e.g., for each locus) based on the number of methylated reads from the sample (e.g., from each locus) and a number of reads from the set of synthetic molecules. In one embodiment, the method includes quantifying (determining) a number (e.g., an absolute number) of methylated molecules in the sample for each target loci based on the number of methylated reads from the sample for each target loci and a number of reads from the set of synthetic molecules. In some embodiments, the method further comprises aggregating the number of methylated molecules across at least two of the at least ten target loci to quantify the DNA methylation in the sample.

In another embodiment, this disclosure also features methods for quantifying DNA methylation in a sample containing cell free DNA (cfDNA) sequences. In some embodiments, the quantified DNA methylation is a tumor methylation score. The method includes treating the sample (e.g., wherein the sample is taken from a blood draw that includes plasma having cfDNA and buffy coat having genomic DNA (gDNA)) to encode the presence or absence of DNA methylation in the DNA sequences (e.g., the cfDNA and/or the gDNA sequences). The sample (e.g., the sample containing a mixture of methylated and unmethylated DNA sequences) may include at least ten target loci from the DNA sequences (e.g., loci that are amplified and assessed for the presence of methylation). In some cases, each locus of the at least ten target loci is chosen due to an expected increase in DNA methylation at each loci in cancerous tissues compared to normal tissue (e.g., non-cancerous tissue). The sample can also include normalization loci (e.g., loci that are highly methylated in both cancerous tissues and normal (e.g., non-cancerous) tissue). A set of synthetic molecules is added to the sample, where the set of molecules include: target-associated regions having a nucleotide sequence that matches a target sequence region of an endogenous target, and variation regions with a nucleotide sequence that does not match a sequence region of an endogenous target molecule. The sample containing the synthetic molecules is amplified thereby generating a co-amplification mixture that includes an amplified set of synthetic molecules, and an amplified set of at least ten target loci from the DNA sequences, which optionally includes normalization loci. The method includes sequencing the co-amplification mixture at a read depth of at least one read sequence per molecule in the sample to generate sequence reads and determining a number of the sequence reads that are methylated sequence reads. The method also includes processing the methylated sequence reads using one or more of the following: filtering out selected hypermethylated target loci (e.g., filtering out target loci having a total number of methylated molecules in the buffy coat above a threshold); and/or subtracting background methylation (e.g., subtracting background methylation comprises subtracting the number of methylated molecules as measured in the buffy coat from the number of methylated molecules in the cfDNA (e.g., on a per-locus basis)). The method further includes quantifying (determining) a number (e.g., an absolute number) of methylated molecules in the sample based on the number of methylated reads from the sample and a number of sequence reads from the set of synthetic molecules. In one embodiment, the method includes quantifying (determining) a number (e.g., an absolute number) of methylated molecules in the sample for each target loci based on the number of methylated reads from the sample for each target loci and a number of reads from the set of synthetic molecules. In some embodiments, the method also includes aggregating the number of methylated molecules across at least two of the at least ten target loci to quantify DNA methylation in the DNA sample. In some embodiments, the sample is taken from a blood draw comprising plasma and buffy coat, where the plasma includes cfDNA sequences and the buffy coat comprises gDNA.

In one embodiment, the method includes determining (quantifying) the number of methylated molecules in cfDNA and/or gDNA using QCT molecular counting technology (e.g., as described in U.S. Pat. Pub. 2019/0211395A1, which is incorporated by reference) at the at least ten target loci, where each locus of the at least ten target loci is chosen due to an expected increase in DNA methylation at each loci in cancerous tissues compared to normal (e.g., non-cancerous) tissue. In such embodiments, the number of methylated molecules for cfDNA and the number of methylated molecules for gDNA are each quantified (e.g., in separate workflows) by treating the sample to encode the presence or absence of DNA methylation in the DNA sequences, where the sample comprises at least ten target loci from the DNA sequences; adding to the sample a set of synthetic molecules, the set of molecules comprising: target-associated regions having a nucleotide sequence that matches a target sequence region of an endogenous target and, and variation regions with a nucleotide sequence that does not match a sequence region of an endogenous target molecule; generating a co-amplification mixture comprising an amplified set of synthetic molecules and an amplified set of at least ten target loci (or a subset thereof) from the DNA sequences; sequencing the co-amplified mixture (e.g., at a read depth of at least one read sequence per molecule in the sample) to generate sequence reads; determining a number of the sequence reads that are methylated sequence reads; and quantifying (determining) a number (e.g., an absolute number) of methylated molecules in the sample based on the number of methylated reads from the sample and a number of reads from the set of synthetic molecules.

In some embodiments, quantifying DNA methylation in a sample includes quantifying the number of methylated molecules for the cfDNA and the number of methylated molecules for gDNA, which can be quantified in the same workflow. In one embodiment, methylated molecules of cfDNA and methylated molecules of gDNA can be indexed (e.g., using defined index sequences) in order to be able to differentiate between the source of methylated molecules (e.g., cfDNA versus gDNA), thereby enabling the cfDNA and gDNA to be amplified and/or sequenced in the same reaction (e.g., multiplexing).

In one embodiment, quantifying DNA methylation in a sample containing gDNA sequences from buffy coat includes: treating a sample that includes methylated and unmethylated gDNA sequences from buffy coat to encode the presence or absence of DNA methylation in the gDNA sequences. In such cases, the sample includes at least ten target loci from the gDNA sequences, wherein each locus of the at least ten target loci is chosen due to an expected increase in DNA methylation at each loci in cancerous tissues compared to normal tissue and are the same target loci analyzed in the cfDNA extracted from plasma. The method includes adding to the sample a set of synthetic molecules, the set of molecules comprising: target-associated regions having a nucleotide sequence that matches a target sequence region of an endogenous target and variation regions with a nucleotide sequence that does not match a sequence region of an endogenous target molecule. The method also includes generating a co-amplification mixture comprising an amplified set of synthetic molecules and an amplified set of at least ten target loci from the DNA sequences and sequencing the co-amplification mixture to generate sequence reads. Further, the method includes determining a number of the sequence reads that are methylated sequence reads; and quantifying (determining) a number of methylated molecules in the sample based on the number of methylated reads from the sample and a number of reads from the set of synthetic molecules. Optionally, the method includes aggregating the number of methylated molecules across at least two of the at least ten target loci to quantify DNA methylation in the sample containing DNA sequences from the buffy coat.

In some embodiments, methods for quantifying DNA methylation in a sample include addition of a spike-in of known sequence and quantity to the sample prior to the treating step. The spike-in comprises a known sequence having unmethylated cytosines that are converted to uracils upon being subjected to the treating step. The initial number of spike-in molecules can be calculated as well as the percent of cytosine bases that were converted to thymine/uracil bases. This enables calculation of the bisulfite conversion yield and conversion efficiency, thereby establishing bisulfite conversion QC metrics, and therefore determining whether a sample failed the bisulfite conversion step (i.e., step of treating the sample containing DNA sequences to encode the presence or absence of DNA methylation in the DNA sequences).

In some embodiments, the method for quantifying DNA methylation in a sample includes a step of processing the methylated sequence reads by one or more of the following: filtering out selected hypermethylated target loci (e.g., filtering out target loci having a total number of methylated molecules in the buffy coat above a threshold); or subtracting background methylation (e.g., subtracting the number of methylated molecules as measured in the buffy coat from the number of methylated molecules in the cfDNA, which can be done a per-locus basis). In some embodiments, processing is performed prior to the step of quantifying the number (e.g., the absolute number) of methylated molecules in the sample. In some embodiments, filtering hypermethylated target loci, subtracting background methylation, or both, are performed prior to quantifying the number of methylated molecules in the sample.

In some embodiments, methods for quantifying DNA methylation in a sample include a step of further comprising aggregating the number of methylated molecules across at least two of the at least ten target loci to quantify the DNA methylation in the sample. Aggregation can include aggregating target loci that contain lower than a threshold amount of methylated molecules in the buffy coat sample.

In some embodiments, methods for quantifying DNA methylation in a sample include aggregating the number of methylated molecules across the at least ten target loci (or a subset thereof, e.g., at least two target loci); and normalizing the aggregate number of methylated molecules from all or a subset of the at least 10 target loci by the methylated molecules for the at least one normalization locus. In some embodiments, this results in quantification of DNA methylation (e.g., a tumor methylation score) that represents the normalized sum of methylated molecules (e.g., at the at least ten target loci that are hypermethylated in the sample.

In some embodiments, aggregating the number of methylated molecules across the at least ten target loci (or a subset thereof, e.g., at least two target loci)) includes aggregating at least one target loci that demonstrates high methylation in the sample containing DNA sequences.

In one embodiment, the method further comprises determining cancer tissue of origin by quantifying methylation in a DNA sample, wherein determining the cancer tissue of origin comprises: determining the number of methylated molecules in the sample based on the number of methylated reads from the sample and the number of reads from the set of synthetic molecules at each locus; and determining the tissue of origin based on an abundance of methylated molecules across loci.

6.8. Quantifying Tumor DNA in a Sample

This disclosure also features methods for quantifying the amount of tumor DNA in a sample containing DNA sequences. The method includes: adding to the sample (e.g., wherein the sample is taken from a blood draw that includes plasma having cfDNA and buffy coat having genomic DNA (gDNA)) a set of synthetic molecules, the set of molecules comprising: target-associated regions having a nucleotide sequence that matches a target sequence region of an endogenous target (e.g., comprising at least one target loci), and variation regions with a nucleotide sequence that does not match a sequence region of a endogenous target molecule. The method includes generating a co-amplification mixture comprising an amplified set of synthetic molecules, an amplified set of at least 10 target loci from the DNA sequences, and optionally an amplified one or more normalization locus; sequencing the co-amplification mixture at a read depth of at least one read sequence per molecule in the sample to generate sequence reads; quantifying (determining) a number of molecules containing a somatic mutation in the sample based on the number of reads from the sample containing a somatic mutation and the number of reads from the set of synthetic molecules.

6.9. Determining a Methylation Profile in a Subject Over Time

This disclosure also features methods for determining a DNA methylation profile in a subject over time. Determining a methylation profile in a subject over time using serial quantification of DNA methylation enables early indication of the response or progression of the cancer to therapy (or reoccurrence). As provided described herein, the instant methods uniquely enable this type of serial quantification of DNA methylation.

In one embodiment, a method for determining a DNA methylation profile in a subject over time includes quantifying DNA methylation a first time point and a second time point; and determining whether the methylation (which is a proxy tumor measurement) has changed over time (e.g., increased or decreased compared to the measuring at a first time point). In some cases, the change in DNA methylation (i.e., Tumor Methylation Score) exceeds a significance threshold and is reported as an increase or a decrease. In some embodiments, the methods for determining a DNA methylation profile in a subject over time can distinguish a 0.2 percentage point change (or lower (e.g., 0.1, 0.05, 0.01, 0.05, 0.001 percent change) in DNA methylation (e.g., number of methylated molecules) with 3 standard deviations of separation.

In some embodiments, a method for determining a DNA methylation profile in a subject over time includes: i) treating a sample isolated from subject to encode the presence or absence of DNA methylation in the DNA sequences, wherein the sample comprises at least ten target loci from the DNA sequences, where each locus of the at least ten target loci is chosen based on an expected increase in DNA methylation at each loci in cancerous tissue compared to non-cancerous tissue and the sample optionally includes normalization loci (e.g., loci that are highly methylated in both cancerous tissues and normal tissue (e.g., non-cancerous) tissue); ii) adding to the sample a set of synthetic molecules (e.g., QCT molecules), the set of molecules comprising: target-associated regions having a nucleotide sequence that matches a target sequence region of an endogenous target molecule comprising at least one of the target loci, and variation regions with a nucleotide sequence that does not match a sequence region of an endogenous target molecule; iii) generating a co-amplification mixture comprising an amplified set of synthetic molecules and an amplified set of at least ten target loci from the DNA sequences; iv) sequencing the co-amplification mixture at a read depth of at least one read sequence per molecule in the sample to generate sequence reads; v) determining a number of the sequence reads that are methylated sequence reads; vi) quantifying (determining) a number of methylated molecules (e.g., for each target loci) in the sample based on the number of methylated sequence reads (e.g., from each target loci) in the sample and a number of reads from the set of synthetic molecules; repeating steps i) to vi) at a second time point; and determining the methylation pattern in the subject based on the number of methylated molecules (e.g., for each target loci) in the sample at the first time point and the number of methylated molecules (e.g., for each target loci) in the sample at the second time point. In some embodiments, the sample has already been treated to encode the presence or absence of DNA methylation in the DNA sequences, and therefore, step i) is not performed.

In some embodiments, determining the methylation profile in the subject at the first time point and the second time point identifies a change in the methylation profile.

In one embodiment, methods for determining a DNA methylation profile in a subject over time include repeating steps i) to vi) at a third time point; and determining the methylation profile in the subject based on the number of methylated molecules (e.g., for each target loci) in the sample at the third time point.

In some embodiments, determining the methylation profile in the subject at the first time point, the second time point, and the third time point identifies a change in the methylation profile between the first and second time points, the second and third time points, the first and third time points, or a combination thereof.

In one embodiment, methods for determining a DNA methylation profile in a subject over time includes quantifying the number of methylated molecules in both cfDNA (plasma) and gDNA (buffy coat) using QCT molecular counting technology (e.g., as described in U.S. Pat. Pub. 2019/0211395A1, which is incorporated by reference) at the at least ten target loci, where each locus of the at least ten target loci is chosen due to an expected increase in DNA methylation at each loci in cancerous tissues compared to normal (e.g., non-cancerous) tissue. In such embodiments, the number of methylated molecules for cfDNA is quantified as described herein (see Section 6.7) and the number of methylated molecules for gDNA are each quantified as described herein (see Section 6.7).

In some embodiments, methods for determining a DNA methylation profile in a subject over time include addition of a spike-in of known sequence and quantity to the sample prior to the treating step at each time point. The spike-in comprises a known sequence having unmethylated cytosines that are converted to uracils upon being subjected to the treating step, which enables calculation of the bisulfite conversion yield and conversion efficiency, thereby establishing bisulfite conversion QC metrics that can be used to determine if a sample failed the bisulfite conversion step.

In some embodiments, methods for determining a DNA methylation profile in a subject over time include a step of processing the methylated sequence reads by one or more of the following: filtering out selected hypermethylated target loci (e.g., filtering out target loci having a total number of methylated molecules in the buffy coat above a threshold); or subtracting background methylation (e.g., subtracting the number of methylated molecules as measured in the buffy coat from the number of methylated molecules in the cfDNA, which can be done a per-locus basis). In some embodiments, processing is performed prior to the step of quantifying the number (e.g., the absolute number) of methylated molecules in the sample. In some embodiments, filtering hypermethylated target loci, subtracting background methylation, or both, are performed prior to quantifying the number of methylated molecules in the sample.

In some embodiments, methods for quantifying DNA methylation in a sample include a step of further comprising aggregating the number of methylated molecules across at least two of the at least ten target loci to quantify the DNA methylation in the sample. Aggregation can include aggregating target loci that contain lower than a threshold amount of methylated molecules in the buffy coat sample.

In some embodiments, methods for determining a DNA methylation profile in a subject over time include aggregating the number of methylated molecules across the at least ten target loci (or a subset thereof, e.g., at least two target loci); and normalizing the aggregate number of methylated molecules from all or a subset of the at least 10 target loci by the methylated molecules for the at least one normalization locus. In some embodiments, the aggregating and normalizing results in quantification of DNA methylation (e.g., a Tumor Methylation Score) that represents the normalized sum of methylated molecules (e.g., at the at least ten target loci that are hypermethylated in the sample at a given time point). Comparing across time points enables determination of a DNA methylation profile in a subject (over time).

In some cases, the DNA methylation profile identifies a change in the methylation profile from the first time point to the second time points, second to the third time points, or the first to the third time points.

In some embodiments, a method for determining a DNA methylation profile in a subject over time includes assigning a change in methylation profile a metric of: an increase, a decrease, or a no-change based on comparison to a significance threshold. The significance threshold can be predetermined or dynamically calculated. For example, without limitation, a method for determining a DNA methylation profile in a subject over time indicates a change where the change is an increase because the DNA methylation profile (e.g., the Tumor Methylation Score™) exceed a predetermined significance threshold of about 15% compared to a previous timepoint. For example, without limitation, a method for determining a DNA methylation profile in a subject over time indicates a change where the change is a decrease because the DNA methylation profile (e.g., the Tumor Methylation Score™) exceed a predetermined significance threshold of about 15% compared to a previous timepoint. In some embodiments, the predetermined significance threshold to be exceeded for a change in a DNA methylation profile (e.g., the Tumor Methylation Score) to be considered an increase or a decrease is 20%, 19%, 18%, 17%, 16%, 15%, 14%, 13%, 12%, 11%, 10%, 9%, 8%, 7%, 6%, 5%, 4%, 3%, 2% or 1% compared to a previous timepoint.

In some embodiments, the change in methylation pattern indicates a change in a tumor in the subject. The change in the tumor comprises a change in the size of the tumor, a change in abundance of a somatic mutation associated with the tumor, a presence of a new somatic mutation associated with the tumor, a chromosomal abnormality associated with the tumor, or that the tumor is resistant to a therapy. In some embodiments, an increase in a DNA methylation profile (e.g., Tumor Methylation Score™) of at least 1.5-fold (e.g., 2-fold, 3-fold, 4-fold, or 5-fold) compared to a DNA methylation profile at a previous timepoint indicates a change in the tumor. In some embodiments, an increase in a DNA methylation profile (e.g., Tumor Methylation Score™) of at least 2-fold compared to a DNA methylation profile at a previous timepoint indicates a change in the tumor. In some embodiments, where DNA methylation in a sample includes at least 10% (e.g., at least 15%, at least 20%, at least 30%, at least 40%, at least 50%, at least 60%, at least 70%, at least 80%, or at least 90%) of the DNA methylation as originating from newly methylated target loci (e.g., a target loci not previously found to be methylated at a previous time point), the DNA methylation profile identifies a change in the tumor (e.g., the tumor associated with the sample). In some embodiments, where DNA methylation in a sample includes at least 40% of the DNA methylation in the sample (e.g., methylation at the target loci in cfDNA) of the DNA methylation as originating from newly methylated target loci (e.g., a target loci not previously found to be methylated at a previous time point), the DNA methylation profile identifies a change in the tumor (e.g., the tumor associated with the sample). In some embodiments, an increase in a DNA methylation profile (e.g., Tumor Methylation Score™) of at least 2-fold compared to a DNA methylation profile at a previous timepoint and where at least 40% of the DNA methylation in the sample (e.g., 40% of Tumor Methylation Score™) is from newly methylated target loci (e.g., a target loci not previously found to be methylated at a previous time point) indicate a change in the tumor (e.g., the tumor associated with the sample).

In one embodiment, a DNA methylation profile determined using the methods described herein can be incorporated into a clinical recommendation. A clinical recommendation can include a plan for further testing or treatment: For example, based on the quantified DNA methylation in the sample and the clinical implications of the DNA methylation, a plan for further testing or treatment can be developed. In some cases, this may involve additional testing to confirm the diagnosis, monitoring for disease progression or recurrence, or prescribing targeted therapies that are specific to the subject's DNA methylation profile.

6.10. Quantifying the Abundance of a Somatic Mutation in a Sample

This disclosure also features methods for determining an indication of confidence in the presence or absence of a somatic mutation in a sample where an indication of confidence in the presence or absence of a somatic mutation in the sample is assigned a "true call" or a "no-call" based, in part on, quantification of DNA methylation in the same sample from which the somatic mutation was determined to be present or absent. In one example, concordance between presence or absence of a somatic mutation and DNA methylation shows that methylation (i.e., methylation analyzed and identified according to the methods described herein) can be used to inform the confidence levels of whether a somatic mutation is present or absent, which in turn, can be used for a clinical recommendation for the subject.

In one embodiment, a method for determining an indication of confidence in the presence or absence of a somatic mutation in a sample containing DNA sequences, includes the following one or more steps. In some embodiments, the method includes a step of determining a presence or absence of a somatic mutation in the sample. In other embodiments, the method does not include a step of determining a presence or absence of a somatic mutation in the sample because the treating step had been done prior to use of the methods provided herein. In such cases, the method includes quantifying DNA methylation in the sample that was used to determine the presence or absence of the somatic mutation, but with the determination of the presence or absence of the somatic mutation performed prior to using the methods described herein.

In some embodiments, the method for determining an indication of confidence in the presence or absence of a somatic mutation in a sample containing DNA sequences includes: quantifying DNA methylation in the sample comprising the steps of as described herein (see, e.g., Section 6.7). In some cases, the method includes optionally treating the sample to encode the presence or absence of DNA methylation in the DNA sequences, wherein the sample comprises at least ten target loci from the DNA sequences, where each locus of the at least ten target loci is chosen based on an expected increase in DNA methylation at each loci in cancerous tissue compared to non-cancerous tissue and the sample optionally includes normalization loci (e.g., loci that are highly methylated in both cancerous tissues and normal (e.g., non-cancerous) tissue). In some embodiments, the sample is treated to encode the presence or absence of DNA methylation in the DNA sequences prior to performing the methods described herein. In some embodiments, the method includes adding to the sample a set of synthetic molecules, the set of molecules comprising: target-associated regions having a nucleotide sequence that matches a corresponding nucleotide sequence to an endogenous target, and variation regions with a nucleotide sequence that does not match a sequence region of an endogenous target molecule. The method also includes generating a co-amplification mixture comprising an amplified set of synthetic molecules and an amplified set of at least ten target loci from the DNA sequences; and sequencing the co-amplified mixture (e.g., at a read depth of at least one read sequence per molecule in the sample to generate sequence reads). The method further includes determining a number of the sequence reads that are methylated sequence reads; quantifying a number of methylated molecules in the sample based on the number of methylated reads from the sample and a number of reads from the set of synthetic molecules.

Following determination of the presence or absence of the somatic mutation and the quantity of the DNA methylation in the sample, the method returns an indication of confidence (i.e., confidence in the determination of the presence or absence of the somatic mutation) as: a true call result for the presence or absence of the somatic mutation when the number of methylated molecules in the sample is above a predetermined or dynamically calculated threshold; or a no-call result for the presence or absence of the somatic mutation when the number of methylated molecules in the sample is at or below a predetermined or dynamically calculated threshold, whereby a true call identifies confidence in the determination of the presence or absence of the somatic mutation.

In one embodiment, methods for determining an indication of confidence in the presence or absence of a somatic mutation in a sample include quantifying the number of methylated molecules in both cfDNA (plasma) and gDNA (buffy coat) using QCT molecular counting technology (e.g., as described in U.S. Pat. Pub. 2019/0211395A1, which is incorporated by reference) at the at least ten target loci, where each locus of the at least ten target loci is chosen due to an expected increase in DNA methylation at each loci in cancerous tissues compared to normal (e.g., non-cancerous) tissue. In such embodiments, the number of methylated molecules for cfDNA is quantified as described herein (see Section 6.7) and the number of methylated molecules for gDNA are each quantified as described herein (see Section 6.7). The quantification of the number of methylated molecules provides a mechanism by which to assign the determination of the presence or absence of a somatic mutation a true call (e.g., a correct call) or a no-call (e.g., insufficient DNA to assign sufficient confidence to the abundance measurement). For example, quantifying DNA methylation in the same sample that was used to determine the presence or absence of the somatic mutations returns an indication of confidence for the somatic mutation determination. A true call result for the presence or absence of the somatic mutation is returned when the number of methylated molecules in the sample is above a predetermined or dynamically calculated threshold. A no-call result for the presence or absence of the somatic mutation is returned when the number of methylated molecules in the sample is at or below the predetermined or dynamically calculated threshold. A no call indicates that the determination of the presence or abundance of the somatic mutation cannot be assigned sufficient confidence to say the measurement is correct.

In some embodiments, methods for determining an indication of confidence in the presence or absence of a somatic mutation in a sample include addition of a spike-in of known sequence and quantity to the sample prior to the treating step. The spike-in comprises a known sequence having unmethylated cytosines that are converted to uracils upon being subjected to the treating step. As noted above, this enables calculation of the bisulfite conversion yield and conversion efficiency, thereby establishing bisulfite conversion QC metrics that can be used to determine if a sample failed the bisulfite conversion step.

In some embodiments, methods for determining an indication of confidence in the presence or absence of a somatic mutation in a sample include a step of processing the methylated sequence reads by one or more of the following: filtering out selected hypermethylated target loci (e.g., filtering out target loci having a total number of methylated molecules in the buffy coat above a threshold); or subtracting background methylation (e.g., subtracting the number of methylated molecules as measured in the buffy coat from the number of methylated molecules in the cfDNA, which can be done a per-locus basis). In some embodiments, processing is performed prior to the step of quantifying the number (e.g., the absolute number) of methylated molecules in the sample. In such cases, filtering hypermethylated loci, subtracting background methylation, or both, are performed prior to quantifying the absolute number of methylated molecules in the sample.

In some embodiments, upon returning a true call and where the presence of the somatic mutation indicates the presence of cancer, the method includes performing or repeating a treatment selection assay (e.g., treatment selection assay comprises genomic profiling to detect novel somatic mutations, the abundance of somatic mutations, or both) on the subject. In some embodiments, upon returning of a no-call, the method is repeated, at least in part, on a different sample taken from the same subject.

In some embodiments, the method for determining an indication of confidence in the presence or absence of a somatic mutation in a sample include a step of further comprising aggregating the number of methylated molecules across at least two of the at least ten target loci to quantify the DNA methylation in the sample. Aggregation can include aggregating target loci that contain lower than a threshold amount of methylated molecules in the buffy coat.

In some embodiments, the method for determining an indication of confidence in the presence or absence of a somatic mutation in a sample includes aggregating the number of methylated molecules across the at least ten target loci (or a subset thereof, e.g., at least two target loci); and normalizing the aggregate number of methylated molecules from all or a subset of the at least 10 target loci by the methylated molecules for the at least one normalization locus.

6.11. Kit

In another aspect, this disclosure features a kit for quantifying DNA methylation in a sample using the methods described herein. In some embodiments, a kit for quantifying DNA methylation in a sample using the methods described herein. In some embodiments, a kit can include one or more of the following: conversion reagents required to encode the presence or absence of DNA methylation in the DNA sequences, synthetic molecules (e.g., QCT molecules) to be added to the sample at various points in sample processing, reagents required for the amplification of the DNA sample, and reagents required for preparing a sequencing library such as those needed for indexing PCR.

7. EXAMPLES

7.1. Materials and Methods for Examples 1-10

7.1.1. Tumor Hypermethylation Target Selection

The Cancer Genome Atlas's (TCGA) was queried for subjects with human methylation data for both tumor and normal tissue of the same tissue type. Data from TCGA was collected using the Infinium HumanMethylation450 BeadChip (Illumina, San Diego, CA) and provided beta values representing the methylation fraction at specific CpG locations in the genome. In addition, methylation data for white blood cells collected from patients of age similar to cancer patients (mean=63.9 years, sd=13.3 years) was obtained from GEO accession GSE40279 (see Hannum, G. et al., (2013). *Molecular Cell,* 49(2), 359-367. doi.org/10.1016/j.molce1.2012.10.016).

Tumor hypermethylation was calculated at each CpG site by subtracting normal tissue beta from tumor beta. To avoid choosing CpG sites with spurious hypermethylation, an average hypermethylation was calculated for each CpG island, and CpG islands were ranked in order of highest hypermethylation. Additionally, CpG islands were filtered for average white blood cell beta<0.2 to minimize background signal from buffy coat contributions to the cfDNA. From each selected CpG island, several CpG locations were chosen for primer design.

A lung cancer specific assay was designed using TCGA data from subjects with lung adenocarcinoma and lung squamous cell carcinoma. A pan-cancer assay was also designed using TCGA data from many cancer types (e.g., lung adenocarcinoma, lung squamous cell carcinoma, colon adenocarcinoma, breast invasive carcinoma, pancreatic adenocarcinoma, liver hepatocellular carcinoma, bladder urothelial carcinoma, esophageal carcinoma, kidney renal cell carcinoma, kidney renal papillary cell carcinoma, prostate adenocarcinoma, thyroid carcinoma, and uterine corpus endometrial carcinoma).

7.1.2. Highly Methylated Target Selection

In addition to selecting targets with hypermethylation in tumors compared to normal tissue, control loci that are highly methylated in both buffy coat, tumor, and normal tissue were selected as well. Methylation data was obtained and analyzed similarly as for the hypermethylated targets, but ranked in order of highest white blood cell methylation signal and filtered for beta>0.9 for white blood cell, tumor tissue, and normal tissue for six cancer types (lung adenocarcinoma, lung squamous cell carcinoma, colon adenocarcinoma, breast invasive carcinoma, pancreatic adenocarcinoma, liver hepatocellular carcinoma).

7.1.3. Primer and QCT Design

Primer3 was used to design primer pairs targeting the genomic locations of chosen CpG locations and using a reference genome that was bisulfite converted in silico. This process was performed assuming full methylation of the reference hg19 human genome, converting all Cs to Ts except for CpGs. The ideal annealing temperature was set to 60° C.

Single stranded QCTs were designed for each amplicon. The predicted amplicon sequence for each primer pair was determined using Bowtie and the converted human genome, and 17 bases of flanking genomic sequence were added to both 5' and 3' ends. Eleven bases in the insert region of the QCT were replaced with Ns, allowing for a small number of unique QCTs to be added to each PCR reaction.

7.1.4. Additional Amplicons

In addition to tumor hypermethylated and highly methylated genomic targets, additional amplicons were included in the assay. Fifteen genotyping amplicons were designed targeting A>G or G>A SNPs that are commonly found according to NCBI's Single Nucleotide Polymorphism Database (dbSNP). The genotype at these locations can be used to check for sample swaps that may occur during lab processing or at the clinic. Three amplicons targeting genomic locations on chromosome Y were included to determine the sex of the patient.

Two artificial amplicons were included to check for bisulfite conversion yield and conversion efficiency. These synthetic oligos are spiked-in to the cfDNA and gDNA sample just prior to bisulfite conversion at a fixed quantity. These oligos are then amplified in the multiplex reaction along with all the other amplicons. During analysis, the initial number of spike-in molecules can be calculated as well as the percent of cytosine bases that were converted to thymine bases (the oligos were synthesized without any methylation). For the multiplex PCR no-template control, the same amount of bisulfite conversion spike-ins are added after bisulfite conversion, allowing for an estimate of the overall bisulfite conversion yield. Calculating the bisulfite conversion yield and conversion efficiency allows for the establishment of bisulfite conversion QC metrics and therefore determination of whether a sample failed the bisulfite conversion step of the process.

7.1.5. Specimen Sourcing

To obtain a number of tumor specimens spanning a variety of cancer types, banked flash frozen tumors and buffy coats from the same subjects were obtained from Spectrum Health (Grand Rapids, MI).

To test whether the assay could detect changes in methylation that were concordant with clinical outcomes, samples were collected from cancer patients both retrospectively and prospectively. Retrospective samples consisting of banked plasma and buffy coat samples were obtained through collaborations with the University of California at San Diego and the University of Florida. Prospective sample collection was performed through contract research organizations and their partner clinics; patients that were diagnosed with cancer and had not started treatment were enrolled. Blood was collected in Streck tubes pre-treatment and at subsequent time points post-treatment. Clinical outcomes were provided when available.

To test how the assay performs on healthy individuals, blood was collected from healthy volunteers at various time points.

7.1.6. Specimen Preparation

Blood collected in EDTA tubes were spun down within one hour of collection and plasma and buffy coat were isolated. Blood collected in Streck tubes were allowed to sit overnight before spinning down and isolating plasma and buffy coat. Plasma volume was recorded for normalization in analysis.

cfDNA was extracted using the QIAamp Circulating Nucleic Acid Kit (Qiagen), and gDNA was extracted from tumor samples and buffy coat samples using the DNeasy Blood & Tissue Kit (Qiagen).

Contrived samples mimicking cell-free DNA (cfDNA) samples from cancer patients were created by mixing tumor genomic DNA (gDNA) into buffy coat gDNA at various tumor fractions.

7.1.7. Bisulfite Conversion and Library Prep for Next Generation Sequencing

Samples were either bisulfite converted using the Diagenode Premium Bisulfite kit (Cat No. CO2030030) or the Zymo EZ-96 DNA Methylation-Lightning MagPrep kit (Cat No. D5046). When either cfDNA or gDNA sample volumes were larger than the recommended input volume, samples were split in half, converted separately, and then re-combined. Enzymatic conversion was also tested. As a positive control for detecting methylation, universally methylated genomic DNA (Cat. No. S7821, Sigma-Aldrich) was diluted in buffy coat at various tumor fractions.

Primer mixes were created by pooling all primer pairs and iteratively removing and/or rebalancing the concentrations of each primer pair to optimize for balanced coverage across target amplicons. QCTs were diluted to 200 molecules per PCR reaction at each amplicon. A total of 113 target amplicons were included for the lung cancer assay, and 679 target amplicons were included for the pan-cancer assay.

Multiplex PCR was performed on bisulfite converted specimens using Q5U polymerase (NEB, Ipswich, MA). Subsequently, indexing PCR was performed using Q5 polymerase (NEB, Ipswich, MA) in order to sequence multiple samples on the same sequencing run with dual indexes. Pooled libraries were bead cleaned and loaded on NextSeq 2000 (Illumina, San Diego, CA) sequencing instruments using P3 100 cycle reagents for single-directional sequencing and 5% PhiX.

7.1.8. Calculating the Number of Methylated Molecules

Fastq files were adapter trimmed on the 3' end using BBDuk and then mapped using BWA-MEM to a custom genome composed of the target hypermethylated and highly methylated amplicon, and QCT sequences.

For each amplicon, reads that mapped to the target amplicon (e.g., the target hypermethylated amplicon or the highly methylated amplicon) were binned based on sequence. The number of CpGs contained in each sequence was calculated, and each sequence was classified as belonging to a methylated read if the number of CpGs was greater than or equal to the maximum number of possible CpGs for that amplicon minus one. Reads mapping to the corresponding QCT sequence were separately processed and binned based on the random N sequence of the QCT. Assuming each QCT molecule's sequence is unique in each reaction, an average number of reads per QCT molecule was calculated. The total number of methylated molecules for that amplicon can then be calculated by dividing the total number of methylated reads by the average reads per QCT molecule.

When measurements were obtained for paired cfDNA and buffy coat samples, background levels of methylation were reduced by subtracting the buffy coat methylation signal from the cfDNA methylation signal on a per-locus basis. It is estimated that about 55% of the cfDNA is of white blood cell origin based on methylation patterns (see Moss, J. et al., (2018), *Nature Communications,* 9(1), doi.org/10.1038/s41467-018-07466-6), suggesting that subtracting the entirety of the buffy coat methylation is a conservative approach to remove background methylation signal. Any calculated negative numbers of molecules after background subtraction were capped at zero.

In order to perform a comparable subtraction between buffy coat and cfDNA samples, the samples must first be normalized to the input amount of genomic equivalents. The average of the highly methylated loci methylated molecules is used to estimate the total number of genomic equivalents in the sample overall. The number of methylated molecules at each locus is normalized by the estimated genomic equivalents of that sample. The number of normalized methylated molecules is then used for background subtraction.

7.1.9. Hypermethylation Locus Filtering

Based on testing healthy subjects, certain hypermethylation loci were found to have significant methylation signal even after buffy coat subtraction. To minimize the amount of false cancer signal, certain loci were filtered out from analysis. In some cases, this is referred to herein as "blacklisting." Any loci found to either consistently contribute a moderate amount of methylation or occasionally contribute a high amount of methylation in healthy subjects were added to a list of loci to ignore. These loci often contain high amounts of methylation in buffy coat.

After filtering hypermethylation loci, the results from healthy subjects was used to establish a noise floor, below which the methylation signal is not interpretable because it is comparable to the amount seen in healthy subjects.

7.1.10. Calling Changes in Methylation

When two time points of data were available, a call was made as to whether there has been an increase, decrease, or no change in the amount of methylated molecules. The call was made by modeling each time point's measurement as a normal distribution with a mean of the number of measured methylated molecules (normalized to the total number of input molecules). A standard deviation is assigned to the normal distribution based on the total number of methylated molecules; this can be done by interpolating based on previous studies where the coefficient of variation was measured from contrived samples (see, e.g., Example 7, Arm 3). The normal distribution from the first time point is subtracted from the second time point and normalized to the mean of the first time point's normal distribution, creating a normalized difference normal distribution. An "Increase" call was made if the mean of this distribution is ≥15% and the log 2 likelihood ratio that the difference was ≥15% compared to <15% was greater than 3. Similarly, a "Decrease" call was made if the mean of this distribution is ≤−15% and the log 2 likelihood ratio that the difference was ≤−15% compared to >−15% is greater than 3. If the relative difference was not of sufficiently large magnitude or the statistical likelihood was not sufficiently strong, a "No Change" call was made. If either time point was below the noise floor, the mean for that time point was set to the noise floor, the standard deviation was still calculated based on the total number of methylated molecules, and a call was still made. If the methylation signal from both time points was below the noise floor, an "Indeterminate" call was made. Any other suitable statistical methods, including but not limited to mean, median, standard deviation, likelihood ratio, expectation maximization, statistical significance tests can be used to make the calls.

7.1.11. Methylation Profile

To capitalize on the fact that the assay measures methylation at hundreds of hypermethylation locations, a methylation profile was determined at each time point. One way to build the methylation profile was to categorize loci based on which time point a locus was first found to have informative methylation signal. This was defined as greater than 2 molecules after background subtraction. Categorizing the loci by first informative time point revealed when and how much the methylation profile changed.

7.2. Example 1. Lung Cancer Assay can Detect Significant Methylation in 0.5% Tumor Fraction Contrived Samples The lung cancer assay was assessed for its limit of detection using contrived samples. Without wishing to be bound by theory, contrived specimens are prepared to mimic clinical specimens as closely as possible. For these experiments, the contrived samples included sheared tumor gDNA, which were sheared using a sonicator to an average fragment length of ~170 bp to mimic the size distribution of cfDNA. Contrived samples made with universal methylation were used as a positive control (e.g., in place of tumor DNA as a positive control). Positive controls were sheared in the same manner as the contrived lung cancer samples. A total of 1.35E9 sequencing reads were obtained, resulting in an average of 11E6 average reads per sample. There were an average of 62 reads per QCT across all samples and amplicons. Each contrived sample was created with 5000 genomic equivalents (g.e.).

Technical replicates of lung cancer contrived samples were tested at 0%, 0.5%, 1%, 2.5%, and 5% tumor fractions (See FIG. 2A). The assay was able to distinguish 0.5% tumor fraction samples from 0% tumor fractions, suggesting that the limit of detection was at least 0.5%.

The lung cancer assay was also used to measure methylation in additional lung tumor specimens (see FIG. 2B). FIG. 2B shows the lung cancer assay was used to detect methylation in contrived samples from two additional lung cancer subjects. For these experiments different PCR volumes and different thermal cycling protocols were used (see FIG. 2B).

Additional analysis using the lung cancer assay included measuring concordance values (CV) (FIG. 3) of the samples analyzed in FIG. 1A. CVs were used to determine whether ctDNA, and correspondingly the amount of tumor, truly increased or decreased or whether the increase or decrease was false positive or a false negatives. Without any additional post-processing, the CV of the methylation measurements was around 10% or less. This suggested that the methylation measurements generated using the methods described herein confidently identified a 30% change in signal within 3 standard deviations. According to RECIST guidelines, a partial response was defined by at least a 30% decrease in the longest diameter of the target tumor lesion, and progressive disease was defined by at least a 20% increase in the longest diameter of the target tumor lesion. In view of these RECIST guidelines, the assays described herein enable assessment of tumor response to therapy in the context of current standard of care. In fact, quantification of treatment response following RECIST guidelines is limited by the selection of a limited number of identifiable tumors on imaging, whereas the methylation assay provides a measurement of all tumors present in the body that shed DNA into the bloodstream.

7.3. Example 2. Background Subtraction Improves Signal-to-Background Ratio

Optimizations were performed to improve the signal-to-background ratio. Without wishing to be bound by theory, improving the signal-to-background ratio is particularly helpful for detecting smaller tumor signals. For example, one medical application is for minimal residual disease (MRD) detection, where the difference between having any tumor signal and zero signal could be the difference between recurrence and remission.

Despite filtering for targets with low methylation in buffy coat and normal tissue in the target selection process, some targets may still have significant amounts of background methylation. One approach to reduce the impact of background methylation was to mask the signal from target loci with buffy coat methylation above a certain threshold. Another parallel approach was to subtract the methylation signal as measured in the buffy coat from the methylation signal measured in the cfDNA (in the plasma) on a per-locus basis.

FIG. 4 shows total normalized methylated molecules for technical replicates of lung cancer contrived samples at various tumor fractions. In particular, FIG. 4 shows data from a lung cancer assay that included background subtraction (i.e., subtracting the methylation signal as measured in the buffy coat from the methylation signal measured in the cfDNA) and masking of target loci with high background methylation (i.e., mask the signal from target loci with buffy coat methylation above a certain threshold). For example, the background methylation signal was calculated by using the buffy coat methylation signal per locus, normalized to the average highly methylated loci methylated molecules (e.g., average of normalization loci) in each buffy coat sample, and averaging across all buffy coat samples. 55% of the background signal was subtracted from each cfDNA contrived sample's methylation signal, normalized to the average highly methylated loci methylated molecules in each contrived sample. Hypermethylation target loci with greater than 10 methylated molecules per 1000 highly methylated loci methylated molecules were masked. Any other suitable threshold can be determined.

By masking loci and subtracting the buffy coat methylation signal from the contrived cfDNA signal, background signal was reduced in the 0% tumor fraction contrived samples from an average of 277 methylated molecules to 111 methylated molecules. More stringent masking of hypermethylation target loci was expected to further reduce the background signal.

Overall, this data showed signal-to-background ratio could be improved using background subtraction (i.e., subtract the methylation signal as measured in the buffy coat from the methylation signal measured in the cfDNA) in parallel with masking of target loci with high background methylation (i.e., mask the signal from target loci with buffy coat methylation above a certain threshold).

7.4. Example 3. Hypermethylation-Based Measurements are Robust to gDNA Contamination, Unlike Somatic Mutation-Based Approaches A common problem with cfDNA assays is gDNA contamination. This can occur during the plasma isolation of centrifuged whole blood when buffy coat is accidentally isolated along with the plasma fraction. gDNA contamination can have a detrimental effect on the accuracy of cfDNA tumor quantification especially when using somatic mutation variant allele fractions for cfDNA tumor quantification. This is because the additional buffy coat contributes to the denominator. As shown in FIG. 5 (top panel), 1×gDNA contamination (e.g., contamination that amounts to a doubling of the total number of molecules) reduced the variant allele fraction by half. This could result in a false positive signal. When a positive signal correlates with treatment efficacy, such a result has the potential to alter medical decision making.

This experiment showed that detection of tumor hypermethylation was less vulnerable to gDNA contamination than a somatic mutation ctDNA assay. This is at least because targets were selected for low buffy coat methylation and background subtraction methods were used. If the background methylation signal was zero in the buffy coat, the absolute number of methylated molecules was not affected at all by gDNA contamination (FIG. 5; middle panel). Even if buffy coat did contribute a small amount of methylation background signal (FIG. 5; bottom panel), measuring the buffy coat methylation and subtracting that signal from the cfDNA signal kept the total methylation signal within an increase of 20% for a 1× amount of gDNA contamination. This minimized the effect of gDNA contamination on the tumor methylation measurement and any potential downstream medical decisions to be made based on the tumor methylation measurement.

In addition to target selection and background subtraction, additional biochemical methods to minimize gDNA contamination existed, including bead purification to size select the DNA fragments in a cfDNA sample. However, as these methods can also fail, it is helpful to have orthogonal approaches for robustness against gDNA contamination.

7.5. Example 4. Day-to-Day Variability in Buffy Coat Methylation in Healthy Subjects was Comparable to Subject-to-Subject Variability The degree of day-to-day variability of methylation in healthy subjects was assessed as part of the assay's ability to make accurate, time serial measurements. Because a significant portion of the cfDNA signal is of buffy coat origin, the methylation profile of buffy coats was measured from healthy subjects across different tubes of the same blood draw, different tube types, different days, and different subjects. The data in FIG. 6 shows methylation profiles for buffy coats (i.e., 5000 g.e. of buffy coat) isolated from different tubes of the same blood draw, different tube types, different days, and different subjects (see Table 1 for sample identifiers in FIG. 6).

TABLE 1

| Sample identifiers | Column in FIG. 6 (left to right) |
|---|---|
| BARHL2_cg11823511_3 | 1 |
| BNC1_MSP_W_0 | 2 |
| C2orf40_cg17161250_0 | 3 |
| C3orf72_cg184`4754_96 | 4 |
| CCDC140_cg12973118_0 | 5 |
| CNPY1_cg01198033_73 | 6 |
| CNPY1_cg07416383_4 | 7 |
| CTNNA2_cg20072442_66 | 8 |
| CTNNA2_cg24632241_54 | 9 |
| CYP11A1_cg16332610_29 | 10 |
| DIDO1_cg15680020_66 | 11 |
| DNM3_cg02011074_79 | 12 |
| DNM3_cg23391785_0 | 13 |
| FAIM2_cg18486102_2 | 14 |
| FAM59B_cg00399175_2 | 15 |
| FLJ32063_cg00768993_63 | 16 |
| FLJ32063_cg08690859_17 | 17 |
| FLJ32063_cg19376851_3 | 18 |
| GABRA4_cg24154839_2 | 19 |
| GRIA4_cg04747226_MSP_W_8 | 20 |
| HOXA9_cg15506609_0 | 21 |

TABLE 1-continued

| Sample identifiers | Column in FIG. 6 (left to right) |
|---|---|
| HOXB4_cg07438617_0 | 22 |
| HOXD8_cg14473102_31 | 23 |
| HOXD8_cg24416513_0 | 24 |
| INA_cg18932798_0 | 25 |
| intron_cg00158528_24 | 26 |
| intron_cg01447112_0 | 27 |
| intron_cg02340083_36 | 28 |
| intron_cg03075534_3 | 29 |
| intron_cg03204678_4 | 30 |
| intron_cg03257575_2 | 31 |
| intron_cg04067139_29 | 32 |
| intron_cg04502985_0 | 33 |
| intron_cg051838931_52 | 34 |
| intron_cg06643013_0 | 35 |
| intron_cg07149609_21 | 36 |
| intron_cg07891531_0 | 37 |
| intron_cg08189989_0 | 38 |
| intron_cg08235161_10 | 39 |
| intron_cg08368617_77 | 40 |
| intron_cg091929100_3 | 41 |
| intron_cg10034364_0 | 42 |
| intron_cg10422777_0 | 43 |
| intron_cg11071231_35 | 44 |
| intron_cg11665991_32 | 45 |
| intron_cg12505170_12 | 46 |
| intron_cg12853633_0 | 47 |
| intron_cg13239420_0 | 48 |
| intron_cg13368519_50 | 49 |
| intron_cg13713830_0 | 50 |
| intron_cg14189141_0 | 51 |
| intron_cg15415452_29 | 52 |
| intron_cg17869514_5 | 53 |
| intron_cg18144593_0 | 54 |
| intron_cg18969232_75 | 55 |
| intron_cg19025113_83 | 56 |
| intron_cg19375537_16 | 57 |
| intron_cg19516105_0 | 58 |
| intron_cg19737787_0 | 59 |
| intron_cg20785796_0 | 60 |
| intron_cg21235151_0 | 61 |
| intron_cg21821214_0 | 62 |
| intron_cg22524657_0 | 63 |
| intron_cg22876812_0 | 64 |
| intron_cg23089825_1 | 65 |
| intron_cg23348270_4 | 66 |
| intron_cg23713079_16 | 67 |
| intron_cg25168494_20 | 68 |
| intron_cg25570913_MSP_W_0 | 69 |
| intron_cg25738714_43 | 70 |
| intron_cg25739043_10 | 71 |
| intron_cg25950325_84 | 72 |
| intron_cg26379859_2 | 73 |
| intron_cg27315333_0 | 74 |
| intron_cg27529871_3 | 75 |
| intron_cg27555582_0 | 76 |
| ITGA8_cg16422098_99 | 77 |
| ITGA8_cg26104297_1 | 78 |
| L1TD1_cg03731268_79 | 79 |
| LHX1_cg14754787_18 | 80 |
| NPTX2_MSP_W_9 | 81 |
| PAX3_cg09424526_0 | 82 |
| PAX3_cg14265823_29 | 83 |
| PAX9_cg01672943_0 | 84 |
| PAX9_cg01972418_8 | 85 |
| PITX2_MSP_W_37 | 86 |
| PPFIA3_cg13484549_6 | 87 |
| PRDM14_cg11229513_5 | 88 |
| PROM1_cg12839172_14 | 89 |
| PTGDR_cg18693395_0 | 90 |
| PTGDR_cg24989962_0 | 91 |
| RALYL_cg25757598_0 | 92 |
| RNF220_cg18180569_7 | 93 |
| RYR2_cg07790615_4 | 94 |
| SFRP1_MSP_W_93 | 95 |
| SOX2OT_cg14317285_0 | 96 |
| SOX2OT_cg17202313_55 | 97 |

TABLE 1-continued

| Sample identifiers | Column in FIG. 6 (left to right) |
|---|---|
| TAC1_MSP_W_39 | 98 |
| TFPI2_MSP_W_92 | 99 |
| TMEM132C_cg00579520_16 | 100 |
| TMEM132C_cg03530754_97 | 101 |
| USP44_cg13879483_MSP_W_3 | 102 |
| USP44_cg22538054_MSP_W_3 | 103 |
| VAX1_cg17138769_45 | 104 |
| VWC2_cg01893212_MSP_W_29 | 105 |
| WT1_cg19126300_30 | 106 |
| ZNF781_cg25324105_0 | 107 |
| ZNRF3_cg13298692_18 | 108 |

For example, the two tubes from Subject 5 from the same day with the same tube type were very similar, which was expected (see FIG. 6). Tube type did not cause significant differences as the EDTA tube was very similar to both Streck tubes. The data from the Streck tube collected on Day 2 was similar to data from the Streck tube collected on Day 1, but with a few loci with notable differences. There were noticeable subject-to-subject differences, as Subject 10 had several methylated loci that were not methylated in any of the tubes from Subject 5.

FIG. 7 shows hierarchical clustering of methylation profiles from buffy coats isolated from different tubes of the same blood draw, different tube types, different days, and different subjects. Clustering was performed based on methylated molecules at each target hypermethylation locus, normalized to the amount of methylated molecules measured at highly methylated loci. Cluster distance was calculated using the L1 norm.

Hierarchical clustering revealed that the tubes collected on the same day, no matter the tube type, clustered together the closest (see FIG. 7). Examples of tubes on the same day clustering together included Subject 1 Day 1, Subject 3 Day 1, Subject 3 Day 2, and Subject 10 Day 1. However, tubes collected from the same subject but on different days cluster as far apart as tubes collected from different subjects. This suggested that background subtraction was more optimal if performed using methylation profiles from buffy coat collected at each unique time point.

7.6. Example 5. Pan-Cancer Assay Detects Methylation Signal in Multiple Cancer Types A pan-cancer assay was designed based on the methods described herein.

FIG. 8 shows data from the methylation signal in the pan-cancer assay in contrived samples of several different cancer types. For these experiments, 5% tumor fraction contrived samples were made by mixing 5% of tumor gDNA with 95% of buffy coat from the same subject by mass. 0% tumor fraction contrived samples were pure buffy coat. Specimens were labelled with their cancer type (BRCA: breast invasive carcinoma, COAD: colon adenocarcinoma, LIHC: liver hepatocellular carcinoma, LUNG: lung cancer, PAAD: pancreatic adenocarcinoma). Universal methylated samples were included as positive control for the methylation assay.

As shown in FIG. 8, the pan-cancer assay was able to detect methylation signals in 5% tumor fraction contrived samples of several cancer types using the same chemistry for all samples. There was noticeable variability in methylation signal across specimens, which could have been due to a couple causes. First, the methylation profile of the tumor likely differed from tumor to tumor. This profile may or may not have coincided with the target locations included in the assay. In the assays described herein, increasing the number of target locations can help minimize the effect of biological variability in methylation across tumors. The variability could have also been due to a technical limitation with contrived samples made with tumor specimens, as the tumors themselves contained an unknown proportion of normal tissue. Therefore, comparing measurements made on contrived samples of the same tumor fraction across specimens should be done cautiously. Despite the exact tumor quality being unknown, the assay was still able to differentiate the 5% tumor fraction contrived tumor samples from a pure buffy coat sample from the same subject.

Overall, this data established that the methods described herein include the ability for pan-cancer detection.

7.7. Conclusion from Examples 1-5

This data demonstrated an innovative approach to cancer treatment monitoring by quantifying the absolute number of methylated molecules. Existing ctDNA assays have poor precision for treatment monitoring due to a very limited number of detectable variants and therefore a very small total number of variant molecules. Whole exome sequencing of a tumor biopsy could be performed to identify additional variants and overcome molecule sampling limitations, but that requires a tumor biopsy which may be difficult to obtain at all from the patient or may not have sufficient material remaining from the clinic. By resolving several technical shortcomings of existing treatment monitoring approaches, we believe that this methylation-based, tumor-naïve, multiplexed, quantitative assay will be of great use to oncologists and their patients for guiding treatment decision making.

7.8. Example 6. Filtering Hypermethylated Loci

The lung-cancer assay described in Example 2 improved the signal-to-background ratio using background subtraction, which included subtracting the methylation signal as measured in the buffy coat from the methylation signal measured in the cfDNA, in parallel with masking of target loci with high background methylation (i.e., mask the signal from target loci with buffy coat methylation above a certain threshold). However, masking of target loci with high background methylation proved to be an effective but blunt tool that warranted additional optimization. Described below are attempts to further improve the signal-to-background ratio using masking of target loci.

Attempts to improve signal-to-background ratio using masking of target loci included an analysis of 16 samples from 10 separate healthy subjects with the aim of identifying loci that when masked (filtered out) would reduce the signal-to-background ratio.

The pan-cancer assay(s) described herein measured methylation at loci that are often hypermethylated in cancer. One limitation of the assay(s) was that not all methylation signal was cancer signal. This could have been due to loci that have non-zero amounts of background methylation (e.g., methylation in non-cancer subjects).

As noted above, limiting the amount of background methylation has an impact on accurate treatment monitoring. Without wishing to be bound by theory, methylation that is randomly presented can introduce spurious signal that may lead to incorrect clinical interpretations. Large amounts of background methylation (e.g., equal to or greater than 20 molecules) also raises the noise floor (e.g., the total amount of methylation seen in subjects without cancer). Large amounts of background methylation also effect the ability to detect relative changes of the cancer over time as the background is likely to be present each time point.

Previous work established an amplicon blacklist that contributed significant background methylation (see Example 2). This blacklist was generated by analyzing 4 samples from 4 healthy subjects.

Although effective at limiting the amount of background methylation, there remained a need for more comprehensive analysis of non-cancer samples to better establish an updated amplicon blacklist. As noted above, 16 specimens from 10 separate subjects previously run on the methylation assay were analyzed to determine an updated amplicon blacklist. The updated blacklist was applied to the methods described herein and samples were assessed for whether clinical interpretations changed significantly following analysis using the amplicon blacklist.

Methods. The training set included the 16 specimens from 10 separate subjects described above. Analysis included 8 specimens from batch 2 that did not have cancer but underwent a liver surgical procedure. These 8 specimens were collected from four subjects at 2 times. Subjects were 38, 39, 83 and 84 years old. Analysis also include 8 specimens from 6 healthy subjects: 2 subjects had 2 time points each, the rest each had one.

To determine an updated amplicon blacklist two approaches were used: a personalized amplicon blacklist that was patient or sample specific and a global amplicon blacklist.

7.8.1. Personalized Blacklist

A personalized approach enables blacklisting of only loci determined likely to be contributing background methylation signal in a particular sample. One non-limiting example of "personalized blacklisting" or "sample-specific blacklisting" included evaluating the buffy coat methylation signal for loci with high methylation cfDNA signal in non-cancer subjects (see FIG. 9A-9F).

Additional factors for identifying loci to be included in "personalized blacklists" included determining age and sex of the patients from whom the samples were taken.

FIG. 9A shows an example of loci used in a "personalized blacklist": intron cg03134157_77 ("intron 0313"). As shown in FIG. 9A, tumor QE for intron 0313 showed significantly greater cfDNA methylation than buffy coat methylation only when there as significant buffy coat methylation. Tumor QE was calculated by subtracting blue from red. Error bars indicated one standard deviation as estimated by molecular counting noise based on the raw QE. Overall, the consistency of methylation at intron 0313 or little to no methylation at intron 0313 meant that the buffy coat methylation threshold for this locus was about 20 tumor QE. This meant that the buffy coat methylation threshold would be about 20 tumor QE to properly exclude this locus. Note, an excessively small buffy coat threshold may risk blacklisting too many loci (essentially becoming a global blacklist).

A second loci was analyzed for its use in a "personalized blacklist." FIG. 9B shows methylation of intron cg20907051_11 ("intron 2090"). In particular, intron 2090 showed non-significant differences in cfDNA methylation in buffy coat methylation regardless of whether there was significant buffy coat methylation (see FIG. 9B). Because the vast majority of healthy samples tested have non-zero tumor QE, intron 2090 is example of a locus to blacklist for all samples.

Additional loci analyzed for inclusion in a "personalized blacklist" are shown in FIG. 9C-9F. FIG. 9C shows that tumor QE for intron_cg12880300_0 had an average of 59 tumor QE and had greater than 2 tumor QE in 9 out of 16 specimens. This locus was an example of a loci to blacklist for all samples due to the consistently high buffy coat methylation and variable cfDNA methylation.

FIG. 9D shows tumor QE for locus IRX4_cg13974394_0 ("IRX4"). For the IRX4 locus, significant tumor QE (red greater than blue) was seen in just 1 out of 16 specimens. This one sample was not flagged during QC. In fact, reads per QCT were about 4.9 for this cfDNA sample, which was lower than the other samples but not significantly so. This data suggested that the IRX4 may be best assessed on a sample by sample basis. Additionally, the data suggested that the high gDNA signal makes any actual tumor QE measurement on this locus relatively imprecise. Moreover, methylation appears to be correlated with age in this locus. BTO-23 and BTO-24 are in their 80s, BTO-21 and BTO-22 are in their late 30s, and healthy volunteers are overwhelmingly on the young side.

FIGS. 9E-9F show tumor QE for locus EMID2_cg25290307_0 ("EMID2) and intron_cg11453719_0, respectively. As shown in FIG. 9E, a filter of 10 QE (dashed line) for gDNA would have filtered out BTO-21_2, BTO-23_1, and BTO-23_2, but not BTO-24_2. As shown in FIG. 9F, a filter of 10 QE (dashed line) for gDNA would have filtered out all sample except BTO-24_1 and healthy_009_1. In these two loci, a personalized blacklist approach would require a relatively strict threshold of 10 QE, but even that fails to ignore spurious methylation signals in several samples. Therefore, it may be best to include these loci on a global blacklist.

7.8.2. Global Blacklist

To determine the criteria for including amplicons on a global blacklist, an empirical approach was used with set thresholds for mean tumor methylated QE and max tumor methylated QE (described below). The thresholds were applied to determine the blacklist and calculate the new total tumor QE in non-cancer samples. Thresholds were also applied to previous analysis (e.g., UCSD and UF results) to determine if these results were still clinically valid.

This analysis focused, in part, on the top 20 amplicons based on mean tumor methylated QE (see Table 2). In Table 2, the columns indicate the number of samples with greater than 2 tumor QE for that locus (n_samples_gt2), mean tumor QE (mean_tumor_norm) and max tumor QE (max_tumor_norm) across all 16 samples, and the mean buffy coat methylated QE (mean bg_norm).

TABLE 2

Top 20 amplicons based on mean tumor methylated QE

| amplicon_name | n_samples_gt2 | mean_tumor_norm | max_tumor_norm | mean_bg_norm |
|---|---|---|---|---|
| intron_cg12880300_0 | 9 | 59.175 | 309.998 | 276.094 |
| intron_cg20907051_11 | 12 | 35.4 | 178.619 | 51.837 |
| CDSA_cg00916536_0 | 13 | 21.457 | 66.402 | 47.985 |
| intron_cg03134157_77 | 3 | 16.839 | 173.932 | 26.812 |
| intron_cg11453719_0 | 7 | 12.72 | 77.711 | 7.741 |
| EMID2_cg25290307_0 | 5 | 12.093 | 58.953 | 18.124 |
| WTI_cg02524954_4 | 8 | 9.652 | 69.461 | 35.228 |
| intron_cg26763727_7 | 6 | 9.593 | 75.436 | 3.454 |
| TLX3_cg05787556_10 | 5 | 7.603 | 44.381 | 21.624 |
| IRX4_cg13974394_0 | 1 | 6.338 | 101.406 | 7 |
| C17orf64_cg12788108_85 | 7 | 6.044 | 46.582 | 0.388 |
| TNFRSF10C_cg05636175_0 | 10 | 5.538 | 42.451 | 0.119 |
| PRHOXNB_cg27513935_0 | 5 | 4.736 | 37.049 | 0.571 |
| ITPRIPL1_cg17932631_8 | 7 | 4.237 | 23.643 | 0 |
| CDH13_cg19369556_56 | 4 | 4.22 | 26.412 | 0.359 |
| ASCL1_cg17015844_34 | 8 | 3.897 | 28.098 | 0.157 |
| NPY5R_cg11784623_3 | 5 | 3.508 | 39.096 | 1.196 |
| BARHL1_cg19793376_2 | 5 | 3.155 | 30.034 | 0.491 |
| intron_cg15992563_52 | 3 | 2.877 | 30.529 | 0.143 |
| DIDO1_cg24804517_46 | 9 | 2.838 | 11.782 | 0.238 |

Based in part on the analysis of the top 20 amplicons as shown in Table 2, the thresholds for the global blacklist included: (1) max tumor QE in any non-cancer specimen>15; and (2) mean tumor QE (including 0s)>2.

In a non-limiting example, applying the thresholds of (1) max tumor QE in any non-cancer specimen>15; and (2) mean tumor QE (including 0s)>2 resulted in a global blacklist that included 32 amplicons. Compared to the previous blacklist (see Table 3), 16 amplicons were overlapping, which meant 6 amplicons were removed and 16 were added.

TABLE 3

| amplicon_name | old_blacklist | new_blacklist |
|---|---|---|
| ALDH1A2_cg02900766_3 | yes | yes |
| ASCL1_cg17015844_34 | yes | yes |
| BARHL1_cg19793376_2 | | yes |
| C17orf64_cg12788108_85 | yes | yes |
| CD8A_cg00916536_0 | yes | yes |
| CDH13_cg19369556_56 | yes | yes |
| DIDO1_cg24804517_46 | yes | yes |
| EMID2_cg25290307_0 | | yes |
| FOXF2_cg19519310_22 | | yes |
| GDF10_cg14720763_6 | | yes |
| GPC5_cg26960333_0 | yes | yes |
| HAAO_cg20857709_0 | yes | yes |
| HIST1H2BB_cg26426142_0 | | |
| intron_cg01418261_0 | | yes |
| intron_cg01683794_56 | yes | yes |
| intron_cg03134157_77 | | |
| intron_cg03933990_11 | yes | yes |
| intron_cg04908789_0 | | yes |
| intron_cg11453719_0 | yes | yes |
| intron_cg12880300_0 | yes | yes |
| intron_cg15992563_52 | | yes |
| intron_cg16476975_10 | yes | |
| intron_cg20907051_11 | yes | yes |
| intron_cg26763727_7 | yes | yes |
| intron_cg27452217_0 | | |
| IRX4_cg13974394_0 | yes | yes |
| ITPRIPL1_cg17932631_8 | yes | yes |
| JAM3_cg04913265_0 | yes | yes |
| KCNA6_cg10671668_0 | | yes |
| NPY5R_cg11784623_3 | | yes |
| OTX2OS1_cg14248715_9 | yes | |
| PRHOXNB_cg27513935_0 | yes | yes |
| TLX3_cg05787556_10 | yes | yes |
| TLX3_cg25942450_0 | yes | |
| TNFRSF10C_cg05636175_0 | | yes |

TABLE 3-continued

| amplicon_name | old_blacklist | new_blacklist |
|---|---|---|
| USP44_cg00927554_0 | | yes |
| WT1_cg02524954_4 | | yes |
| ZFP28_cg12973930_0 | | yes |
| total | 22 | 32 |

The new global blacklist generated based on the thresholds described above (i.e., (1) max tumor QE in any non-cancer specimen>15; and (2) mean tumor QE (including 0s)>2) was applied to 16 non-cancer specimens to determine the noise floor. As shown in FIG. 10, no sample had methylation greater than 114 tumor QE. Therefore, the noise floor was set at 120 for additional analysis. However, one skilled in the art would appreciate the noise floor would change based on a similar type of analysis applied to a different sample or different set of samples.

The new global blacklists were then compared to the old global blacklists. As shown in FIG. 11, comparing the normalized total tumor molecules using either the old or new global blacklist, most subjects had equal if not fewer tumor molecules. In addition, the methylation results for all 30 subjects were manually inspected and assessed whether the clinical interpretations would have changed. Out of 30 total subjects, only 2 subjects had slightly different results, both of which were within the statistical noise. For both subjects 8272 and 6885, the results for the last collection changed slightly, but still within molecular noise error bars (see FIGS. 12A-12D). Overall, this data showed that small changes to the blacklist did not significantly affect the clinical results.

The new global blacklists were then compared to the old global blacklists for 5 patient samples (see BTO-1 to BTO-5 in FIGS. 13A-13E, respectively) that had surgical removal of liver cancer, though the patients had a range of cancer stages. As shown in FIGS. 13A-13E, the trend for each patient was concordant with the previous analysis. Additionally, each patient had a decrease in tumor methylation, with the exception of BTO-1, who was a Stage 4 liver cancer patient where high levels of methylation was detected and a sample was provided one day after surgery.

7.8.3. Conclusion

This data showed the benefits of a global blacklist versus a personalized blacklist (either patient- or sample-specific). In particular, a global blacklist avoided having to deal with unanswered biological variability and temporal variability questions. However, this analysis does not rule out use of a personalized blacklist, but additional optimization may be needed to design effective personalized blacklists.

This data also showed that adjusting the blacklist from 22 to 32 amplicons did not significantly change clinical results beyond measurement noise in two clinical study datasets. Importantly, the noise floor increased from 50 to 120 normalized total tumor QE.

7.9. Example 7. Analytical and Clinical Validation of the Pan-Cancer Assay

The pan-cancer assay provided in this disclosure and described, for example, in Example 5 underwent analytical validation, including testing for accuracy, precision, reproducibility, sensitivity, and specificity.

7.9.1. Introduction and Summary of Validation Arms

Accurate, rapid, and accessible treatment monitoring for cancer patients is an unmet medical need. When the outcome of a cancer treatment regimen is uncertain, determining whether a treatment is effective for a patient earlier rather than later could enable a switch to a different treatment regimen thus potentially prolonging life, reducing unnecessary side effects from ineffective treatments and improving quality of life, and improving the overall efficiency of the health care system. Assessing treatment efficacy earlier, or even predicting the eventual treatment outcome, can be of extra importance for late stage cancer patients or for the efficient execution of clinical studies for novel cancer therapies, where time is of the essence.

ctDNA (circulating tumor DNA), obtained through a liquid biopsy from the cancer patient, has been shown to reflect the amount of cancer present in the patient. In addition, methylation has been shown to be a robust biomarker of cancer, with several groups developing methylation-based assays using ctDNA for various cancer diagnostics applications. Using our patented QCT technology (Tsao et al., 2019), Applicant's has developed a novel assay called pan cancer assay to quantify the amount of methylation in the ctDNA for an accurate and precise treatment monitoring application.

The validation studies were conducted to demonstrate the analytical and clinical validity of the pan-cancer treatment monitoring assay.

The analytical validations included: Arm 1: Accuracy, Precision, and Reproducibility on Sheared Tumor DNA Samples; Arm 2: Concordance on Clinical Samples with Known Clinical Outcomes; Arm 3: Limit of Detection using Sheared Tumor DNA Samples; and Arm 4: Diversity of Cancer Types.

7.9.2. Arm 1: Accuracy, Precision, and Reproducibility on Sheared Tumor DNA Samples The aim for Arm 1 was to calculate the accuracy, precision, and reproducibility based on sheared tumor DNA samples. Replicates of sheared tumor DNA samples at 1% and 2% tumor fraction were made from a total of 7 different tumors from 7 different cancer types. The sheared tumor DNA samples were processed in two different batches, and loaded on two different sequencers. The Response Score, which describes the amount of methylation in the sample, was calculated for each sample, and the Response Score for 1% and 2% tumor fraction samples were compared with each other.

In summary and described in further detail below, data from Arm 1 showed: 100% accuracy (i.e., 40 out of 40 comparisons called correctly); 100% precision (i.e., 0 subjects with discordant results within each batch); and 100% reproducibility (i.e., 9 out of 19 comparisons concordant between batches).

In both batches, all comparisons between 1% and 2% tumor fraction samples that passed QC were called as "Increase," which is concordant with the identity of these samples. The Response Scores from both batches are as shown in FIG. 14 and FIG. 15.

Additional calculations were made for sensitivity and specificity of the pan-cancer assay. Sensitivity was calculated based on comparing 1% and 2% samples, as described above, and specificity was calculated by comparing 1% samples against themselves and 2% samples against themselves within each batch. This analysis revealed sensitivity=100% [95% CI: 91.2%, 100%] (i.e., 40 out of 40 comparisons) and specificity=100% [95% CI: 95.5%, 100%] (i.e., 80 out of 80 comparisons).

Overall, the result from Arm 1 demonstrates that the pan-cancer assay is accurate, precise, and reproducible across operators and sequencers.

7.9.3. Arm 2: Concordance on Clinical Samples with Known Clinical Outcomes

The aim for Arm 2 was to assess the accuracy of the pan-cancer assay on clinical samples from a total of 20 subjects. These 20 subjects were composed of 8 cancer subjects with known clinical outcomes, and 12 healthy subjects without known history of cancer. Response Scores were measured at two time points for each subject. Calls were made based on the Response Scores from both time points, and the calls were compared with known clinical outcomes.

In summary and described in further detail below, data from Arm 2 showed: 100% accuracy for cancer subjects (6 out of 6 concordant calls); 100% accuracy for healthy subjects (11 out of 11 concordant calls).

Out of the 6 cancer subjects with detectable signal, all 6 subjects had calls that were concordant with known clinical outcomes. Results for all cancer subjects are plotted in FIG. 16, and known clinical outcomes can be found in Table 4.

TABLE 4

Known clinical outcomes for 6 cancer subjects

| Subject ID | Cancer Type | Known Clinical Outcome | Validation Call | Interpretation |
|---|---|---|---|---|
| 107034 | Lung | Partial response | Decrease | Concordant |
| 107355 | Lung | Partial response | Decrease | Concordant |
| 107022 | Pancreas | Progression | Increase | Concordant |
| 150118702 | Pancreas | Progression | Increase | Concordant |
| 150118713 | Lung | Progression | Increase | Concordant |
| 107526 | Lung | Partial response | Decrease | Concordant |

Out of the 12 healthy subjects, 11 subjects had no change in cancer or an Indeterminate call, which is concordant with the healthy status of these subjects (see FIG. 17).

In summary, the results for Arm 2 demonstrate the validity of the pan-cancer assay to accurately assess clinical samples from a total of 20 subjects.

7.9.4. Arm 3: Limit of Detection Using Sheared Tumor DNA Samples

The aim for Arm 3 was to assess the limit of detection of the pan-cancer assay by measuring sensitivity at different input conditions.

For these experiments, the sheared tumor DNA samples at 0%, 0.25%, 0.5%, 1%, and 2% tumor fraction were made from a single tumor and its matching buffy coat and analyzed using the pan-cancer assay. For each tumor fraction, the Response Score was measured for 16 replicates, and these measurements were used to calculate CV. Assay sensitivity was calculated by comparing Response Scores for samples at each tumor fraction with the Response Scores of 0% samples, from which the limit of detection was determined.

In summary and described in further detail below, the results showed the Limit of Detection=0.25% Tumor Fraction.

The limit of detection was defined as the lowest tumor fraction with at least 95% sensitivity. For 0.25% tumor fraction samples, the sensitivity was 96.5% [95% CI: 93.4%, 98.4%]. The sensitivities for each tumor fraction are shown in FIG. 18.

The Response Scores for each tumor fraction are plotted in FIG. 19. As expected, higher tumor fractions corresponded to higher Response Scores. Within each group of technical replicates, the CV of the Response Score was calculated for a given tumor fraction (see FIG. 19). There is clear separation between the 0% and 0.25% tumor fractions, which is in line with the 0.25% tumor fraction limit of detection (see FIG. 19). The standard deviation and mean of each tumor fraction were used to calculate CV.

In summary, the results for Arm 3 demonstrate that the limit of detection for the pan-cancer assay is at least 0.25% tumor fraction.

7.9.5. Arm 4: Diversity of Cancer Types

The aim for Arm 4 is to assess the performance of the pan-cancer assay on different cancer types. For each of the 54 different cancer patients spanning 10 unique cancer types, a tumor gDNA sample and a matched buffy coat gDNA sample were processed.

For these experiments, bioinformatic simulations were used to assess the performance of the pan-cancer assay on different cancer types. For example, bioinformatics was used to simulate 1% and 2% tumor DNA samples by scaling down the number of methylated molecules based on estimated tumor purity. Using the standard analysis workflow, all 2% tumor sample Response Scores were correctly called as Increased relative to 1% tumor sample Response Scores (see FIG. 20; Table 5). As shown in Table 5, sensitivity across cancer types was 100% [95% CI: 93.4%, 100%].

TABLE 5

Sensitivity for Distinguishing 1% and 2% Tumor DNA Samples Across Cancer Types

| Cancer Type | Fraction of Cancer Patients Called Correctly | Sensitivity [95% Confidence Interval] |
|---|---|---|
| Lung | 18 out of 18 | 100% [81.5%, 100%] |
| Colorectal | 11 out of 11 | 100% [71.5%, 100%] |
| Breast | 11 out of 11 | 100% [71.5%, 100%] |
| Liver | 4 out of 4 | 100% [39.8%, 100%] |
| Pancreas | 3 out of 3 | 100% [29.2%, 100%] |
| Ovarian | 2 out of 2 | 100% [15.8%, 100%] |
| Prostate | 2 out of 2 | 100% [15.8%, 100%] |
| Endometrial | 1 out of 1 | 100% [2.5%, 100%] |
| Stomach | 1 out of 1 | 100% [2.5%, 100%] |
| Brain | 1 out of 1 | 100% [2.5%, 100%] |
| TOTAL | 54 out of 54 | 100% [93.4%, 100%] |

In summary, this data confirms that the pan-cancer assay performs with high sensitivity across a variety of cancer types. For all 54 cancer patients included in this validation arm, the pan-cancer assay detected increases in Response Score when a change from 1% to 2% tumor fraction was simulated.

7.9.6. Conclusion

This analytical and clinical validation report describes the results from the experimental arms performed to support the validation of the pan-cancer assay. Overall, the results show that the assay has high accuracy and precision, high reproducibility, high sensitivity and specificity, and a low limit of detection. By measuring the amount of ctDNA in cancer patients through a liquid biopsy, the pan-cancer assay gives oncologists additional information that can be used to improve clinical outcomes for their cancer patients.

7.10. Example 8. Detection of Methylation Concordant with Disease Progression

The pan-cancer assay was used to assess concordance between methylation and disease progression. For this analysis, methylation and CT imaging were both used to assess disease progression in four patients. Methylation was monitored using the pan-cancer assay. CT imaging was performed by the clinician and used to stage disease progression. The data as shown in FIGS. 21-24 is presented as methylation ("tumor QE") over time ("days since treatment start") with triangles indicated a clinician-based staging of disease progression.

FIG. 21 shows methylation analysis for a 56 year old male subject with pancreatic ductal adenocarcinoma stage IV at time of first collection and clinician-based staging of disease progression (see triangles in FIG. 21). As noted in FIG. 21, methylation analysis was performed at the indicated time points, which coincided with a treatment regimen of: folfirinox ("folfiri"), followed by folfiri maintenance, followed by folox. Here, methylation level was in concordance with the clinician-based staging. For example, a decrease in methylation corresponded to a decrease in size of the tumor or stable growth of the tumor (as indicated by the clinician), and an increase in methylation corresponded with possible disease progression (as indicated by the clinician).

FIG. 22 shows methylation analysis for a 50 year old male subject with pancreatic adenocarcinoma stage IV at time of first collection and clinician-based staging of disease progression (see triangle in FIG. 22). As noted in FIG. 22, methylation analysis was performed at the indicated time points, which coincided with a treatment regimen of: fluorouracil 5000 mg continuous over 46 hours+leucovorin 800 mg+oxaliplatin 180 mg+Irinotecan 300 mg. Here, the methylation level was in concordance with the clinician-based staging. For example, as methylation levels increased prior to day 200 and continuing to rise beyond day 200, the clinician-based staging indicated disease progression.

FIG. 23 shows methylation analysis for an 87 year old male subject with colorectal adenocarcinoma stage IV at time of first collection. FIG. 23 also shows clinician-based staging of disease progression (see triangle in FIG. 23). As noted in FIG. 23, methylation analysis was performed at the indicated time points, which coincided with a treatment regimen of: 6 cycles of fluorouracil 1100 mg+leucovorin 1100 mg+Bevacizumab 500 mg. Here, the methylation level was in concordance with the clinician-based staging. For example, as methylation levels increased prior to day 200 and continuing to rise beyond day 200, the clinician-based staging indicated disease progression.

FIG. 24 shows methylation analysis for a 56 year old female subject with lung squamous cell carcinoma stage IV at time of first collection. FIG. 24 also shows clinician-based staging of disease progression (see triangle in FIG. 24). As noted in FIG. 24, methylation analysis was performed at the indicated time points, which coincided with a treatment regimen of: docetaxel. Similar to the patients analyzed in FIGS. 21-23, the methylation level here was in concordance with the clinician-based staging.

7.11. Example 9. Concordance with Variant Allele Fraction

The pan-cancer assay was also used to assess concordance between methylation and variant allele fraction.

For this experiment, 40 samples were run through a treatment selection assay. For each sample, an aliquot of plasma was collected at the same time point as the methylation assay. From the treatment selection assay, the maximum variant allele fraction (VAF) was calculated and compared against the methylation assay. As shown in FIG. 25, there was a correlation between the maximum VAF and the number of methylated molecules. A perfect one-to-one correlation was not expected because somatic mutations were likely to be heterogenous throughout the tumor and may not reflect the total abundance of the cancer.

One limitation of treatment selection assays was false negative actionable mutations. Given the correlation between VAF and methylation, the methylation results were used to inform whether a false negative actionable mutation identified with VAF was likely a false negative, or not. For example, if no actionable mutations were found but methylation levels were low, this suggested a low tumor fraction at this time point and possible false negative actionable mutations due to the low number of tumor molecules. On the other hand, if no actionable mutations were detected but methylation levels were high, this suggested a high tumor fraction at this time point, and that a false negative actionable mutation of large magnitude would be unlikely.

In summary, the concordance between VAF and methylation showed that methylation (i.e., methylation analyzed and identified according to the methods described herein) can be used to inform the results of VAF analysis, which in turn, can be used for supplementing therapy selection assay decisions.

7.12. Example 10. Changes in Methylation Profiles

The pan-cancer assay was also used to assess methylation profiles over time. For these experiments, methylation patterns were analyzed for two subjects (Subject 6885 and subject 5458) over 294 days and 250 days, respectively. In summary and described in greater detail below, it was observed that some subjects had relatively constant methylation profiles over time, whereas some patients had large changes in their methylation profiles.

For example, as shown in FIG. 26, for Subject 6885, each new time point had novel loci that were methylated. However, with the exception of loci present at the Day 0 time point, these novel loci did not contribute a significant amount of methylation at subsequent time points. For example, the loci that first appear on Day 63 did not contribute a significant amount of methylation at later time points.

In a second, non-limiting example shown in FIG. 27, for Subject 5458, there was an increase in total methylation on Day 119 that combined with interesting methylation patterns. In particular, on Day 119, slightly more than half of the methylation comes from new loci (i.e., methylated loci not detected at day 0, 35, or 63), suggesting that the tumor significantly evolved compared to previous time points. In fact, time points after Day 119 maintained a significant fraction of loci that first appeared on Day 119, indicating that the change in tumor methylation was persistent. Based on the large increase and the sudden change in composition of the methylation pattern, this subject was flagged as warranting a repeat of a treatment selection assay to detect any novel somatic mutations present in the cancer. Clinically, a pattern such as that seen in Subject 5458 may indicate the need to re-evaluate treatment options.

7.13. Conclusion for Examples 8-10

Overall, this data established the pan-cancer assays utility for (1) detecting concordance between methylation and disease progress; (2) detecting concordance between methylation and variant allele fraction; and (3) assessing methylation profiles over time.

7.14. Example 11: Methylation Pattern in Patient with Pancreatic Ductal Adenocarcinoma The pan-cancer assay was used to assess methylation profiles over time in a patient with pancreatic ductal adenocarcinoma. The assay was used to detect a decrease in methylated molecules in the circulating tumor DNA (ctDNA) compared to the initial measurement. Aberrantly methylated DNA is a known marker of cancer cells (PMID 15542813), and a change in methylated ctDNA corresponds to a change in tumor fraction. This result suggests that tumor fraction has decreased compared to the previous measurement.

For these experiments, plasma and buffy coat were isolated from whole blood collected in a Streck cell-free DNA tube. Cell-free DNA (cfDNA) was extracted from the plasma, and genomic DNA (gDNA) was extracted from the buffy coat. The number of methylated molecules was quantified in both cfDNA and gDNA using QCT molecular counting technology (PMID: 31591409) at >500 locations in the genome known to be hypermethylated in cancer compared to non-cancerous tissue and blood. Methylation measured in gDNA was subtracted from cfDNA methylation in order to remove background from the ctDNA signal. The remaining cfDNA methylated molecules were summed across all hypermethylation locations to calculate the Tumor Methylation Score™. FIG. 28 shows the Tumor Methylation Score™ represented as the normalized sum of methylated molecules at >500 loci that are hypermethylated in circulating tumor DNA (ctDNA). As shown in FIG. 28, a decrease in Tumor Methylation Score™ was detected that corresponds to a decrease in methylated ctDNA molecules. In particular, FIG. 28 shows that tumor fraction decreased compared to the previous measurement by about 3.1-fold.

The Tumor Methylation Score™ from the current collection was compared to the most recently reported Tumor Methylation Score™ to determine an increase, decrease, or no change call. The change in Tumor Methylation Score™ must exceed a significance threshold in order to be reported as an increase or a decrease. No interpretive calls for change in Tumor Methylation Score™ are made for baseline tests without any prior collections. Results should be discussed with a medical professional and interpreted in conjunction with the patient's complete clinical history within the context of multiple timepoints.

In some cases, methylation may not be reported when the sample contains an insufficient amount of DNA. Results below the Tumor Methylation Score™ limit of detection (LOD), depicted on the graph by cross-hatched shading, are not interpreted and will be reported as less than the LOD. Performance specifications based on internal validation studies demonstrated that this assay can distinguish a 0.2 percentage point change in tumor fraction with 3 standard deviations of separation. This pan-cancer assay was designed for quantifying Tumor Methylation Score™ in patients with solid tumors. Results may vary or be invalid if the patient has undergone recent blood transfusion, stem cell transplant, or other procedures that may significantly affect the composition of cfDNA or buffy coat gDNA.

8. EQUIVALENTS AND INCORPORATION BY REFERENCE

While the invention has been particularly shown and described with reference to a preferred embodiment and various alternate embodiments, it will be understood by persons skilled in the relevant art that various changes in form and details can be made therein without departing from the spirit and scope of the invention.

What is claimed is:

1. A method to quantify DNA methylation in a sample comprising cell free DNA (cfDNA) sequences, the method comprising:

- treating the sample to encode presence or absence of DNA methylation in the cfDNA sequences, wherein treating the sample to encode the presence or absence of DNA methylation comprises bisulfite conversion, and wherein the sample comprises at least ten target loci from the cfDNA sequences;
- adding to the sample a set of synthetic molecules, the set of synthetic molecules comprising:
  - target-associated regions having a nucleotide sequence that matches a target sequence region of an endogenous target molecule comprising at least one of the target loci, and
  - variation regions with a nucleotide sequence that does not match a sequence region of an endogenous target molecule;
- generating a co-amplification mixture comprising an amplified set of synthetic molecules and an amplified set of the at least ten target loci from the cfDNA sequences;
- sequencing the co-amplification mixture at a read depth of at least one read sequence per molecule in the sample to generate sequence reads;
- determining a number of the sequence reads that are methylated sequence reads;
- processing the methylated sequence reads using one or more of the following:
  - filtering out selected hypermethylated target loci; or
  - subtracting background methylation;
- determining a number of methylated molecules in the sample for each target loci based on the number of methylated reads from the sample for each target loci and a number of sequence reads from the set of synthetic molecules; and
- aggregating the number of methylated molecules across at least two of the at least ten target loci to quantify DNA methylation in the sample.

2. The method of claim 1, wherein the sample is taken from a blood draw comprising plasma and buffy coat, wherein the plasma comprises cfDNA and the buffy coat comprises genomic DNA (gDNA) sequences.

3. The method of claim 2, further comprising extracting cfDNA from the plasma and gDNA sequences from the buffy coat from the sample prior to treating the sample to encode the presence or absence of DNA methylation.

4. The method of claim 2, further comprising quantifying DNA methylation in a sample comprising DNA sequences from the buffy coat.

5. The method of claim 4, comprising:

treating the sample comprising DNA sequences from the buffy coat to encode the presence or absence of DNA methylation in the DNA sequences, wherein the sample comprising DNA sequences from the buffy coat comprises at least ten additional target loci from the DNA sequences;

adding to the sample a set of synthetic molecules, the set of synthetic molecules comprising:

target-associated regions having a nucleotide sequence that matches a target sequence region of an endogenous target molecule comprising at least one additional target loci, and variation regions with a nucleotide sequence that does not match a sequence region of an endogenous target molecule;

generating a second co-amplification mixture comprising an amplified set of synthetic molecules and an amplified set of the at least ten additional target loci from the DNA sequences from the buffy coat;

sequencing the co-amplification mixture to generate additional sequence reads;

determining a number of the additional sequence reads that are additional methylated sequence reads;

determining a number of methylated molecules in the sample comprising DNA sequences from the buffy coat based on the number of additional methylated reads from the sample comprising DNA sequences from the buffy coat and a number of additional sequence reads from the set of synthetic molecules; and aggregating the number of methylated molecules in the sample comprising DNA sequences from the buffy coat across at least two target loci to quantify DNA methylation in the sample comprising DNA sequences from the buffy coat, thereby quantifying DNA methylation in gDNA sequences from the buffy coat.

6. The method of claim 5, wherein the set of synthetic molecules is a set of quality control templates (QCTs).

7. The method of claim 5, wherein aggregating the number of methylated molecules in the sample comprising DNA sequences from the buffy coat comprises aggregating additional target loci from the at least ten additional target loci that contain lower than a threshold amount of methylated molecules in the buffy coat sample.

8. The method of claim 1, wherein the set of synthetic molecules is a set of quality control templates (QCTs).

9. The method of claim 1, further comprising adding a spike-in of known sequence and quantity to the sample prior to the treating step.

10. The method of claim 1, wherein generating the co-amplified mixture comprises amplifying at least 100 target loci or amplifying at least 500 target loci.

11. The method of claim 1, wherein the co-amplification mixture is sequenced at a read depth of 10 or more reads per molecule, 100 or more reads per molecule, or 1000 or more reads per molecule.

12. The method of claim 1, wherein the sample further comprises at least one normalization locus that is expected to have methylation above a threshold amount in cfDNA across both cancerous and non-cancerous tissue.

13. The method of claim 12, wherein the co-amplification mixture comprises an amplified set of synthetic molecules, an amplified set of the at least 10 target loci, and an amplified at least one normalization locus.

14. The method of claim 13, further comprising normalizing the aggregate number of methylated molecules from all or a subset of the at least 10 target loci by the methylated molecules for the amplified at least one normalization locus.

15. The method of claim 2, wherein the subtracting background methylation comprises subtracting a number of methylated molecules as measured in the buffy coat from the number of methylated molecules in the cfDNA.

16. The method of claim 2, wherein the subtracting background methylation comprises subtracting a number of methylated molecules as measured in the buffy coat from the number of methylated molecules in the cfDNA on a per-locus basis.

17. The method of claim 1, wherein the filtering out selected hypermethylated target loci comprises filtering out target loci having a total number of methylated molecules above a threshold.

18. The method of claim 17, wherein the threshold comprises a pre-determined mean tumor methylated quantitative equivalent (QE), a predetermined max tumor methylated QE, or a combination thereof.

19. The method of claim 1, wherein the selected hypermethylated target loci comprise target loci having a hypermethylated cfDNA signal in non-cancer subjects.

20. The method of claim 1, wherein the filtering out selected hypermethylated target loci is performed prior to determining the number of methylated molecules in the sample.

21. The method of claim 1, wherein the subtracting background methylation is performed prior to determining the number of methylated molecules in the sample.

22. The method of claim 1, wherein the filtering out hypermethylated loci or the subtracting background methylation is performed prior to quantifying the number of methylated molecules in the sample.

23. A method to quantify DNA methylation in a sample comprising cell free DNA (cfDNA) sequences, the method comprising:

treating the sample to encode presence or absence of DNA methylation in the cfDNA sequences, wherein treating the sample to encode the presence or absence of DNA methylation comprises bisulfate conversion or enzymatic conversion, and wherein the sample comprises at least ten target loci from the cfDNA sequences and at least one normalization locus that is expected to have methylation above a threshold amount in cfDNA across both cancerous and non-cancerous tissue;

adding to the sample a set of synthetic molecules, the set of synthetic molecules comprising:

target-associated regions having a nucleotide sequence that matches a target sequence region of an endogenous target molecule comprising at least one of the target loci, and variation regions with a nucleotide sequence that does not match a sequence region of an endogenous target molecule;

generating a co-amplification mixture comprising an amplified set of synthetic molecules and an amplified set of the at least ten target loci from the cfDNA sequences;

sequencing the co-amplification mixture at a read depth of at least one read sequence per molecule in the sample to generate sequence reads;

determining a number of the sequence reads that are methylated sequence reads;

determining a number of methylated molecules in the sample for each target loci based on the number of methylated reads from the sample for each target loci and a number of sequence reads from the set of synthetic molecules; and aggregating the number of methylated molecules across at least two of the at least ten target loci to quantify DNA methylation in the sample.

24. The method of claim 23, wherein the set of synthetic molecules is a set of quality control templates (QCTs).

25. The method of claim 23, wherein the co-amplification mixture comprises an amplified set of synthetic molecules, an amplified set of the at least 10 target loci, and an amplified at least one normalization locus.

26. The method of claim 25, further comprising normalizing the aggregate number of methylated molecules from all or a subset of the at least 10 target loci by the methylated molecules for the amplified at least one normalization locus.

27. The method of claim 23, wherein the sample is taken from a blood draw comprising plasma and buffy coat, wherein the plasma comprises cfDNA and the buffy coat comprises genomic DNA (gDNA) sequences.

28. The method of claim 27, further comprising extracting cfDNA from the plasma and gDNA sequences from the buffy coat from the sample prior to treating the sample to encode the presence or absence of DNA methylation.

29. The method of claim 27, further comprising quantifying DNA methylation in a sample comprising DNA sequences from the buffy coat.

30. The method of claim 29, further comprising:

treating the sample comprising DNA sequences from the buffy coat to encode the presence or absence of DNA methylation in the DNA sequences, wherein the sample comprising DNA sequences from the buffy coat comprises at least ten additional target loci from the DNA sequences;

adding to the sample a set of synthetic molecules, the set of synthetic molecules comprising:

target-associated regions having a nucleotide sequence that matches a target sequence region of an endogenous target molecule comprising at least one additional target loci, and variation regions with a nucleotide sequence that does not match a sequence region of an endogenous target molecule;

generating a second co-amplification mixture comprising an amplified set of synthetic molecules and an amplified set of the at least ten additional target loci from the DNA sequences from the buffy coat;

sequencing the co-amplification mixture to generate additional sequence reads;

determining a number of the additional sequence reads that are additional methylated sequence reads;

determining a number of methylated molecules in the sample comprising DNA sequences from the buffy coat based on the number of additional methylated reads from the sample comprising DNA sequences from the buffy coat and a number of additional sequence reads from the set of synthetic molecules; and aggregating the number of methylated molecules in the sample comprising DNA sequences from the buffy coat across at least two additional target loci to quantify DNA methylation in the sample comprising DNA sequences from the buffy coat, thereby quantifying DNA methylation in gDNA sequences from the buffy coat.

* * * * *

UNITED STATES PATENT AND TRADEMARK OFFICE

CERTIFICATE OF CORRECTION

PATENT NO. : 12,043,873 B2
APPLICATION NO. : 18/187578
DATED : July 23, 2024
INVENTOR(S) : Ye et al.

It is certified that error appears in the above-identified patent and that said Letters Patent is hereby corrected as shown below:

In the Claims

In Column 64, in Claim 23, Lines 42-43, delete "bisulfate conversion or enzymatic conversion," and insert -- bisulfite conversion, --, therefor.

Signed and Sealed this
Twenty-sixth Day of November, 2024

Katherine Kelly Vidal

Katherine Kelly Vidal
*Director of the United States Patent and Trademark Office*

SEQUENCE LISTING

```
Sequence total quantity: 2
SEQ ID NO: 1            moltype = DNA  length = 39
FEATURE                 Location/Qualifiers
source                  1..39
                        mol_type = genomic DNA
                        organism = Homo sapiens
SEQUENCE: 1
ggagaagtct gccgttactg ccctgtgggg caaggtgaa                      39

SEQ ID NO: 2            moltype = DNA  length = 39
FEATURE                 Location/Qualifiers
source                  1..39
                        mol_type = other DNA
                        organism = synthetic construct
SEQUENCE: 2
ggagaagtnn nnngttacta gtctgtnnnn naaggtgaa                      39
```